US008637578B2

(12) United States Patent  
Davis et al.

(10) Patent No.: US 8,637,578 B2  
(45) Date of Patent: Jan. 28, 2014

(54) REAGENTS AND METHODS FOR THE FORMATION OF DISULFIDE BONDS AND THE GLYCOSYLATION OF PROTEINS

(75) Inventors: Benjamin Guy Davis, Oxford (GB); David Philip Gamblin, Oxford (GB); Antony John Fairbanks, Oxford (GB); Philippe Garnier, Oxford (GB)

(73) Assignee: Isis Innovation Limited, Summertown, Oxford (GB)

( * ) Notice: Subject to any disclaimer, the term of this patent is extended or adjusted under 35 U.S.C. 154(b) by 1659 days.

(21) Appl. No.: 10/562,599

(22) PCT Filed: Jun. 24, 2004

(86) PCT No.: PCT/GB2004/002706  
§ 371 (c)(1),  
(2), (4) Date: Apr. 2, 2007

(87) PCT Pub. No.: WO2005/000862  
PCT Pub. Date: Jan. 6, 2005

(65) Prior Publication Data  
US 2007/0213506 A1 Sep. 13, 2007

(30) Foreign Application Priority Data

Jun. 24, 2003 (GB) .................................. 0314743.6  
Dec. 12, 2003 (GB) .................................. 0328884.2

(51) Int. Cl.  
*A61K 38/14* (2006.01)  
*A01N 59/02* (2006.01)  
*A61K 31/095* (2006.01)

(52) U.S. Cl.  
USPC ............ 514/706; 514/3.1; 514/20.9; 424/702

(58) Field of Classification Search  
None  
See application file for complete search history.

(56) References Cited

U.S. PATENT DOCUMENTS

| 5,759,823 | A | * | 6/1998 | Wong et al. ..................... 435/97 |
| 5,880,149 | A | * | 3/1999 | Grinstaff et al. .............. 514/492 |
| 2002/0019039 | A1 | | 2/2002 | Davis et al. |

FOREIGN PATENT DOCUMENTS

| EP | 0 256 486 A1 | 2/1988 |
| JP | 61-205249 | 9/1986 |
| WO | WO 94/00427 | 1/1994 |
| WO | WO 00/01712 | 1/2000 |
| WO | WO 00/64485 | 11/2000 |

OTHER PUBLICATIONS

H.M.A. Killa and D.A. Rabenstein. Anal. Chem. (1998) 60(20), pp. 2283-2287.*  
L. Engman et al. Tetrahedron (1994) 50(9), pp. 2929-2938.*  
K.S. Tan et al. Can. J. Chem. (1988) 66, pp. 54-60.*  
H.S. Hsieh et al. Biochemistry (1975) 14(8), pp. 1632-1636.*  
Davis, Benjamin G., et al. "Controlled Site-Selective Glycosylation of Proteins by a Combined Site-Directed Mutagenesis and Chemical Modification Approach," American Chemical Society, J. Org. Chem., 1998, pp. 9614-9615, 63.  
Davis, Benjamin G., et al. "Glycomethanethiosulfonates: powerful reagents for protein glycosylation," Tetrahedron: Asymmetry, 2000, pp. 245-262, 11.  
Davis, Benjamin G. "Mimicking Posttranslational Modifications of Proteins," Science, Jan. 2004, pp. 480-482, vol. 303.  
Dwek, Raymond A. "Glycobiology: Toward Understanding the Function of Sugars," Chem. Rev., 1996, pp. 683-720, 96.  
Field, Lamar, et al. "Biologically Oriented Organic Sulfur Chemistry," J. Org Chem., 1971, pp. 309-313, vol. 36, No. 2.  
Gamblin, David P., et al. "Glyco-SeS: Selenenylsulfide-Mediated Protein Glycoconjugation—A New Strategy in Post-Translational Modification," Angew. Chem. Int. Ed., 2004, pp. 828-833, vol. 43, No. 7.  
Gamblin, David P., et al. "Glycosyl Phenylthiosulfonates (Glyco-PTS): novel reagents for glycoprotein synthesis," Org. Biomol. Chem., 2003, pp. 3642-3644, vol. 1, No. 21.  
Johnston, Blair D., et al. "Synthesis of Thio-Linked Disaccharides by 1→2 Intramolecular Thioglycosyl Migration: Oxacarbenium versus Episulfonium Ion Intermediates," J. Org. Chem., 2000, pp. 4607-4617, vol. 65, No. 15.  
Rajca, A., et al. "New Mixed Disulfides of L-Cysteine Derivatives and of Glutathione with Diethyldithiocarbamic Acid and 2-Mercaptoethanesulfonic Acid," Arzneimittal Forschung/Drug Research, 1990, pp. 282-286, 40, No. 3.  
Rajca, Andrzej, et al. "Synthesis of Unsymmetrical Disulfides with Thiolsulfonates Immobilised on a Polystyrene Support," Tetrahedron Letters, Aug. 1990, pp. 6075-6076, 31, 42.  
Reich, Hans J., et al. "Organoselenium Chemistry. Alkylation of Acid, Ester, Amide, and Ketone Enolates with Bromomethyl Benzyl Selenide and Sulfide: Preparation of Selenocysteine Derivatives," J. Org. Chem., 1986, pp. 2981-2988, vol. 51, No. 15.  
Yamada, Shunichi, et al. "Syntheses of Thiamine Alkyl Disulfides," CAS XP002300619, 1954, pp. 963-966, 74 (Abstract).  
Journal of the American Chemical Society, American Chemical Society 1987, vol. 109, No. 18, pp. 5549-5551.  
CAplus Summary of: Journal, Dehnert P. et al., ZNBAD2; Zeitschrift fuer Naturforschung, Teil B: Anorganische Chemie, Organische Chemie, German, 34, 1979, 1646-1652, ISSN 0340-5087.

(Continued)

*Primary Examiner* — Satyanarayana R Gudibande  
(74) *Attorney, Agent, or Firm* — Blakely, Sokoloff, Taylor & Zafman LLP

(57) ABSTRACT

Methods and reagents for the formation of disulfide bonds, particularly in proteins, peptides and amino acids. The methods and reagents are particularly useful for the controlled glycosylation of proteins, peptides and amino acids. The methods utilize thiosulfonate or selenenylsulfide compounds as reagents or intermediates. Some proteins and peptides comprising selenenyl-sulfide groups also form part of the invention.

3 Claims, No Drawings

(56) References Cited

OTHER PUBLICATIONS

PCT International Search Report and Written Opinion for PCT/GB2004/002706, mailed Jun. 13, 2005, 14 pages.

Davis, Benjamin G., "The Controlled Glycosylation of a Protein With a Bivalent Glycan: Towards a New Class of Glycoconjugates, Glycodendriproteins", Chemm, Commun., 2001, pp. 351-352.

Davis, Benjamin G., "Altering the Specificity of Subtilisin *Baccillus lentus* Through the Introduction of Positive Charge at Single Amino Acid Sites", Bioorganic & Medicinal Chemistry, 1999, pp. 2303-2311.

M. Uchino; Kunio Suzuki; and Minoru Sekiya, "Nucleophilic Substitution of Alkyl (or Aryl) Imidomethyl Sulfones. A New Convenient Synthesis of Alkane (or Arene) sulfinates)", Chemical & Pharmaceutical Bulletin, 1978, 26(6), 1837-45.

Sandrinelli et al, "A New Reaction of 2-(Phenylsulfonyl)-3-phenyloxaziridine (Davis Reagent): Oxidation of Thiolates to Sulfinates. Application to Syntheis of Sulfones", Organic Letters (1999), 1(8), 1177-1180.

Hope, Eric G.; Kemmitt, Tim; and Levason, William, in Journal of the Chemical Society, Perkin Transactions 2: Physical Organic Chemistry (1972-1999) (1987), (4), 487-90.

W. A. Bonner, et al., "The Stereochemical Configureation of the Number One Carbon Atom in *b*-D-Xylopyranosylbenzene", J.Am. Chem. Soc. 1951, 73.

B. G. Davis, "Chemical Modification of Biocatalysts", Curr. Opin. Biotechnol. 2003, 14, 379.

R.J. Ferrier, R.H. Furneaux, "The Chemistry of Some 1-Mercury(II)Thio-D-Glucose Compounds"; A New Synthesis of 1-Thio Sugars, Carbohydr. Res. 1977, 57, 73.

J. Frgala, M. Cerny, J. Stanek, "Preparation of Alkyl 1-Thio-B-D-Galactopyranosides Substituated in The Alkyl With Reactive Groups", Collect. Czech. Chem. Commun. 1975, 40, 1411.

D. Horton, M.L. Wolfrom, "Thiosugars. I. Synthesis of Derivaties of 2-Amino-2-deoxy-1-thio-D-glucose", J. Org. Chem. 1962, 27, 1794.

W. M. zU Reckendorf, W. A. Bonner, "Sulfur Substituion Comounds of Amino Sugars. I 1-Thio-D-glucosamine", J Org. Chem. 1961, 26, 4596.

G. L. Ellman, K. D. Courtney, V. Andres, R. M. Feathersotne, "A New and Rapid Coloimetric Determination of Acetylcholinesterase Actvity", Biochem. Pharmacol. 1961, 7, 88.

C., Sato, R.; Goto, T.; Takikawa, Y.; Takizawa, "Convenient Syntheis of Aromatic Thiosulfonates From Aromatic Sulfinates With Elemental Sulfur in Amines", Synthesis 1980, 615.

Davis, B. G.; Ward, S. J., "Glycosyldisulfides: A New Class of Solution and Solid Phase Glycosyl Donors", Rendle, P. M. Chem. Commun. 2001, 189.

Ellman, G. L., "Tissue Sulfhydryl Groups", Arch. Biochem. Biophys. 1959, 82, 70.

* cited by examiner

REAGENTS AND METHODS FOR THE FORMATION OF DISULFIDE BONDS AND THE GLYCOSYLATION OF PROTEINS

CROSS-REFERENCE TO OTHER APPLICATIONS

This is a National Phase of International Application No. PCT/GB2004/002706, filed on Jun. 24, 2004, which claims priority from Great Britain Patent Application No. 0314743.6 filed on Jun. 24, 2003 and Great Britain Patent Application No. 0328884.2 filed on Dec. 12, 2003.

BACKGROUND OF THE INVENTION

The present application is concerned with reagents and methods for the formation of disulfide bonds and/or for the chemical modification of proteins, in particular reagents and methods for use in the glycosylation of proteins.

The co- and post-translational glycosylation of proteins plays a vital role in their biological behaviour and stability (R. Dwek, *Chem. Rev.*, 96:683-720 (1996)). For example, glycosylation plays a major role in essential biological processes such as cell signalling and regulation, development and immunity. The study of these events is made difficult by the fact that glycoproteins occur naturally as mixtures of so-called glycoforms that possess the same peptide backbone but differ in both the nature and the site of glycosylation. Furthermore, since protein glycosylation is not under direct genetic control, the expression of therapeutic glycoproteins in mammalian cell culture leads to heterogeneous mixtures of glycoforms. The ability to synthesise homogeneous glycoprotein glycoforms is therefore not only a prerequisite for accurate investigation purposes, but is of increasing importance when preparing therapeutic glycoproteins, which are currently marketed as multi-glycoform mixtures (e.g. erythropoietin and interleukins). Other post translational modifications of proteins, such as phosphorylation and methylation, are also of importance. Controlling the degree and nature of such modification of a protein therefore allows the possibility of investigating and controlling its behaviour in biological systems (B. G. Davis, Science, Vol 303, p 480-482, 2004).

A number of methods for the glycosylation of proteins are known, including chemical synthesis. Chemical synthesis of glycoproteins offers certain advantages, not least the possibility of access to pure glycoprotein glycoforms. One known synthetic method utilises thiol-selective carbohydrate reagents, glycosylmethane thiosulfonate reagents (glyco-MTS). Such glycosylmethane thiosulfonate reagents react with thiol groups in a protein to introduce a glycosyl residue linked to the protein via a disulfide bond (see for example WO00/01712).

However, glyco-MTS reagents suffer from a number of disadvantages, including occasionally moderate reaction yields, difficulties in their preparation and problems with stability under the basic conditions in which they are often used. There is therefore a need for further reagents for use in protein glycosylation which are readily prepared, stable and give high yields of the glycosylated protein product.

There is also a need for alternative methods for protein glycosylation which give high yields of the glycosylated protein product, are site-selective, and which allow glycosylation at both single and multiple sites in a wide range of different proteins.

DETAILED DESCRIPTION OF THE INVENTION

We have now surprisingly found that certain sulfur and selenium-containing glycosylation reagents are relatively straightforward to prepare, are generally more stable than the corresponding glyco-MTS reagents and can be used in the glycosylation of a wide range of thiol containing compounds, including proteins, in high yield.

In a first aspect, the invention therefore provides a method of forming disulfide bonds (—S—S—), the method comprising reacting an organic compound comprising at least one thiol group (—SH) with a compound of formula I:

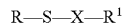

R—S—X—R¹        I wherein:

X denotes $SO_2$ or Se, prefereably Se;

R denotes an organic moiety, for example an alkyl group, an alkenyl group, an allynyl group, or a carbohydrate moiety; and $R^1$ denotes an optionally substituted alkyl group, an optionally substituted phenyl group, an optionally substituted pyridyl group or an optionally substituted naphthyl group;

with the proviso that when X denotes $SO_2$ then $R^1$ does not denote optionally substituted alkyl.

Preferably, the organic compound comprising at least one thiol group is an amino acid, peptide or protein.

In a second aspect, the invention further provides a method of chemically modifying a protein, peptide or amino acid comprising at least one thiol group (—SH), the method comprising reacting said protein, peptide or amino acid with a compound of formula I as previously defined.

In a still further aspect, the invention provides compounds of formula I wherein R denotes a carbohydrate moiety.

When R denotes an alkenyl or alkenyl group, there is the possibility that the disulphide compound formed by reaction with the compound of formula I may be further elaborated by reaction at the C=C or C≡C bond in the group R.

We have also surprisingly found that a thiol containing protein may be converted to the corresponding selenenylsulfide, and that the electrophilic character of the sulfur in the S—Se bond thus created renders it susceptible to nucleophilic substitution by thiol-containing compounds including carbohydrates.

In a third aspect, the invention therefore provides a method of chemically modifying a protein, peptide or amino acid comprising at least one thiol group (—S—H), the method comprising converting said thiol group into a selenenylsulfide group (—S—Se—$R^2$). The method therefore allows the preparation of a protein, peptide or amino acid comprising at least one selenenylsulfide group. Such proteins, peptides and amino acids comprising at least one selenenylsulfide group form a further feature of the invention. Particularly preferred are proteins or peptides comprising at least one selenenylsulfide group.

A selenenylsulfide group in a protein, peptide or amino acid may be further reacted with an organic compound comprising a thiol group to give further chemically modified proteins, peptides or amino acids in which the organic group is attached to the protein, peptide or amino acid via a disulfide bond. Preferably, the organic compound containing the thiol group is a carbohydrate compound, thus providing a method for the glycosylation of an amino acid, peptide or protein. As used herein, "glycosylation" refers to the general process of addition of a glycosyl unit to another moiety via a covalent linkage.

In a fourth aspect, the invention therefore provides a method of chemically modifying a protein, peptide or amino acid comprising at least one thiol group (—S—H), the method comprising:

(a) converting said thiol group into a selenenylsulfide group (—S—Se—$R^2$); and (b) reacting said selenenylsulfide group with an organic compound containing a thiol group.

The method(s) according to the first, second, third and fourth aspects of the invention will hereinafter be referred to as the first method, the second method, the third method and the fourth method respectively. Unless otherwise stated, all preferred features and definitions herein relate to all these methods. Furthermore, the present invention includes any and all possible combinations of any preferred features referred to herein, whether or not such combinations are specifically disclosed.

A generalised reaction scheme for disulfide bond formation according to the first and second methods is shown in Scheme 1:

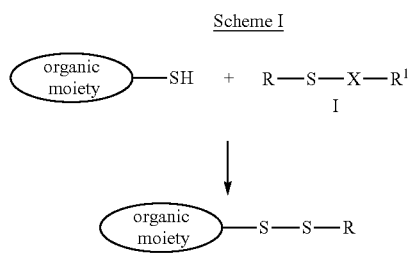

Scheme I

Preferably, the organic moiety shown in Scheme 1 is a protein, peptide or amino acid.

A generalised reaction scheme for the introduction of a selenenylsulfide group into a protein, peptide or amino acid according to the third and fourth methods is shown in Scheme 2:

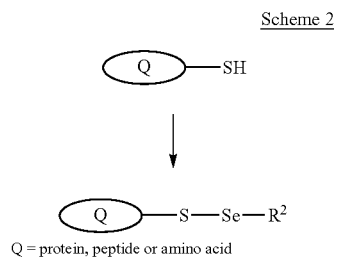

Scheme 2

Q = protein, peptide or amino acid

The method of Scheme 2 results in covalent linkage of a group $R^2$ to the protein, peptide or amino acid via a selenenylsulfide (—S—Se—) linkage. Such proteins, peptides or amino acids form a further feature of the invention.

Proteins and peptides comprising a selenenylsulfide group may be useful in the determination of protein structure via X-ray diffraction techniques. Currently, MAD (multiple wavelength anomalous dispersion) techniques involve the conversion of any methionine residues in the protein into selenomethionine. Comparison of the X-ray diffraction patterns of the modified and unmodified proteins then allows a determination of the structure of the unmodified protein to be carried out. The method of the invention allows convenient and ready access to alternative selenium-containing proteins or peptides which may be used in such techniques. The methods of the invention provide an easy method for introducing a heavy metal into a protein structure, thus making interpretation of the X-ray diffraction data easier.

Selenenylsulfide containing proteins, peptides or amino acids may be further reacted with thiol containing organic compounds according to the fourth method as shown in the generalised reaction scheme in Scheme 3:

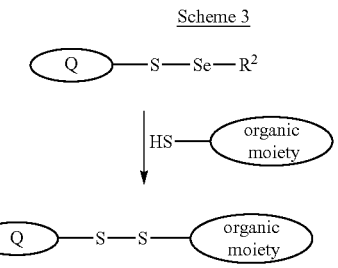

Scheme 3

Q = protein, peptide or amino acid

The method of Scheme 3 results in covalent linkage of the organic moiety to the protein, peptide or amino acid via a disulfide bond (—S—S—). In this method the protein, peptide or amino acid is acting as an electrophile whilst the thiol-containing organic compound acts as a nucleophile. In contrast, the known reactions utilising glyco-MTS reagents involve reaction of a nucleophilic thiol group in the protein, peptide or amino acid with the electrophilic glyco-MTS reagent. The method of the invention therefore provides a complementary strategy to the known protein modification strategies utilising glyco-MTS reagents.

As used herein, alkyl preferably denotes a straight chain or branched alkyl group containing 1-10 carbon atoms, preferably 1-6 carbon atoms. Preferred alkyl groups include methyl and ethyl. As used herein, alkenyl preferably denotes a straight chain or branched hydrocarbon group comprising at least one carbon-carbon double bond, and containing 2-20 carbon atoms, preferably 2-10 carbon atoms, and more preferably 2-6 carbon atoms. Preferred alkenyl groups include —(CH$_2$)CH=CH$_2$, —CH$_2$CH$_2$CH=CH$_2$, prenyl ((CH$_3$)$_2$C=CHCH$_2$—) and farnesyl ((CH$_3$)$_2$C=CH[CH$_2$CH$_2$C(CH$_3$)=CH]$_2$CH$_2$—). As used herein, alkynyl preferably denotes a straight chain or branched hydrocarbon group comprising at least one carbon-carbon triple bond, and containing 2-10 carbon atoms, preferably 2-6 carbon atoms. Preferred alkynyl groups include —CH$_2$C≡CH and —CH$_2$CH$_2$C≡CH.

When $R^1$ denotes an optionally substituted moiety, suitable substituents include any substituents which do not interfere with the formation of the compound of formula I or with the disulfide bond forming reaction according to the first or second methods, for example —NO$_2$, —SO$_3$H, —CO$_2$H, —(CH$_2$CH$_2$O)$_n$H and —(CH$_2$CH$_2$O)$_n$Me wherein n denotes 1-100, preferably 1-50, more preferably 1-20, and still more preferably 1-10. The $R^1$ group may be independently substituted by 1-5, and preferably 1 or 2, substituents. The $R^1$ group may also optionally be attached to, or form part of, a solid support, for example a resin such as a polystyrene resin.

A preferred $R^1$ group is phenyl. When the group $R^1$ in the compounds of formula I is phenyl or another aromatic group, then there is the added advantage that the progress of the reaction with the thiol-containing compound according to the first and second methods may be monitored using UV spectroscopy. Thus, for example, the PhSO$_2$-chromophore displays a maximum in the UV spectrum at approx. 265 nm. The PhSO$_2$-moiety is present in both the compound of formula I and the PhSO$_2^-$ that is the by-product of the disulfide bond forming reaction, but the associated extinction coefficients differ sufficiently for the progress of the reaction to be monitored using UV. Similarly, the third and fourth methods of the invention may be monitored by UV spectroscopy when the group $R^2$ is phenyl or another aromatic group.

In the compounds of formula I, the group R may be any organic moiety, particularly any organic moiety which is suitable for linkage to a protein, peptide or amino acid. There is no particular limitation on the nature of R. For example, the —S—X— group may be primary, secondary or tertiary. R may be aromatic or aliphatic. The group R may optionally be substituted, for example by phosphoryl or sulfonyl substituents. When X is Se, R may also be a protein, peptide or amino acid, giving the possibility of linking one protein, peptide or amino acid to another protein, peptide or amino acid via a disulphide linkage.

One preferred R group is farnesyl. Farnesylation is a natural post translational modification associated with many proteins, including the oncagenic protein Ras. The methods of the invention therefore allow prepation of farnesylated proteins, peptides and amino acids.

Also preferably, R is a carbohydrate moiety, optionally attached via a linker to the —S—X— group. The linker may contain 1 to 10 atoms between the carbohydrate moiety and the —S—X— group. For example, the linker may be an alkylene group (for example a —(CH$_2$)$_t$— group wherein t denotes 1 to 10), or an alkenylene group (for example a —(CH$_2$)CH=CH— or —CH$_2$CH$_2$CH=CH— group). Preferred are compounds in which the —S—X— group is at the anomeric position of a saccharide residue or is attached to the anomeric carbon via a linker.

Suitable carbohydrate moieties include monosaccharides, oligosaccharides and polysaccharides, and include any carbohydrate moiety which is present in naturally occurring glycoproteins or in biological systems. Preferred are optionally protected glycosyl or glycoside derivatives, for example optionally-protected glucosyl, glucoside, galactosyl or galactoside derivatives. Glycosyl and glycoside groups include both α and β groups. Suitable carbohydrate moieties include glucose, galactose, fucose, GlcNAc, GalNAc, sialic acid, and mannose, and oligosaccharides or polysaccharides comprising at least one glucose, galactose, fucose, GlcNAc, GalNAc, sialic acid, and/or mannose residue.

Any functional groups in the carbohydrate moiety may optionally be protected using protecting groups known in the art (see for example Greene et al, "Protective groups in organic synthesis", 2nd Edition, Wiley, N.Y., 1991, the disclosure of which is hereby incorporated by reference). Suitable protecting groups for any —OH groups in the carbohydrate moiety include acetyl (Ac), benzyl (Bn), pivolyl (piv), silyl (for example tert-butyl dimethylsilyl (TBDMSi) and tert-butyldiphenylsilyl (TMDPSi)), acetals, ketals, and methoxymethyl (MOM). Any protecting groups may be removed before or after attachment of the carbohydrate moiety to the amino acid, peptide or protein.

Particularly preferred carbohydrate moieties include Glc (Ac)$_4$-β, Glc(Bn)$_4$β-, Gal(Ac)$_4$β-, Gal(Bn)$_4$β-, Glc(Ac)$_4$α ((1,4)Glc(Ac)$_3$α(1,4)Glc(Ac)$_4$β-, β-Glc, β-Gal, α-Man, α-Man(Ac)$_4$, Man(1,6)Manα-, Man(1,6)Man(1-3)Manα-, (Ac)$_4$Man(1-6)(Ac)$_4$Man(1-3)(AC)$_2$Manα-, -Et-β-Gal, -Et-β-Glc, Et-α-Glc, -Et-α-Man, -Et-Lac, -β-Glc(Ac)$_2$, -β-Glc (Ac)$_3$, -Et-α-Glc(Ac)$_2$, -Et-α-Glc(Ac)$_3$, -Et-α-Glc(Ac)$_4$, -Et-β-Glc(Ac)$_2$, -Et-β-Glc(Ac)$_3$, -Et-β-Glc(Ac)$_4$, -Et-α-Man (Ac)$_3$, -Et-α-Man(Ac)$_4$, -Et-β-Gal(Ac)$_3$, -Et-β-Gal(Ac)$_4$, -Et-Lac(Ac)$_5$, -Et-Lac(Ac)$_6$, -Et-Lac(Ac)$_7$, and their deprotected equivalents.

Preferably, any saccharide units making up the carbohydrate moiety which are derived from naturally occurring sugars will each be in the naturally occurring enantiomeric form, which may be either the D-form (e.g. D-glucose or D-galactose), or the L-form (e.g. L-rhamnose or L-fucose). Any anomeric linkages may be α- or β-linkages.

The compound comprising a thiol group used in the first or second methods may be any organic compound which comprises at least one thiol group. The thiol group may be primary, secondary or tertiary. The compound may be aromatic or aliphatic. If more than one thiol group is present in the compound, a disulfide bond will potentially be formed at each such thiol group.

Preferably, the compound is an amino acid, a peptide or a protein. As used herein, a peptide contains a minimum of two amino acid residues linked together via an amide bond. Any amino acid comprised in the protein, peptide or amino acid is preferably an α-amino acid. Any amino acid may be in the D- or L-form, preferably the L-form. The amino acid, peptide or protein may be any naturally -occurring amino acid, peptide or protein which comprises a thiol group, for example due to the presence of one or more cysteine residues. Alternatively, the amino acid, peptide or protein may be prepared by chemical modification of a precursor non-thiol containing amino acid, peptide or protein. Alternatively, a thiol containing peptide or protein may be prepared via site-directed mutagenesis to introduce a cysteine residue. Site-directed mutagenesis is a known technique in the art (see for example WP00/01712 and J. Sambrook et al, Molecular Cloning: A Laboratory Manual, 3rd Edition, Cold Springs Harbour Laboratory Press, 2001, the disclosures of which are hereby incorporated by reference).

Preferred proteins include enzymes, the selectivity of which may be modified by controlled glycosylation using the methods and reagents according to the invention, and therapeutic proteins. Other preferred proteins include serum albumins and other blood proteins, hormones, interferons, receptors, antibodies, interleukins and erythropoietin.

It has been found that the compounds of formula I are normally thiol-selective, and hence that the presence of other functional groups in the thiol-containing organic compound does not normally interfere with the reaction. However, any other functional groups may optionally be protected using any protecting groups known in the art which are stable under the reaction conditions.

The disulfide bond forming reaction in the first or second method is generally carried out in the presence of a buffer at neutral or basic pH (about pH 7 to about 9.5), with slightly basic pHs being preferred (about pH 8 to about 9). Suitable buffers include HEPES, CHES, MES and Tris. If the thiol-containing compound is a protein, peptide or amino acid, the pH should be such that little or no unwanted denaturation occurs during the reaction. Similarly, the reaction temperature should be selected to avoid any significant damage to any temperature sensitive compounds. For example, a reaction with a protein or peptide is preferably carried out at ambient temperature or below to avoid any denaturation. Aqueous or organic solvent systems may be used, with aqueous solvent systems being preferred for the reaction of proteins, amino acids or peptides to ensure their dissolution. The reaction is generally fairly quick, for example often taking less than 1 hour.

In general, an excess of the compound of formula I will be used, for example 10-20 equivalents based on the thiol-containing compound. In contrast, reactions with glyco-MTS reagents often require the use of approximately 30 equivalents, adding to the cost of the reagents.

It has been found that the compounds of formula I wherein R denotes a carbohydrate moiety, X denotes $SO_2$ and $R^1$ denotes phenyl are generally more stable to basic conditions than the corresponding glyco-MTS compounds. Any unreacted or excess compound of formula I may therefore often be recovered from the reaction for reuse, which is particularly advantageous when R denotes a carbohydrate moiety as such compounds may be relatively expensive and/or time consuming to prepare. Furthermore, the phenyl thiosulfonate compounds of formula I are generally cheaper and easier to prepare than the corresponding MTS compounds.

The compounds of formula I may be prepared by a number of different methods. Compounds wherein X denotes $SO_2$ maybe prepared by reacting a compound of formula II:

$$M(SSO_2R^1)_k \qquad\qquad II$$

wherein:

M denotes a metal, for example Li, Na, K, Cs, Ca, Mg, Zn, or Al, preferably Na or K; and k denotes 1, 2 or 3;

with a compound of formula III:

$$R-L \qquad\qquad III$$

wherein:

R is as defined for the compounds of formula I and L denotes a leaving group.

Any leaving group L may be utilised as long as the resultant anion $L^-$ does not unduly interfere with the reaction in any way, for example by reacting with the product. Preferred leaving groups L include halo and sulfonates such as toluenesulfonate (tosylate), methanesulfonate (mesylate) and trifluoromethane sulfonate (triflate), in particular chloro and bromo.

Compounds of formula III are commercially available or may be prepared using methods known in the art, for example methods for the formation of halo-sugars in general and 1-halo-sugars in particular. Preferably the compound of formula III is a glycosyl halide. Examples of suitable compounds of formula III based on glucose and galactose are shown generically below:

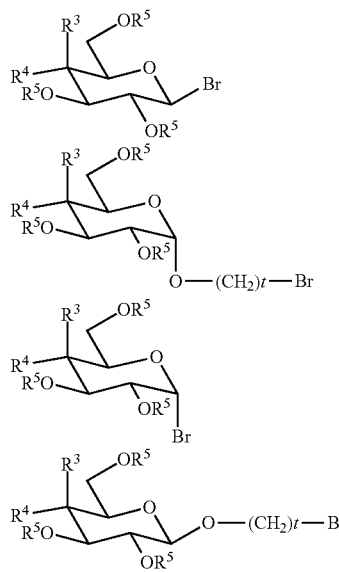

wherein:

each $R^5$ independently denotes H, a saccharide moiety, or a suitable protecting group for example Ac or Bn, preferably each $R_5$ denotes H;

one of $R^3$ and $R^4$ denotes H and the other denotes OH, O-protecting group or O-saccharide moiety, preferably H or O-saccharide moiety; and t denotes 1 to 10, preferably 1 to 6, more preferably 2 or 3.

The reaction may be carried out in any solvent-system in which the compound of formula III is soluble. Preferably, the compound of formula II is also at least partially soluble in the solvent system. Suitable solvents include alkanols such as ethanol and methanol, N,N-dimethylformamide (DMF) and acetonitrile, with acetonitrile being particularly preferred.

The compounds of formula II may be prepared by reacting the corresponding sulfinite salt (formula VII) with sulfur, as shown in Scheme 4:

Scheme 4

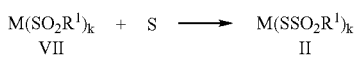

Compounds of formula II which are crystalline are preferred for ease of purification, especially on a large scale.

Sulfinite salts of formula VII are available commercially (for example sodium benzenesulfinite) or may be prepared by methods known in the art (see for example JP 61205249, and M. Uchino et al, Chemical & Pharmaceutical Bulletin, 1978, 26(6), 1837-45, the disclosures of which are hereby incorporated by reference). For example, the corresponding thiolate salt $R^1S-$ may be prepared by deprotonation of the corresponding thiol compound $R^1SH$ using a suitable base, for example methyl lithium. The thiolate salt may then be oxidised to the corresponding sulfinite salt using a suitable oxidising agent, for example 2-(phenylsulfonyl)-3-phenyloxaziridine (the "Davis reagent", Sandrinelli et al, Organic Letters (1999), 1(8), 1177-1180, the disclosure of which is hereby incorporated by reference).

Alternatively, compounds of formula I in which X denotes $SO_2$ may be prepared by reacting a disulfide of formula VIII with a sulfinite anion $R^1SO_2^-$ in the presence of silver ions, as shown in Scheme 5:

Scheme 5

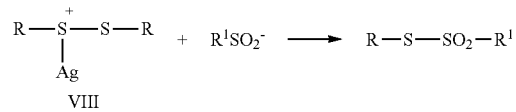

Disulfide compounds of formula VIII are commercially available or may be prepared using methods known in the art.

Compounds of formula I wherein X denotes Se may be formed by reaction of a compound of formula V:

$$R-SH \qquad\qquad V$$

wherein R is as defined for the compounds of formula I, with a compound of formula VIa or VIb:

$$R^1SeL^2 \qquad\qquad VIa$$

$$R^1Se(OH)_2 \qquad\qquad VIb$$

wherein $R^1$ is as defined for the compounds of formula I, and $L^2$ denotes a leaving group, for example OH, Br, Cl, CN, or I, preferably Br. The reaction may be carried out in anhydrous dichloromethane and then quenched by the addition of triethylamine. A preferred compound of formula IVa is PhSeBr and a preferred compound of formula VIb is PhSe(OH)$_2$.

The compounds of formula VI are commercially available (e.g. PhSeBr, PhSeCl, PhSeCN, 2-nitrophenyl selenocyanate) or may be prepared by methods known in the art. For example, MeSeBr may be prepared according to the method of Hope, Eric G.; Kemmitt, Tim; and Levason, William, in Journal of the Chemical Society, Perkin Transactions 2: Physical Organic Chemistry (1972-1999) (1987), (4), 487-90, the disclosure of which is hereby incorporated by reference.

Organic compounds containing at least one thiol group, including compounds of formula V, are commercially available or may be prepared using methods known in the art, for example methods for the preparation of thiol compounds in general, and thio-sugars in particular.

For example, thio sugars may be prepared from the corresponding halo sugars by treatment of the halo sugar with thiourea to afford the corresponding isothiouronium salt (W. A. Bonner, J. E. Kahn, *J. Am. Chem. Soc.* 1951, 73) followed by mild hydrolysis with sodium metabisulfite to give the corresponding thiol. If necessary, suitable protecting groups may be used during the synthesis of any thio-sugars. When R in the compound of formula V denotes a carbohydrate moiety, the thiol group may be at any position in the moiety. Preferably, it is at the anomeric position of a saccharide or is attached to the anomeric carbon via a linker.

Examples of suitable compounds of formula V based on glucose and galactose are shown generically below:

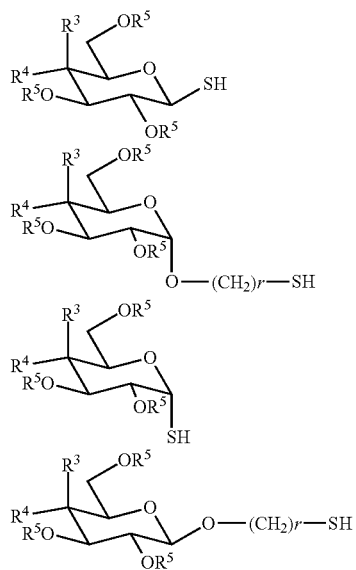

wherein:
each $R^5$ independently denotes H, a saccharide moiety, or a suitable protecting group, for example Ac or Bn, preferably each $R^5$ denotes H;
one of $R^3$ and $R^4$ denotes H and the other denotes OH, O-protecting group or O-saccharide moiety, preferably H or O-saccharide moiety; and
r denotes 2 to 10, preferably 2 to 6, more preferably 2 or 3.

Compounds of formula V are also suitable for use as the thiol containing compound in the fourth method of the invention.

In the reaction of the compounds of formula V with the compounds of formula VI, any other functional groups in the compound of formula V may be unprotected, or may be protected by protecting groups known in the art.

The conversion of the at least one thiol group in the protein, peptide or amino acid to a selenenylsulfide group according to the third or fourth method is highly selective. In addition, the reaction of the thiol containing organic compound with the selenenylsulfide group is highly site-selective. It is not therefore normally necessary for any other functional groups in the protein, peptide or amino acid or in the thiol containing organic compound to be protected whilst practising the methods of the invention. This can be highly advantageous, as it avoids the need for any subsequent deprotection steps to be carried out on the product.

If the protein, peptide or amino acid comprises more than one thiol group, then each such thiol group will potentially be converted to the corresponding selenenylsulfide group. Each such selenenylsulfide group may then potentially be reacted with a thiol containing organic compound, leading to attachment of the organic compound via a disulphide linkage to the protein, peptide or amino acid at multiple sites. The methods of the invention therefore provides a convenient method for the chemical modification of a protein, peptide or amino acid at multiple sites. In particular, the methods of the invention allows glycosylation of a protein, peptide or amino acid at multiple sites.

Conversion of the thiol group in the protein, peptide or amino acid to a selenenylsulfide group in the third or fourth methods is conveniently carried out by reacting said protein, peptide or amino acid with a compound of formula Xa or Xb:

wherein:
L denotes a leaving group, for example OH, Br, CN, Cl or I, preferably Br; and
$R^2$ denotes an optionally substituted alkyl group, an optionally substituted phenyl group, an optionally substituted benzyl group, an optionally substituted pyridyl group or an optionally substituted naphthyl group. A preferred $R^2$ group is phenyl, a preferred compound of formula Xa is PhSeBr and a preferred compound of formula Xb is PhSe(OH)$_2$.

When $R^2$ denotes an optionally substituted moiety, suitable substituents include any substituents which do not interfere with the reaction with the thiol containing protein, peptide or amino acid, and preferably also do not interfere with any subsequent reaction of the protein peptide or amino acid, for example reaction with a thiol containing organic compound. Suitable substituents include —NO$_2$, —SO$_3$H, —CO$_2$H, —(CH$_2$CH$_2$O)$_n$H, and —(CH$_2$CH$_2$O)$_n$Me wherein n denotes 1-100, preferably 1-50, more preferably 1-20, and still more preferably 1-10. The $R^2$ group may be independently substituted by 1-5, and preferably 1 or 2, substituents.

The $R^2$ group may also optionally be attached to, or form part of, a solid support. For example, the compound of formula Xa or Xb may be derived from a resin such as a polystyrene resin, as shown below:

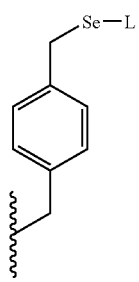

The compounds of formula Xa and Xb are commercially available or may be prepared by methods known in the art, as discussed previously for the compounds of formula VIa and VIb.

At least one mol equivalent of the compound of formula Xa or Xb per thiol group in the protein, peptide or amino acid should be used, to ensure conversion of each such thiol group to the corresponding selenenylsulfide group. The reaction is preferably carried out in an aqueous solvent (such as a mixture of water and acetonitrile) in the presence of a buffer (for example MES, pH 9.5). The pH and temperature of the reaction should be chosen such that undesirable denaturation of the protein or peptide is avoided. Preferably, the reaction is carried out at room temperature or below, at a slightly basic pH (e.g. about pH 8 to about pH 9.5).

The organic compound containing a thiol group may be any organic compound which is suitable for linkage to a protein, peptide or amino acid, and in which the sulfur atom of the thiol group can act as a nucleophile to react with a selenenylsulfide group. There is no particular limitation on the nature of the organic compound. For example, the thiol group may be primary, secondary or tertiary. The compound may be aromatic or aliphatic. For example, the compound may be an alkyl, alkenyl (e.g. farnesyl) or alkynyl thiol. Preferably, the compound only contains one thiol group.

Suitable organic moieties for attachment to a protein, peptide or amino acid include any group which may be useful in modifying the physical or chemical properties of the protein, peptide or amino acid. Suitable moieties include labels (for example fluorescent labels) or groups to aid the stability, processing or solubility of the protein, peptide or amino acid. The organic compound may also be a second protein, peptide or amino acid, giving the possibility of linking one protein, peptide or amino acid to another protein, peptide or amino acid via a disulphide linkage using the methods of the invention.

Preferably, the organic compound containing at least one thiol group is a farnesyl derivative, or is a carbohydrate moiety as previously defined, optionally attached via a linker to the thiol (—S—H) group. The linker may contain 1 to 10 atoms between the carbohydrate moiety and the —SH group. For example, the linker may be an alkylene group (for example a —$(CH_2)_t$— group wherein t denotes 1 to 10), or an alkenylene group (for example a —$(CH_2)$CH═CH— or —$CH_2CH_2$CH═CH— group). Preferred are compounds in which the thiol group is at the anomeric position of a saccharide residue or is attached to the anomeric carbon via a linker.

Any functional groups in the carbohydrate moiety may optionally be protected using protecting groups known in the art as discussed previously. Any protecting groups may be removed before or after attachment of the carbohydrate moiety to the amino acid, peptide or protein. Preferably, they are removed before reaction with the selenenylsulfide compound, to remove the need for any post-linkage deprotection steps. A further advantage of the glycosylation method of the invention is that it allows for the linkage of unprotected carbohydrate moieties to an amino acid, peptide or protein.

The reaction of the selenenylsulfide group with the organic compound containing a thiol group according to the fourth method (i.e. the disulfide bond forming reaction) is generally carried out in the presence of a buffer at neutral or basic pH (e.g. about pH 7 to about pH 9.5), with slightly basic pHs being preferred (e.g. about pH 8 to about pH 9). Suitable buffers include HEPES, CHES, MES and Tris. The pH should be such that little or no unwanted denaturation of the protein or peptide occurs during the reaction. Similarly, the reaction temperature should be selected to avoid any significant damage to any temperature sensitive compounds. For example, a reaction with a protein or peptide is preferably carried out at ambient temperature or below to avoid any denaturation. Aqueous or organic solvent systems may be used, with aqueous solvent systems being preferred to ensure the dissolution of the protein, amino acid or peptide. Aqueous solvent systems are also preferred as they allow the use of unprotected carbohydrate compounds as the organic compound. The reaction is generally fairly quick, for example often taking less than 1 hour.

In general, an excess of the organic compound containing at least one thiol group will be used, for example 10-20 equivalents based on the protein, amino acid or peptide. However, as little as 1 mol equivalent may be used in some cases. Carbohydrate compounds may be expensive and time-consuming to obtain in large quantities. Therefore, when the organic compound containing at least one thiol group is a carbohydrate compound, for reasons of economy it is desirable to use the minimum possible number of equivalents. Prior art methods for protein glycosylation often require use of a very large excess of the carbohydrate compound, for example often of the order of 1000 equivalents (B. G. Davis, Curr. Opin. Biotechnol. 2003, 14, 379). The method of the invention therefore advantageously allows use of fewer equivalents of the glycosyl compound than the prior art methods.

The invention will be further illustrated by the following non-limiting Examples.

General Experimental

Melting points were recorded on a Kofler hot block and are uncorrected. Proton nuclear magnetic resonance ($\delta_H$) spectra 400 MHz spectra were assigned using COSY. Carbon nuclear magnetic resonance ($\delta_C$) spectra were assigned using HMQC. Multiplicities were assigned using DEPT sequence. All chemical shifts are quoted on the δ scale in ppm using residual solvent as the internal standard.

Infrared spectra adsorption maxima were recorded in wavenumbers (cm$^{-1}$) and classified as s (strong) and br (broad). Low resolution mass spectra were recorded using electrospray ionisation (ESI), or using chemical ionization (NH$_3$, CI) techniques as stated. High resolution mass spectra were recorded using chemical ionization (NH$_3$, CI) techniques, or using electrospray ionization (NH$_3$, CI) techniques, or using field ionisation (FI+) as stated. M/z values are reported in Daltons and are followed by their percentage abundance in parentheses.

Optical rotations were measured on a polarimeter with a path length of 1 dm Concentrations are given in g/100 mL.

Thin layer chromatography (t.l.c) was carried out on Merck Kieselgel 60F$_{254}$ pre-coated glassbacked plates. Visulation of the plates was achieved using a UV lamp ($\lambda_{max}$=254 or 365 nm), and/or ammonium molybdate (5% in 2M H$_2$SO$_4$) or sulfuric acid (5% in EtOH). Flash column chromatography was carried out using Sorbsil C60 40/60 silica. Dichloromethane (DCM) was distilled from calcium hydride. Acetone was distilled from anhydrous calcium sulfate. Remaining anhydrous solvents were purchased from Fluka 'Petrol' refers to the fraction of petroleum ether boiling in the range 40-60° C.

Protein Mass spectrometry: Liquid chromatography/mass spectrometry was performed on a Micromass LCT (ESI-TOF-MS) coupled to a Waters Alliance 2790 HPLC using a Phenomenex Jupiter C5 column (150×2.1 mm×5 µm). Water (solvent A) and acetonitrile (solvent B), each containing 0.5% formic acid, were used as the mobile phase at a flow rate of 0.2 ml min$^{-1}$. The gradient was programmed as follows: 95% A (3 min isocratic) to 100% B after 16 min then isocratic for 2 min. The electrospray source of the LCT was operated with a capillary voltage of 3 kV and a cone voltage of 30 V. Nitrogen was used as the nebuliser and desolvation gas at a total flow of 400 l hr$^{-1}$. Myoglobin (horse heart) was used as a calibration standard and to test the sensitivity of the system.

EXAMPLE 1

(2,3,4,6-Tetra-O-acetyl-β-D-glucopyranosyl)-1-isothiouronium bromide

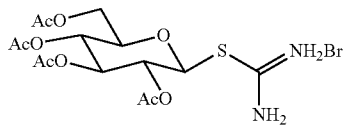

2,3,4,6-Tetra-O-acetyl-α-D-glucopyranosyl bromide (11.0 g, 26.4 mmol) and thiourea (3.10 g, 41.9 mmol) were dissolved in anhydrous acetone (30 mL) under argon and heated to 60° C. After 20 min a white solid precipitated. The precipitate was removed by filtration, the filtrate was returned to reflux, this process was repeated until the solid ceased to precipitate. The off-white crystals were combined and recrystallised from acetone/petrol to afford the title compound (11.4 g, 76%) as a white crystalline solid mp 194-196° C. [Lit. 191° C. (H. Beyer, U. Schultz, Chem. Ber. 1954, 87, 78)]; $[\alpha]_D^{25}$-5.6(c, 1.0 in H$_2$O) [Lit. $[\alpha]_D^{25}$-7.6(c, 1.4 in H$_2$O) (W. A. Bonner, J. B. Kahn, J Am Chem Soc, 1951, 73, 2241)]; $\delta_H$(400 MHz, DMSO-$_6$) 1.97, 2.00, 2.02, 2.06 (12H, 4×s, 4×CH$_3$), 4.06-4.25 (3H, m, H-5, H-6, H-6'), 5.07-5.12 (2H, m, H-2, H-4), 5.31 (1H, at, J9.5 Hz, H-3), 5.77 (1H, d, J$_{1,2}$ 9.9 Hz, H-1), 9.13 (2H, brs, NH$_2$), 9.29 (2H brs, NH$_2$).

EXAMPLE 2

1-Thio-2,3,4,6-tetra-O-acetyl-β-D-glucopyranose

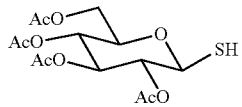 [SMILES: CC(=O)OCC1OC(S)C(OC(C)=O)C(OC(C)=O)C1OC(C)=O]

(2,3,4,6-Tetra-O-acetyl-β-glucopyranosyl)-1-isothiouronium bromide (9.0 g, 18.8 mmol) and Na$_2$S$_2$O$_5$ (4.93 g, 26.0 mmol) were added to a stirred mixture of DCM (1560 mL) and water (70 mL). The mixture was heated to reflux under argon. After 1.5 h the reaction was cooled to room temperature (RT) and the phases were separated. The aqueous layer was re-extracted with DCM (3×50 mL). The combined organic layers were washed with water (50 mL), dried over MgSO$_4$, filtered and the solvent removed in vacuo to afford the title compound (6.14 g, 90%) as a white solid, mp 112-114° C. [Lit. 113-114° C. (R. J. Ferrier, R. H. Furneaux, Carbohydr. Res. 1977, 57, 73)]; $[\alpha]_D^{24}$+6.3 (c, 1.2 in CHCl$_3$) [Lit. $[\alpha]_D^{20}$+5.0 (c, 1.1 in CHCl$_3$) (R. J. Ferrier, R. H. Furneaux, Carbohydr. Res. 1977, 57, 73)]; $\delta_H$(400 MHz, CDCl$_3$) 1.99, 2.00, 2.05, 2.06 (12H, 4×s, 4×CH$_3$), 2.30 (1H, d, J$_{1,SH}$ 10.2 Hz, SH), 3.71 (1H, ddd, J$_{4,5}$ 10.0 Hz, J$_{5,6}$ 2.4 Hz, J$_{5,6'}$ 4.7 Hz, H-5), 4.10 (1H, dd, J$_{6,6'}$12.3 Hz, H-6), 4.22 (1H, dd, H-6'), 4.53 (1H, at, J9.9 Hz, H-1), 4.95 (1H, at, J9.5 Hz, H-2), 5.08 (1H, at, J9.8 Hz, H-4), 5.17 (1H, at, J9.4 Hz, H-3).

EXAMPLE 3

(2,3,4,6-Tetra-O-acetyl-β-D-galactopyranosyl)-1-isothiouronium bromide

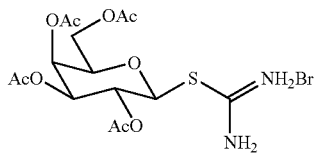

2,3,4,6-Tetra-O-acetyl-D-$_β$-galactopyranosyl bromide (5.4 g, 13.0 mmol) and thiourea (1.25 g, 16.8 mmol) were dissolved in anhydrous acetone (40 mL) under argon and heated to 60° C. After 1 h the reaction was allowed to cool to room temperature and the resulting residue was filtered and recrystallised from acetone/petrol to afford the title compound (4.6 g, 70%, 2 steps) as a white crystalline solid mp 134-137° C. [Lit. 170° C. from isopropanol (W. A. Bonner, J. E. Kahn, J Am Chem Soc 1951, 73, 2241)]; $[\alpha]_D^{25}$+40.4 (c, 1.0 in H$_2$O) [Lit. $[\alpha]_D^{25}$+16.0 (c, 1.6 in EtOH, (W. A. Bonner, J. E. Kahn, J Am Chem Soc 1951, 73, 2241)); $\delta_H$ (500 MHz, DMSO-d$_6$) 1.96, 2.02, 2.09, 2.15 (12H, 4×s, 4×CH$_3$) 4.06-4.13 (2H, m, H-6, H-6'), 4.45 (1H, t, J6.2 Hz, H-5), 5.12 (1H, at, J9.9 Hz, H-2), 5.24(1H, dd, J$_{2,3}$ 10.0 Hz, J$_{3,4}$ 3.6 Hz, H-3), 5.39 (1H, d, J$_{3,4}$ 3.1 Hz, H-4), 5.71 (1H, d, J$_{1,2}$ 10.2 Hz, H-1), 9.12, 9.36 (2×2H, 2×brs, 2×NH$_2$).

EXAMPLE 4

1-Thio-2,3,4,6-tetra-O-acetyl-$_β$-D-galactopyranose

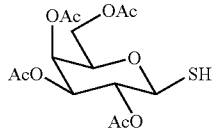

(2,3,4,6-Tetra-O-acetyl-$_β$-D-galactopyranosyl)-1-isothiouronium bromide (4.4 g, 8.8 mmol) and Na$_2$S$_2$O$_5$ (2.02 g, 10.6 mmol) were added to a stirred mixture of DCM (60 mL) and water (30 mL). The mixture was heated to reflux under argon. After 2.5 h the reaction was cooled to RT and the phases were separated. The aqueous layer was re-extracted with DCM (3×50 mL). The combined organic layers were washed with water (100 mL), brine (100 mL), dried over MgSO$_4$, filtered and the solvent removed in vacuo to afford the title compound (2.65 g, 81%) as a white solid, mp 83-84° C. [Lit. 86.5-88° C. (J. Frgala, M. Cerny, J. Stanek, *Collect. Czech. Chem. Commun.* 1975, 40, 1411)]; $[\alpha]_D^{24}$+30.1 (c, 1.0 in CHCl$_3$) [Lit. $[\alpha]_D^{19}$+32.0 (c, 3.5 in CHCl$_3$) (J. Frgala, M. Cerny, J. Stanek, *Collect. Czech. Chem. Commun.* 1975, 40, 1411)]; $\delta_H$ (400 MHz, CDCl$_3$) 1.99, 2.06, 2.10, 2.17 (12H, 4×s, 4×CH$_3$), 2.38 (1H, d, J$_{1,SH}$ 10.3 Hz, SH), 3.95 (1H, dt, J$_{4,5}$ 1.2 Hz, J$_{5,6}$ 6.6 Hz, J$_{5,6'}$ 6.6 Hz, H-5), 4.09-4.14 (2H, m, H-6, H-6'), 4.53 (1H, at, J9.9 Hz, H-1), 5.02 (1H, dd, J$_{2,3}$ 10.1, J$_{3,4}$ 3.4 Hz, H-3), 5.19 (1H, at, J10.0 Hz, H-2), 5.44 (1H, at, dd, J$_{3,4}$ 3.7 Hz, J$_{4,5}$ 1.2 Hz, H-4).

EXAMPLE 5

(3,4,6-Tri-O-acetyl-2-acetamido-2-deoxy-β-D-glucopyranosyl)-1-isothiouronium chloride

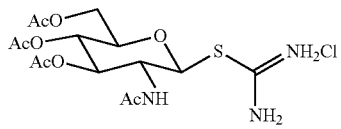

3,4,6-Tri-O-acetyl-2-acetamido-2-deoxy-α-D-glucopyranosoyl chloride (3.0 g, 8.2 mmol) and thiourea (1.21 g, 14.6 mmol) were dissolved in anhydrous acetone (25 mL) under argon and heated to 60° C. After 2 h a white solid precipitated. The precipitate was removed by filtration, the filtrate was returned to reflux, this process was repeated until the solid ceased to precipitate. The off white crystals were combined and recrystallised from acetone/petrol to afford (the title compound (2.19 g, 61%) as a white crystalline solid mp 134-137° C. [Lit. 179-181° C. from EtOH (D. Horton, M. L. Wolfrom, *J. Org. Chem.* 1962, 27, 1794)]; $[\alpha]_D^{25}$-25.2 (c, 1.0 in H$_2$O) [Lit. $[\alpha]_D^{25}$-29.3 (c, 1.1 in MeOH) (D. Horton, M. L. Wolfrom, *J. Org. Chem.* 1962, 27, 1794)]; $\delta_H$(400 MHz, DMSO-d$_6$) 1.80 (3H, s, NHCOCH$_3$), 1.94, 1.98, 2.08 (9H, 3×s, 3×CH$_3$), 4.05 (1H, dd, J$_{5,6}$ 2.4 Hz, J$_{6,6'}$ 12.4 Hz, H-6), 4.17 (1H, dd, J$_{5,6'}$5.0 Hz, J$_{6,6'}$ 12.3 Hz, H-6'), 4.26 (1H, ddd, J$_{4,5}$ 10.2 Hz, J$_{5,6}$ 2.3 Hz, J$_{5,6'}$4.7 Hz, H-5), 4.93 (1H, at, J9.9 Hz, H-4), 5.12 (1H, at, J9.9 Hz, H-3), 5.73 (1H, d, J$_{1,2}$ 10.4 Hz, H-1), 8.48 (1H, d, J4.7 Hz, NHAc), 9.13 (2H, brs, NH$_2$), 9.29 (2H, brs, NH$_2$).

EXAMPLE 6

1-Thio-3,4,6-tri-O-acetyl-2-acetamido-2-deoxy-β-D-glucopyranose

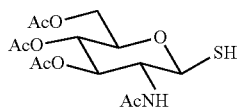

(3,4,6-Tri-O-acetyl-2-acetamido-2-deoxy-β-D-glucopyranosyl)-1-isothiouronium chloride (1.75 g, 39.8 mmol) and Na$_2$S$_2$O$_5$ (0.91 g, 4.8 mmol) were added to a stirred mixture of DCM (30 mL) and water (15 mL). The mixture was heated to reflux under argon. After 2 h the reaction was cooled to RT and the phases were separated. The aqueous layer was re-extracted with DCM (2×50 mL). The combined organic layers were washed with water (50 mL), brine (50 mL), dried over MgSO$_4$, filtered and the solvent removed in vacuo. Recrystallization from EtOAc/petrol afforded the title compound (1.00 g, 68%) as a white solid, mp 165-167° C. [Lit. 167-168° C. (W. M. zu Reckendorf, W. A. Bonner, *J Org. Chem.* 1961, 26, 4596)]; $[\alpha]_D^{25}$-24.8 (c, 1.0 in CHCl$_3$) [Lit. $[\alpha]_D^{25}$-14.5 (c, 0.9 in CHCl$_3$) (W. M. zu Reckendorf, W. A. Bonner, *J. Org. Chem.* 1961, 26, 4596)]; $\delta_H$ (400 MHz, CDCl$_3$) 1.99, 2.03, 2.05, 2.10 (12H, 4×s, 4×CH$_3$), 2.57 (1H, d, J$_{1,SH}$ 9.2 Hz, SH), 3.67 (1H, ddd, J$_{4,5}$ 9.7 Hz, J$_{5,6}$ 4.8 Hz, J$_{5,6'}$ 2.3 Hz, H-5), 4.09-4.17 (2H, m, H-2, H-3), 4.24 (1H, dd, J$_{5,6}$ 4.8 Hz, J$_{6,6'}$ 12.4 Hz, H-6), 4.59 (1H, at, J9.8 Hz, H-1), 5.06-5.15 (2H, m, H-4, H-6'), 5.72 (1H, d, J9.2 Hz, NH).

EXAMPLE 7

1-Thio-β-D-galactopyranose

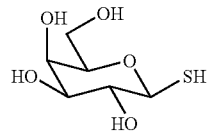 [SMILES: OCC1OC(S)C(O)C(O)C1O]

1-Thio-2,3,4,6-tetra-O-acetyl-β-D-galactopyranose (3.00 g, 7.3 mmol) and NaOMe (40 mg, 0.73 mmol) were added to a stirred solution of MeOH (40 ml). After 2 h, t.l.c. (EtOAc/petrol 1:1) indicated the formation of a product (R$_f$ 0.0) with complete consumption of the starting material (R$_f$ 0.5). The reaction was neutralised with the addition of Dowex®-50 ion exchange resin after which point the reaction was filtered and concentrated in vacuo. Recrystallization from MeOH/EtOAc afforded the title compound (1.41 g, 98%) as a white crystalline solid m.p. 100-102° C.; $[\alpha]_D^{22}$+47.6 (c, 1.0 in MeOH; $\delta_H$ (400 MHz, CD$_3$OD), 2.62 (1H, d, J$_{1,SH}$ 8.3 Hz, SH), 3.47-3.49 (2H, m, H-2, H-3), 3.57 (1H, at, J5.9 Hz, H-5), 3.68 (1H, dd, J$_{5,6}$ 5.0 Hz, J$_{6,6'}$ 11.4 Hz, H-6), 3.75 (1H, dd, J$_{5,6'}$ 6.9 Hz, J$_{6,6'}$ 11.5 Hz, H-6'), 3.91 (1H, bs, H-4), 4.37 (1H, bd, J7.7 Hz, H-1); $\delta_C$ (100 MHz, CD$_3$OD), 61.6 (t, C-6), 69.6 (d, C-4), 74.4, 74.8 (2×d, C-2, C-3), 80.1 (d, C-5), 81.4 (d, C-1); m/z (ES-) 196(100%, M-H$^+$); m/z HRMS (ES-) Calcd. for C$_6$H$_{12}$O$_5$S (M-H$^+$) 195.0327. Found 195.0323.

EXAMPLE 8

1-Thio-2-acetamido-2-deoxy-β-D-glucopyranose

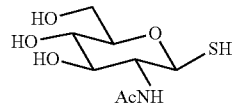

3,4,6-Tri-O-acetyl-2-acetylamino-2-deoxy-β-D-glucopyranosyl thiol (400 mg, 0.98 mmol) and sodium methoxide (18 mg, 0.3 mmol) were added to a stirred solution of methanol (10 ml). After a 30 min period, t.l.c. (ethyl acetate) indicated the formation of a product ($R_f$ 0.0) with complete consumption of the starting material ($R_f$ 0.2). The reaction was neutralised with the addition of Dowex®-50 ion exchange resin after which point the reaction was filtered and concentrated in vacuo. Recrystallisation from methanol/ethyl acetate afforded the title product (230 mg, 98%) as a white crystalline solid; m.p. 85-88° C. [Lit. 86-88° C.]$^{18}$; $[\alpha]_D^{22}$ -10.4 (c, 1.0 in MeOH) [Lit. $[\alpha]_D^{25}$ +177.1 (c, 1.45 in CHCl$_3$)]$^{18}$; $\delta_H$(400 MHz, MeOH), 2.00 (3H, s, CH$_3$), 3.27-3.37 (2H, m, H-4, H-5), 3.42 (1H, at J9.1 Hz, H-3), 3.64-3.73 (2H, m, H-2, H-6), 3.87 (1H, dd, $J_{5,6}$ 2.1 Hz, $J_{6,6'}$ 12.0 Hz, H-6'), 4.56 (1H, d, $J_{1,2}$ 10.0 Hz, H-1), 8.11 (1H, bd, $J_{NH,2}$ 9.1 Hz, NH).

EXAMPLE 9

1,2,3,6-tetra-O-acetyl-4-O-(2,3,6-tri-O-acetyl-4-O-(2,3,4,6-tetra-O-acetyl-$\alpha$-O-glucopyranosyl)-$\alpha$-D-glucopyranosyl)-D-glucopyranose

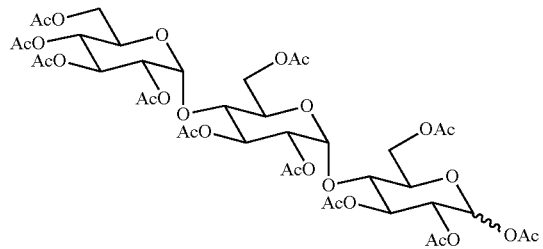 [SMILES: CC(=O)OCC1OC(OC2C(COC(C)=O)OC(OC3C(COC(C)=O)OC(OC(C)=O)C(OC(C)=O)C3OC(C)=O)C(OC(C)=O)C2OC(C)=O)C(OC(C)=O)C(OC(C)=O)C1OC(C)=O]

Sodium acetate (700 mg, 8.3 mmol) was added to acetic anhydride (50 mL) and heated to reflux, at which point maltotriose (3.00 g, 6.0 mmol) was added and stirred vigorously. After 90 min, t.l.c. (petrol:ethyl acetate, 1:2) indicated the formation of a product ($R_f$ 0.3) with complete consumption of the starting material ($R_f$ 0.0). The reaction was allowed to cool to RT and diluted with DCM (50 mL) and partitioned with water (100 mL). The phases were separated and the aqueous layer was re-extracted with DCM (2×50 mL). The combined organic layers were washed with sodium hydrogen carbonate (400 mL of a saturated aqueous solution) until pH 8 was obtained, brine (200 mL), dried (MgSO$_4$), filtered and concentrated in vacuo to afford the title product as a mixture of anomers ($\alpha/\beta$, 2/11) as an amorphous white solid; for $\beta$ compound: $\delta_H$(500 MHz, CDCl$_3$) 2.05, 2.07, 2.10, 2.14, 2.15, 2.19, 2.21, 2.27 (30H, 8×s, 10×OAc), 3.92 (1H, ddd, $J_{4,5}$ 9.5 Hz, $J_{5,6}$ 2.9 Hz, $J_{6,6'}$ 4.1 Hz, H-5a), 3.95-4.01 (3H, m, H-4b, H-5b, H-5c), 4.05 (1H, at, J9.1 Hz, H-4a), 4.09 (1H, dd, $J_{5,6}$ 2.5 Hz, $J_{6,6'}$ 12.7 Hz, H-6c), 4.21 (1H, dd, $J_{5,6}$ 3.4 Hz, $J_{6,6'}$ 12.6 Hz, H-6b), 4.29 (1H, dd, $J_{5,6}$ 3.4 Hz, $J_{6,6'}$ 12.4 Hz, H-6'c), 4.35 (1H, dd, $J_{5,6}$ 4.3 Hz, $J_{6,6'}$ 12.3 Hz, H-6a), 4.48-4.52 (2H, m, H-6'a, H-6'b), 4.78 (1H, dd, $J_{1,2}$ 4.1 Hz, $J_{2,3}$ 10.3 Hz, H-2b), 4.90 (1H, dd, $J_{1,2}$ 4.1 Hz, $J_{2,3}$ 10.6 Hz, H-2c), 5.01 (1H, dd, $J_{1,2}$ 8.0 Hz, $J_{2,3}$ 9.0 Hz, H-2a), 5.11 (1H, at, J10.1 Hz, H-4c), 5.31 (1H, d, $J_{1,2}$ 3.9 Hz, H-1b), 5.32-5.44 (3H, m, H-3a, H-3b, H-3c), 5.45 (1H, d, $J_{1,2}$ 4.1 Hz, H-1c), 5.79 (1H, d, $J_{1,2}$ 8.2 Hz, H-1a); for a compound selected data only: $\delta_H$ (500 MHz, CDCl$_3$) 2.08, 2.09, 2.12, 2.18, 2.21, 2.23, 2.26 (30H, 8×s, 10×OAc), 5.07 (1H, at, J 9.9 Hz), 6.28 (1H, d, $J_{1,2}$ 3.8 Hz, H-1a). Remaining signals lie in the following multiplet regions, 3.85-3.89, 3.90-3.98, 3.99-4.07, 4.15-4.18, 4.23-4.27, 4.29-4.32, 4.43-4.49, 4.74-4.76, 4.84-4.87, 4.98-4.94, 5.25-5.54; m/z (ES+) 984 (MNH$_4^+$, 30%), 989 (MNa$^+$, 100%); m/z HRMS (ES$^+$) Calcd. For C$_{40}$H$_{58}$O$_{27}$N (MNH$_4^+$) 984.3196 Found 984.3199.

EXAMPLE 10

2,3,6-Tri-O-acetyl-4-O-(2,3,6-tri-O-acetyl-4-O-(2,3,4,6-tetra-O-acetyl-$\alpha$-O-glucopyranosyl)-$\alpha$-D-glucopyranosyl)-$\alpha$-D-glucopyranosyl bromide

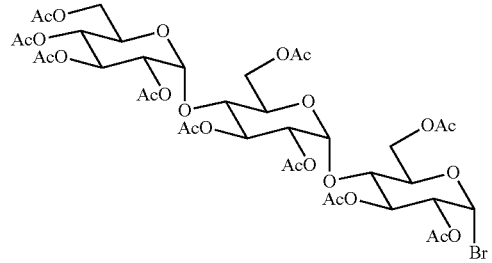 [SMILES: CC(=O)OCC1OC(Br)C(OC(C)=O)C(OC(C)=O)C1OC1OC(COC(C)=O)C(OC2OC(COC(C)=O)C(OC(C)=O)C(OC(C)=O)C2OC(C)=O)C(OC(C)=O)C1OC(C)=O]

1,2,3,6-Tetra-O-acetyl-4-O-(2,3,6-tri-O-acetyl-4-O-(2,3,4,6-tetra-O-acetyl-$\alpha$-O-glucopyranosyl)-$\alpha$-D-glucopyranosyl)-D-glucopyranose (200 mg, 0.21 mmol) was dissolved in anhydrous DCM (5 mL). To this hydrogen bromide (33% in acetic acid, 2 mL) was added. The mixture was left under argon at RT. After a 30 min period, t.l.c. (petrol:ethyl acetate, 1:2) indicated the formation of a product ($R_f$ 0.6) with complete consumption of the starting material ($R_f$ 0.3). The reaction mixture was partitioned between DCM (10 mL) and water (10 mL), and the aqueous layer re-extracted with DCM (3×10 mL). The combined organic layers were washed with sodium hydrogen carbonate (20 mL of a saturated aqueous solution) until pH 8 was obtained, brine (20 mL), dried (MgSO$_4$), filtered and concentrated in vacuo to afford the title product (203 mg, 98%) as a white foam; $[\alpha]_D^{22}$ +152.2 (c, 1.0 in CHCl$_3$); $\delta_H$ (400 MHz, CDCl$_3$) 2.03, 2.05, 2.06, 2.08, 2.10, 2.13, 2.18, 2.21 (30H, 10×COCH$_3$), 3.93-3.99 (3H, m, H-4b, H-5a, H-5b), 4.05-4.10 (2H, m, H-4c, H-6a), 4.20 (1H, dd, $J_{5,6}$ 1.8 Hz, $J_{6,6'}$ 12.2 Hz, H-6b), 4.26-4.34 (2H, m, H-5c, H-6a'), 4.35 (1H, dd, $J_{5,6}$ 3.5 Hz, $J_{6,6'}$ 12.7 Hz, H-6c), 4.52 (1H, dd, $J_{5,6}$ 0.6 Hz, $J_{6,6'}$ 12.2 Hz, H-6b'), 4.57 (1H, dd, $J_{5,6}$ 2.1 Hz, $J_{6,6'}$ 12.4 Hz, H-6c''), 4.74 (1H, dd, $J_{1,2}$ 4.1 Hz, $J_{2,3}$ 9.9 Hz, H-2c), 4.78 (1H, dd, $J_{1,2}$ 4.2 Hz, $J_{2,3}$ 10.2 Hz, H-2b), 4.88 (1H, dd, $J_{1,2}$ 4.0 Hz, $J_{2,3}$ 10.5 Hz, H-2a), 5.10 (1H, at J9.7 Hz, H-4a), 5.32 (1H, d, $J_{1,2}$ 4.0 Hz, H-1b), 5.39(1H, at J 9.9 Hz, H-3q), 5.43-5.46 (1H, m, H-3b), 5.45 (1H, d, $J_{1,2}$ 3.8 Hz, H-1a), 5.64 (1H, at J9.5 Hz, H-3c), 6.53 (1H, d, $J_{1,2}$ 3.9 Hz, H-1c).

EXAMPLE 11

1-Thio-2,3,6-Tri-O-acetyl-4-O-(2,3,6-tri-O-acetyl-4-O-(2,3,4,6-tetra-O-acetyl-α-O-glucopyranosyl)-α-D-glucopyranosyl)-β-D-glucopyranose

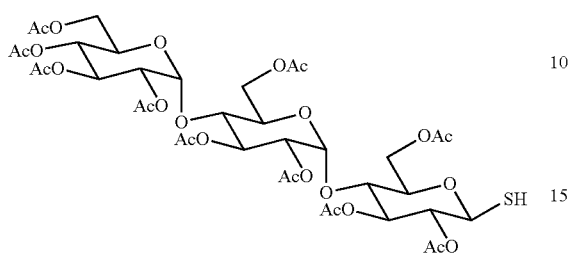

2,3,6-Tri-O-acetyl-4-O-(2,3,6-tri-O-acetyl-4-O-(2,3,4,6-tetra-O-acetyl-α-O-glucopyranosyl)-α-D-glucopyranosyl)-α-D-glucopyranosyl bromide (2.10 g, 2.10 mmol) was dissolved in anhydrous acetone (60 mL). To this anhydrous thiourea (315 mg, 4.2 mmol) was added and then heated to reflux under an atmosphere of argon. After a 6.5 h period, t.l.c. (petrol:ethyl acetate, 1:2) indicated the formation of a product ($R_f$ 0.0) with complete consumption of the starting material ($R_f$ 0.3). The reaction was concentrated in vacuo and titurated with DCM to remove the organics from the excess thiourea. The filtrate was concentrated in vacuo and the residue was purified by column flash chromatography (ethyl acetate/methanol, 9:1) to afford the intermediate 2,3,6-tri-O-acetyl-4-O-(2,3,6-tri-O-acetyl-4-O-(2,3,4,6-tetra-O-acetyl-α-O-glucopyranosyl)-α-D-glucopyranosyl)-β-D-glucopyranosyl-1-isothiouronium bromide (1.14 g, 50%) which was carried on without characterisation. This intermediate (100 mg, 0.09 mmol) and $Na_2S_2O_5$ (22 mg, 0.11 mmol) were added to a stirred mixture of DCM (30 mL) and water (15 mL). The mixture was heated to reflux under argon. After 2.5 h, t.l.c. (petrol:ethyl acetate, 1:2) indicated the formation of a product ($R_f$ 0.4) with complete consumption of the starting material ($R_f$ 0.0), at which point the reaction was cooled to RT and the phases separated. The aqueous layer was re-extracted with DCM (2×20 mL). The combined organic layers were washed with brine (20 mL), dried (MgSO$_4$), filtered and the solvent removed in vacuo to afford the title product (74 mg, 84%) as a white amorphous solid; $[\alpha]_D^{22}$+99.5 (c, 1.0 in CHCl$_3$); $\delta_H$ (400 MHz, CDCl$_3$) 1.99, 2.00, 2.01, 2.02, 2.03, 2.05, 2.10, 2.15, 2.18 (30H, 9×s, 10×COCH$_3$), 3.72-3.76 (1H, m, H-5a), 3.90-4.00 (4H, m, H-4a, H-4b, H-5b, H-5c), 4.05 (1H, dd, $J_{5,6}$ 2.2 Hz, $J_{6,6'}$ 12.3 Hz, H-6c), 4.17 (1H, dd, $J_{5,6}$ 3.3 Hz, $J_{6,6'}$ 12.3 Hz, H-6b), 4.25 (1H, dd, $J_{5,6}$ 3.6 Hz, $J_{6,6'}$ 12.5 Hz, H-6c'), 4.30 (1H, $J_{5,6}$ 4.3 Hz, $J_{6,6'}$ 12.2 Hz, H-6c), 4.44 (1H, dd, $J_{5,6}$ 2.2 Hz, $J_{6,6'}$ 12.1 Hz, H-6a'), 4.46 (1H, dd, $J_{5,6}$ 2.2 Hz, $J_{6,6'}$ 12.2 Hz, H-6b'), 4.59 (1H, d, $J_{1,2}$ 9.7 Hz, H-1a), 4.74 (1H, dd, $J_{1,2}$ 4.1 Hz, $J_{2,3}$ 10.6 Hz, H-2b), 4.80 (1H, at, J9.0 Hz, H-2a), 4.85 (1H, dd, $J_{1,2}$ 4.1 Hz, $J_{2,3}$ 10.6 Hz, H-2c), 5.07 (1H, at, J9.9 Hz, H-4c), 5.25 (1H, at, J9.0 Hz, H-3a), 5.26 (1H, d, $J_{1,2}$ 4.1 Hz, H-1b), 5.35 (1H, at, J10.0 Hz, H-3b), 5.37-5.41 (2H, m, H-1c, H-3c).

EXAMPLE 12

1-Thioacetyl-2,3,6-tri-O-acetyl-4-O-(2,3,6-tri-O-acetyl-4-O-(2,3,4,6-tetra-O-acetyl-α-O-glucopyranosyl)-α-D-glucopyranosyl)-β-D-glucopyranose

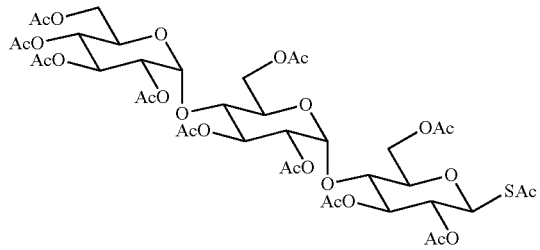

2,3,6-Tri-O-acetyl-4-O-(2,3,6-tri-O-acetyl-4-O-(2,3,4,6-tetra-O-acetyl-α-O-glucopyranosyl)-α-D-glucopyranosyl)-β-D-glucopyranosyl bromide (11.2 g, 11.6 mmol) and potassium thioacetate (3.96 g, 34.8 mmol) were suspended in anhydrous THF (40 ml) and heated to reflux under an inert atmosphere of argon. After 14 h, t.l.c. (petrol/EtOAc, 1:2) indicated the formation of a major product ($R_f$ 0.4) along with complete consumption of the starting material ($R_f$ 0.45). The reaction was diluted with water (80 mL) and allowed to cool to RT. The phases were separated and the aqueous phase was re-extracted with DCM (3×40 mL). The combined organic layers were washed with sat. NaHCO$_3$ (50 mL) until pH 8 was obtained, brine (50 mL), dried over MgSO$_4$, filtered and concentrated in vacuo. The residue was purified by flash column chromatography (petrol/EtOAc, 1:4) to afford the title compound (8.08 g, 71%) as a white foam; $[\alpha]_D^{25}$+86.4 (c, 1.0 in CHCl$_3$); $\delta_H$ (400 MHz, CDCl$_3$) 2.01, 2.02, 2.05, 2.08, 2.11, 2.17 (27H, 6×s, 9×OAc), 2.40 (3H, s, SAc), 3.88 (1H, ddd, $J_{4,5}$ 9.8 Hz, $J_{5,6}$ 4.0 Hz, $J_{5,6'}$ 2.7 Hz, H-5a), 3.92-4.01 (4H, m, H-4a, H-4b, H-5b, H-5c), 4.07 (1H, dd, $J_{5,6}$ 2.4 Hz, $J_{6,6'}$ 12.3 Hz, H-6c), 4.19 (1H, dd, $J_{5,6}$ 3.5 Hz, $J_{6,6'}$ 12.2 Hz, H-6b), 4.27 (1H, dd, $J_{5,6'}$ 3.8 Hz, $J_{6,6'}$ 12.3 Hz, H-6'c), 4.30 (1H, dd, $J_{5,6}$ 4.2 Hz, $J_{6,6'}$ 12.4 Hz, H-6a), 4.46 (1H, dd, $J_{5,6'}$ 2.6 Hz, $J_{6,6'}$ 12.3 Hz, H-6'b), 4.47 (1H, dd, $J_{5,6'}$ 2.2 Hz, $J_{6,6'}$ 12.2 Hz, H-6'a), 4.76 (1H, dd, $J_{1,2}$ 3.9 Hz, $J_{2,3}$ 10.0 Hz, H-2b), 4.87 (1H, dd, $J_{1,2}$ 3.8 Hz, $J_{2,3}$ 10.6 Hz, H-2c), 5.99 (1H, dd, $J_{1,2}$ 10.3 Hz, $J_{2,3}$ 9.1 Hz, H-2a), 5.08 (1H, at, J9.9 Hz, H-4c), 5.27 (1H, d, $J_{1,2}$ 4.0 Hz, H-1b), 5.31 (1H, d, $J_{1,2}$ 10.0 Hz, H-1a), 5.33-5.43 (4H, m, H-1c, H-3a, H-3b, H-3c); $\delta_C$ (125 MHz, CDCl$_3$) 20.7, 20.8, 20.9, 21.0, 21.1 (5×q, 10×COCH$_3$, SCOCH$_3$), 31.0 (q, SCOCH$_3$) 61.9 (t, C-6c), 62.7 (t, C-6b), 63.3 (t, C-6a), 68.4 (d, C-4c), 69.0 (d, C-5b), 69.5 (d, C-5c), 69.8 (d, C-3c), 70.3 (d, C-2a), 70.5 (d, C-2c), 70.9 (d, C-2a), 72.1 (d, C-3b), 73.0 (d, C-4b), 74.1 (d, C-4a), 76.6 (d, C-3a), 76.9 (d, C-5a), 80.2 (d, C-1a), 96.1 (d, C-1c), 96.4 (d, C-1b), 169.4, 169.6, 169.8, 169.9, 170.3, 170.5, 170.6 (7×s, 10×COCH$_3$), 196.0 (s, SCOCH$_3$); m/z (ES+) 1000 (MNH$_4^+$, 60%), 1003 (MNa$^+$, 100%).

EXAMPLE 13

1Thio-β-D-maltotriose

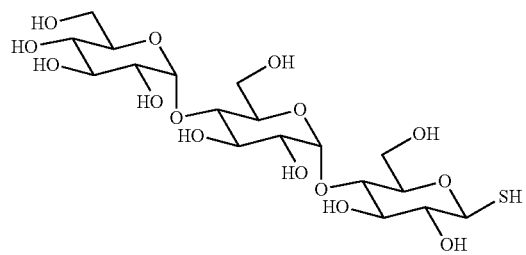 [SMILES: OCC1OC(OC2C(CO)OC(OC3C(CO)OC(S)C(O)C3O)C(O)C2O)C(O)C(O)C1O]

1-Thioacetyl-2,3,6-tri-O-acetyl-4-O-(2,3,6-tri-O-acetyl-4-O-(2,3,4,6-tetra-O-acetyl-α-glucopyranosyl)-α-D-glucopyranosyl)-1-thio-β-D-glucopyranose (600 mg, 0.6 mmol) and NaOAc (18 mg, 0.18 mmol) were added to a stirred solution of MeOH (10 ml). After 10 min, t.l.c. (EtOAc/MeOH, 9:1) indicated the formation of a product ($R_f$ 0.0) with complete consumption of the starting material ($R_f$ 0.9). The reaction was neutralised with the addition of Dowex®-50 ion exchange resin after which point the reaction was filtered and concentrated in vacuo to afford the title compound (305 mg, 98%) as an amorphous solid; $[\alpha]_D^{25}$ +123 (c, 1.0 in MeOH); $\delta_H$ (400 MHz, $D_2O$), 3.15 (1H, at, J9.2 Hz, H-2a), 3.26 (1H, at, J9.3 Hz), 3.41-3.82 (16H, m, H-2b, H-2c, H-3a, H-3b, H-3c, H-4a, H-4b, H-4c, H-5a, H-5b, H-5c, H-6a, H-6b, H-6c, H-6'a, H-6'b, H-6'c), 4.42 (1H, d, $J_{1,2}$ 9.6 Hz, H-1a), 5.23 (1H, d, $J_{1,2}$ 1.7 Hz, H-1), 5.24 (1H, d, $J_{1,2}$ 1.8 Hz, H-1); $\delta_C$ (100 MHz, $D_2O$), 60.8, 70.0 (2×t, C-6a, C-6b, C-6c), 69.6, 71.5, 71.8, 72.1, 73.0, 73.2, 73.6, 76.0, 77.1, 77.6, 79.0 (11×d, C-2a, C-2b, C-2c, C-3a, C-3b, C-3c, C-4a, C-4b, C-4c, C-5a, C-5b, C-5c), 80.2 (d, C-1a), 99.8, 100.1 (2×d, C-1b, C-1c); m/z (ES−) 519 (100%, M-H⁺); m/z HRMS (ES−) calcd. for $C_{18}H_{31}O_{15}S$ (M-H⁺) 519.1384. Found 519.1389.

EXAMPLE 14

1,2,3,6-Tetra-O-acetyl-4-O-(2,3,6-tri-O-acetyl-4-O-(2,3,6-tri-O-acetyl-4-O-(2,3,6-tri-O-acetyl-4-O-(2,3,6-tri-O-acetyl-4-O-(2,3,6-tri-O-acetyl-4-O-(2,3,4,6-tetra-O-acetyl-α-O-glucopyranosyl)-α-D-glucopyranosyl)-α-D-glucopyranosyl)-α-D-glucopyranosyl)-α-D-glucopyranosyl)-α-D-glucopyranosyl)-D-glucopyranose Sodium acetate (420 mg, 5.2 mmol) was added to acetic anhydride (30 mL) and heated to reflux, at which point maltoheptose (1.00 g, 0.86 mmol) was added and the reaction stirred vigorously. After 90 min t.l.c. petrol:ethyl acetate, 1:3) indicated the formation of a product ($R_f$ 0.3) with complete consumption of the starting material ($R_f$ 0.0). The reaction was allowed to cool to RT, diluted with DCM (50 mL) and partitioned with water (100 mL). The phases were separated and the aqueous layer was re-extracted with DCM (2×40 mL). The combined organic layers were washed with sodium hydrogen carbonate (200 mL of a saturated aqueous solution) until pH 8 was obtained, brine (100 mL), dried ($MgSO_4$), filtered and concentrated in vacuo. The residue was purified by flash column chromatography (petrol:ethyl acetate, 1:3) to afford the title product as an amorphous white solid as a mixture of anomers ($\alpha/\beta$, 15/85); $\delta_H$(500 MHz, $CDCl_3$)2.02, 2.03, 2.04, 2.05, 2.06, 2.07, 2.08, 2.10, 2.13, 2.19, 2.22, 2.24 (66H, 12×s, 22×OAc), 3.89-4.14 (13H, m, H-4a, H-4b, H-4c, H-4d, H-4e, H-4f, H-5a, H-5b, H-5c, H-5d, H-5e, H-5f, H-5g), 4.25-4.34, 4.39 (1H, dd, J4.0 Hz, J12.3 Hz), 4.52-4.56 (13H, m, H-6a, H-6a', H-6b, H-6b', H-6c, H-6c', H-6d, H-6d', H-6e, H-6e', H-6f, H-6f', H-6d, H-6g'), 4.75-4.79 (5H, m, H-2b, H-2c, H-2d, H-2e, H-2e, H-2f, 4.90 (1H, dd, $J_{1,2}$ 3.7 Hz, $J_{2,3}$ 10.5 Hz, H-2g), 5.00 (1H, at, J9.4 Hz, H-4g), 5.31-5.45 (13H, m, H-3a, H-3b, H-3c, H-3d, H-3e, H-3f, H-3g, H-1b, H-1c, H-1d, H-1e, H-1f, H-1g), 5.79 (0.85H, d, $J_{1,2}$ 8.1 Hz, H-1a$_\beta$), 6.28 (0.15H, d, $J_{1,2}$ 4.0 Hz, H-1a$_\alpha$).

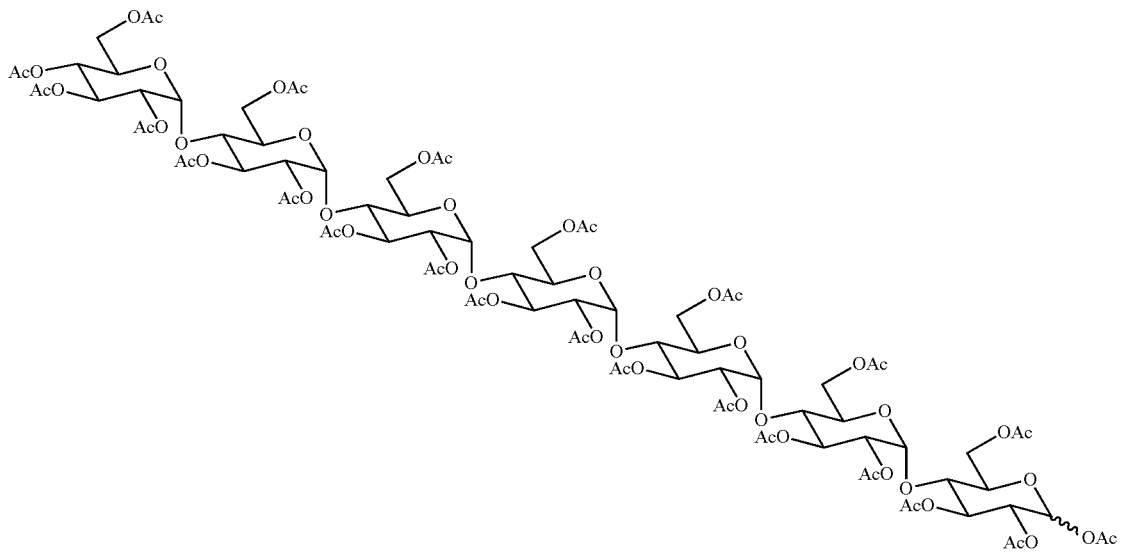 [SMILES: CC(=O)OCC1OC(OC2C(COC(C)=O)OC(OC3C(COC(C)=O)OC(OC4C(COC(C)=O)OC(OC5C(COC(C)=O)OC(OC6C(COC(C)=O)OC(OC7C(COC(C)=O)OC(OC(C)=O)C(OC(C)=O)C7OC(C)=O)C(OC(C)=O)C6OC(C)=O)C(OC(C)=O)C5OC(C)=O)C(OC(C)=O)C4OC(C)=O)C(OC(C)=O)C3OC(C)=O)C(OC(C)=O)C2OC(C)=O)C(OC(C)=O)C(OC(C)=O)C1OC(C)=O]

EXAMPLE 15

2,3,6-Tri-O-acetyl-4-O-(2,3,6-tri-O-acetyl-4-O-(2,3,6-tri-O-acetyl4-O-(2,3,6-tri-O-acetyl-4-O-(2,3,6-tri-O-acetyl-4-O-(2,3,6-tri-O-acetyl-4-O-(2,3,4,6-tetra-O-acetyl-$_\alpha$-O-glucopyranosyl)-$_\alpha$-D-glucopyranosyl)-$_\alpha$-D-glucopyranosyl)-$_\alpha$-D-glucopyranosyl)-$_\alpha$-D-glucopyranosyl)-$_\alpha$-D-glucopyranosyl)-$_\alpha$-D-glucopyranosyl bromide

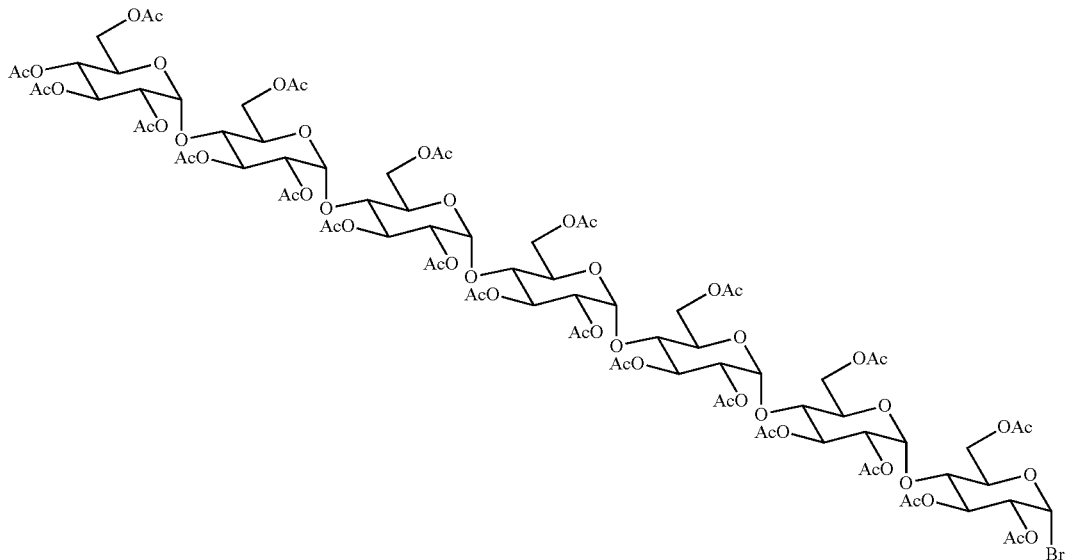 [SMILES: CC(=O)OCC1OC(Br)C(OC(C)=O)C(OC(C)=O)C1OC1OC(COC(C)=O)C(OC2OC(COC(C)=O)C(OC3OC(COC(C)=O)C(OC4OC(COC(C)=O)C(OC5OC(COC(C)=O)C(OC6OC(COC(C)=O)C(OC(C)=O)C(OC(C)=O)C6OC(C)=O)C(OC(C)=O)C5OC(C)=O)C(OC(C)=O)C4OC(C)=O)C(OC(C)=O)C3OC(C)=O)C(OC(C)=O)C2OC(C)=O)C(OC(C)=O)C1OC(C)=O]

1,2,3,6-Tetra-O-acetyl-4-O-(2,3,6-tri-O-acetyl-4-O-(2,3,6-tri-O-acetyl-4-O-(2,3,6-tri-O-acetyl-4-O-(2,3,6-tri-O-acetyl-4-O-(2,3,6-tri-O-acetyl-4-O-(2,3,4,6-tetra-O-acetyl-$_\alpha$-glucopyranosyl)-$_\alpha$-D-glucopyranosyl)-$_\alpha$-D-glucopyranosyl)-$_\alpha$-D-glucopyranosyl)-$_\alpha$-D-glucopyranosy)-$_\alpha$-D-glucopyranosyl)-D-glucopyranose (100 mg, 0.05 mmol) was dissolved in anhydrous DCM (5 mL). To this hydrogen bromide (33% in acetic acid, 0.5 mL) was added. The mixture was left stirring under an atmosphere of argon at RT. After a 40 min period, t.l.c. (petrol:ethyl acetate, 1:3) indicated the formation of a product ($R_f$ 0.7) with complete consumption of the starting material ($R_f$ 0.3). The reaction mixture was partitioned between DCM (10 mL) and water (10 mL), and the aqueous layer re-extracted with DCM (3×10 mL). The combined organic layers were washed with sodium hydrogen carbonate (150 mL of a saturated aqueous solution) until pH 7 was obtained, brine (20 mL), dried (MgSO$_4$), filtered and concentrated in vacuo to afford the title product (98 mg, 96%) as a white foam; $[\alpha]_D^{22}$+162.0 (c, 1.0 in CHCl$_3$); $\delta_H$ (400 MHz, CDCl$_3$) 2.02, 2.03, 2.04, 2.06, 2.08, 2.10, 2.11, 2.14, 2.19, 2.23, 2.24, 2.25 (66H, 12×s, 22×OAc), 3.94-4.04 (12H, m, H-4b, H-4c, H-4d, H-4e, H-4f, H-5b, H-5c, H-5d, H-5e, H-5f, H-5g), 4.08 (1H, dd, $J_{5,6}$ 2.2 Hz, $J_{6,6'}$ 12.6 Hz, H-6), 4.19-4.33, 4.53-4.60 (12H, m, H-5a, H-6b, H-6b', H-6c, H-6c', H-6d, H-6d', H-6e, H-6e', H-6f, H-6f', H-6g, H-6g'), 4.12 (1H, at, J9.5 Hz, H-4a), 4.40 (1H, dd, $J_{5,6}$ 3.1 Hz, $J_{6,6'}$ 12.7 Hz, H-6a), 4.64 (1H, dd, $J_{5,6}$ 2.3 Hz, $J_{6,6'}$ 12.5 Hz, H-6a'), 4.74 (1H, dd, $J_{1,2}$ 3.9 Hz, $J_{2,3}$ 9.7 Hz, H-2a), 4.75-4.97 (5H, m, H-2b, H-2c, H-2d, H-2e, H-2f), 4.89 (1H, d, $J_{1,2}$ 4.0 Hz, $J_{2,3}$ 10.6 Hz, H-2g), 5.11 (1H, at, J9.9 Hz, H-4g), 5.32-5.47 (12H, m, H-1b, H-1c, H-1d, H-1e, H-1f, H-1g, H-3b, H-3c, H-3d, H-3e, H-3f, H-3g), 5.65 (1H, at, J9.4 Hz, H-3a), 6.54 (1H, d, $J_{1,2}$ 4.3 Hz, H-1a).

EXAMPLE 16

1-Thio-2,3,6-tri-O-acetyl-4-O-(2,3,6-tri-O-acetyl-4-O-(2,3,6-tri-O-acetyl-4-O-(2,3,6-tri-O-acetyl-4-O-(2,3,6-tri-O-acetyl-4-O-(2,3,6-tri-O-acetyl-4-O-(2,3,4,6-tetra-O-acetyl-$_\alpha$-O-glucopyranosyl)-$_\alpha$-D-glucopyranosyl)-$_\alpha$-D-glucopyranosyl)-$_\alpha$-D-glucopyranosyl)-$_\alpha$-D-glucopyranosyl)-$_\alpha$-D-glucopyranosyl)-$_\beta$-D-glucopyranose washed with brine (20 mL), dried (MgSO$_4$), filtered and the solvent removed in vacuo to afford the title product (185 mg, 90%) as a white amorphous solid; [α]$_D$$^{24}$+128.1 (c, 1.0 in CHCl$_3$); δ$_H$(500 MHz, CDCl$_3$), 2.00, 2.01, 2.02, 2.03, 2.04, 2.05, 2.07, 2.08, 2.12, 2.17, 2.19, 2.21, 2.22, 2.23 (66H, 14×s, 22×COCH$_3$), 2.27 (1H, d, J$_{1,SH}$ 9.8 Hz, SH), 3.76 (1H, dat, J$_{4,5}$ 9.7 Hz, J3.5 Hz, H-5a), 3.92-4.08 (12H, m, H-4a, H-4b, H-4c, H-4d, H-4e, H-4f, H-5b, H-5c, H-5d, H-5e, H-5f, H-5g), 4.17-4.36, 4.49-4.56 (12H, m, H-6b, H-6b', H-6c,

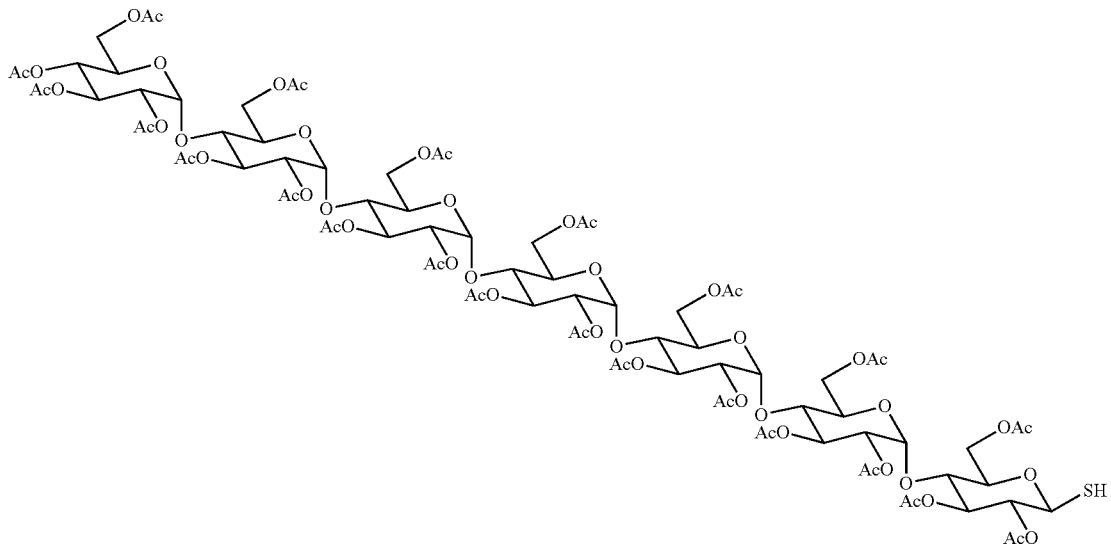 [SMILES: CC(=O)OCC1OC(S)C(OC(C)=O)C(OC(C)=O)C1OC1OC(COC(C)=O)C(OC2OC(COC(C)=O)C(OC3OC(COC(C)=O)C(OC4OC(COC(C)=O)C(OC5OC(COC(C)=O)C(OC6OC(COC(C)=O)C(OC(C)=O)C(OC(C)=O)C6OC(C)=O)C(OC(C)=O)C5OC(C)=O)C(OC(C)=O)C4OC(C)=O)C(OC(C)=O)C3OC(C)=O)C(OC(C)=O)C2OC(C)=O)C(OC(C)=O)C1OC(C)=O]

2,3,6-Tri-O-acetyl-4-O-(2,3,6-tri-O-acetyl-4-O-(2,3,6-tri-O-acetyl-4-O-(2,3,6-tri-O-acetyl-4-O-(2,3,6-tri-O-acetyl-4-O-(2,3,6-tri-O-acetyl-4-O-(2,3,6-tri-O-acetyl-4-O-(2,3,4,6-tetra-O-acetyl-$_\alpha$-O-glucopyranosyl)-$_\alpha$-D-glucopyranosyl)-$_\alpha$-D-glucopyranosyl)-$_\alpha$-D-glucopyranosyl)-$_\alpha$-D-glucopyranosyl)-$_\alpha$-D-glucopyranosyl)-$_\alpha$-D-glucopyranosyl bromide (1.08 g, 0.5 mmol) and tetrabutylammonium iodide (19 mg, 0.05 mmol) were dissolved in anhydrous acetone (50 mL). To this dried thiourea (52 mg, 0.7 mmol) was added and the reaction was then heated to reflux under an atmosphere of argon. After a 8 h period, t.l.c. (petrol:ethyl acetate, 1:4) indicated the formation of a minor product (R$_f$ 0.0) with complete consumption of the starting material (R$_f$ 0.6). The reaction was concentrated in vacuo and titurated with DCM to remove the organics from the excess thiourea The filtrate was concentrated in vacuo and the residue was purified by column flash chromatography (ethyl acetate/methanol, 9:1) to afford the intermediate 2,3,6-tri-O-acetyl-4-O-(2,3,6-tri-O-acetyl-4-O-(2,3,6-tri-O-acetyl-4-O-(2,3,6-tri-O-acetyl-4-O-(2,3,6-tri-O-acetyl-4-O-(2,3,6-tri-O-acetyl-4-O-(2,3,4,6-tetra-O-acetyl-$_\alpha$-O-glucopyranosyl)-$_\alpha$-D-glucopyranosyl)-$_\alpha$-D-glucopyranosyl)-$_\alpha$-D-glucopyranosyl)-$_\alpha$-D-glucopyranosyl)-$_\alpha$-D-glucopyranosyl)-$_\beta$-D-glucopyranosyl-1-isothiouronium bromide (212 mg, 19%) which was taken on further without characterisation. This intermediate (210 mg, 0.09 mmol) and Na$_2$S$_2$O$_5$ (22 mg, 0.11 mmol) were added to a stirred mixture of DCM (10 mL) and water (5 mL). The mixture was heated to reflux under argon. After 4.5 h, t.l.c. (petrol:ethyl acetate, 1:2) indicated the formation of a product (R$_f$ 0.2) with complete consumption of the starting material (R$_f$ 0.0), at which point the reaction was cooled to RT and the phases separated. The aqueous layer was re-extracted with DCM (2×10 mL). The combined organic layers were H-6c', H-6d, H-6d', H-6e, H-6e', H-6f, H-6f', H-6g, H-6g'), 4.39 (1H, dd, J$_{5,6}$ 3.6 Hz, J$_{6,6'}$ 12.2 Hz, H-6a), 4.48 (1H, dd, J$_{5,6}$ 3.2 Hz, J$_{6,6'}$ 12.3 Hz, H-6a), 4.62 (1H, at, J9.5 Hz, H-1a), 4.73-4.78 (5H, m, H-2b, H-2c, H-2d, H-2e, H-2f), 4.82 (1H, at, J9.5 Hz, H-2a), 4.88 (1H, dd, J$_{1,2}$ 4.0 Hz, J$_{2,3}$ 10.4 Hz, H-2g), 5.09 (1H, at, J9.9 Hz, H-4g), 5.27 (1H, at, J9.1 Hz, H-3a), 5.30-5.44 (12H, m, -1b, H-1c, H-1d, H-1e, H-1f, H-1g, H-3b, H-3c, H-3d, H-3e, H-3f, H-3g).

EXAMPLE 17

Preparation of SBLCys156-S—SePh

Single site modification was investigated using a model-cysteine-containing protein, serine protease subtilisin *Bacillus lentus* mutant S156C (SBLCys156). SBLCys156 (10 mg) was dissolved in degassed aqueous buffer solution (1 mL, 70 mM CHES, 5 mM MES, 2 mM CaCl$_2$, pH 9.5). PhSeBr (5 mg, 0.02 mmol) was dissolved in acetonitrile (200 μL), of which 150 μL (40 eq) was added to the protein solution and placed on an end-over-end rotator. After 30 min, the absence of free thiol was shown by Ellman's analysis (G. L. Ellman, K. D. Courtney, V. Andres, R. M. Featherstone, *Biochem. Pharmacol.* 1961, 7, 88). The reaction was placed on an end-over-end rotator for a further 30 min, at which point the reaction mixture was loaded onto a PD10 Sephadex® G25 column and eluted with 70 mM HEPES, 2 mM CaCl$_2$, pH 7.0. The protein fraction was collected and dialysed (MWCO 12-14 KDa) against water, (1×4L for 1 h, 2×2L for 30 min), to afford SBLS156C—S—SePh; m/z (ES$^+$) found 26864 calcd. 26870.

EXAMPLE 18

Preparation of SS$_\beta$GCys344Cys432-(S—SePh)$_2$

Multiple site modifications were investigated using a mutant of the thermophilic β-glycosidase from the archeon *Sulfolobus solfataricus* containing two cysteine residues (SS$_\beta$G-Cys344Cys432). SS$_\beta$G-Cys344Cys432 (1 mg) was dissolved in aqueous buffer solution (1 mL, 70 mM CHES, 5 mM MS, 2 mM CaCl$_2$, pH 9.5). PhSeBr (2 mg, 0.02 mmol) was dissolved in acetonitrile (200 μL), of which 20 μL (74 eq) was added to the protein solution and placed on an end-over-end rotator. After 1 h the reaction mixture was loaded onto a PD10 Sephadex® G25 column and eluted with (70 mM HEPES, 2 mM CaCl$_2$, pH 7.0) to afford SS$_\beta$GCys344Cys432-(S—SePh)$_2$; m/z (ES$^+$) found 57700 calcd. 57697.

EXAMPLE 19

Representative protein glycosylation with sugar thiols and reaction with other thiols SBLCys156-S—SePh (1 mg) was dissolved in aqueous buffer solution (1 mL, 70 mM CHES, 5 mM MES, 2 mM CaCl$_2$, pH 9.5). The sugar thiol or other thiol was dissolved in water and added to the protein solution in the stated quantities (see Table below for equivalents) and the mixture placed in an end-over-end rotator. After 1 h the reaction was analysed by mass spectrometry.

Results

| Protein[1] | Thiol | Equiv of thiol | Conv. % | ESI-MS Found (theory) |
|---|---|---|---|---|
| SBLCys156 | GlcSH | 5 | >95 | 26908 (26909) |
| SBLCys156 | GalSH | 5 | >95 | 26908 (26909) |
| SBLCys156 | GlcNAcSH | 1 | >95 | 26944 (26950) |
| SBLCys156 | GlcGlcGlcSH | 5 | >95 | 27228 (27233) |
| SBLCys156 | GlcGlcGlcGlcGlcGlcGlcSH | 10 | >95 | 27878 (27881) |
| SS$_\beta$G-Cys344Cys432 | GlcSH | 60 | >95 | 57760 (57775) |
| SBLCys156 | BocCysThrOMe | 20 | | 27030 (27047) |
| SBLCys156 | Glutathione (Glu-Cys-Gly) | 20 | | 27022 (27020) |
| SBLCys156[2] | ManSH | 20 | >95 | 27058 (27062) |
| SBLCys156 | (AcO)$_4$ManSH | 10 | >95 | 27080 (27060) |
| SBLCys156 | Man(1,6)ManSH | 10 | >95 | 27075 (27071) |
| SBLCys156 | (AcO)$_4$Man(1,6)-(AcO)$_2$ManSH / (AcO)$_4$Man(1,3) | 20 | >95 | 27054 (27053) |
| SBLCys156[2] | Man(1,6)-ManSH / Man(1,3) | 20 | >95 | 27384 (27386) |

Conv. = conversion as determined by ESI-MS
[1]Activated by reaction with phenyl selenium bromide to give the corresponding protein-S—Se—Ph or protein-(S—Se—Ph)$_2$ compound prior to addition of the thiol.
[2]Reacted with PMSF (phenylmethylsulfonyl fluoride) prior to glycosylation to prevent protein degradation due to proteolytic activity.

The results in the above Table demonstrate that the method of the invention provides high percentage conversion to the desired products using as little as one equivalent of thiol compound. Furthermore, the results demonstrate that the method of the invention can be used for single and multiple site protein glycosylations. The three glycosylation sites in SBL-Cys156 and SS$_\beta$GCys344Cys432 are found in very varying protein structures and environments with different levels of exposure, illustrating the broad applicability of the method of the invention.

EXAMPLE 20

Representative protein glycosylation of SBLCys156 using GlcGlcGlcGlcGlcGlcGlc-SH 1-Thio-2,3,6-tri-O-acetyl-4-O-(2,3,6-tri-O-acetyl-4-O-(2,3,6-tri-O-acetyl-4-O-(2,3,6-tri-O-acetyl-4-O-(2,3,6-tri-O-acetyl-4-O-(2,3,6-tri-O-acetyl-4-O-(2,3,4,6-tetra-O-acetyl-$\alpha$-O-glucopyranosyl)-$\alpha$-D-glucopyranosyl)-$\alpha$-D-glucopyranosyl)-$\alpha$-D-glucopyranosyl)-$\alpha$-D-glucopyranosyl)-$\alpha$-D-glucopyranosyl)-$\alpha$-D-glucopyranose (15 mg, 0.007 mmol) and sodium methoxide (2 mg, 0.007 mmol) were added to a stirred solution of MeOH (2 ml). After 2 h, t.l.c. (petrol:EtOAc, 1:2) indicated the formation of a product (R$_f$ 0.0) with the complete consumption of the starting material (R$_f$ 0.2). The reaction was neutralised with the addition of Dowex®-50 ion exchange resin after which point the reaction was filtered and concentrated in vacuo. The crude 1-thio-$\beta$-D-maltoheptose was taken up into water (5 mL) of which 300 μL (11 eq) was added to a solution of SBLCys156-S—SePh (1 mg) in 500 μL of aqueous buffer (70 mM CHES, 5 mM MES, 2 mM CaCl$_2$, pH 9.5). The resulting solution was placed on an end-over-end rotator. After 1 h the reaction mixture was loaded onto a PD10 Sephadex® G25 column and eluted with 70 mM HEPES, 2 mM CaCl$_2$, pH 7.0. The protein fraction was collected to afford GlcGlcGLcGlcGlcGlcGlc-SBLCys156; m/z (ES$^+$) found 27878 calcd. 27881.

EXAMPLE 21

Enzymatic extensions of SBLCys156-S-GlcNAc

A. GlcNAc-SBLCys156 (3 mg) was dissolved in 1 mL of aqueous buffer water. Phenylmethylsulfonyl fluoride (PMSF) was added (50 μL of a 100 mg/mL solution in acetonitrile; 500-fold excess). The reaction mixture was incubated at room temperature for 30 minutes and purified over a Sephadex® G-25 (PD-10) desalting column. The purity of the deactivated protein was assessed by ESI-mass spectrometry (found: 27100, calc. 27104). The protein fraction was lyophilized and re-dissolved in 1.0 mL of 0.1M sodium cacodylate buffer (pH 7.52). MnCl$_2$.4H$_2$O (3.2 mg; 16 μmol) and uridine diphosphate-galactose (UDP-galactose, 2.3 mg; 3.4 μmol, Kyowa Hakko; 30-fold excess) were added. Recombinant bovine β-1,4-galactosyltransferase from *Spodoptera Frugiperda* (EC 2.4.1.22, 100 mU, Calbiochem) was added and the reaction mixture was incubated at room temperature for 40 min to afford Galβ1,4GlcNAc-S—SBL-Cys156 (ESI-MS, found 27265, calc. 27266).

B. GDP-fucose (3 mg, Kyowa Hakku) and human $_\alpha$-1,3-fucosyltransferase from *Spodoptera Frugiperda* (EC 2.4.1.65, 10 mU, Calbiochem) were added and the reaction mixture was incubated overnight at room temperature to afford Lewis$^x$-S—SBL-Cys156 (ESI-MS, found 27410, calc. 27412).

This Example demonstrates that glycosylated proteins prepared according to the method of the invention may be further modified by reaction with suitable carbohydrate modifying enzymes, for example galactosyltransferase such as β-1,4-galactosyltransferase which selectively forms the Galβ1, 4GlcNAc linkage.

EXAMPLE 22

Sodium phenylthiosulfonate (NaPTS)

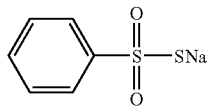

Sodium benzenesulfinate (10 g, 61 mmol) and sulfur (1.95 g, 61 mmol) were dissolved in anhydrous pyridine (60 mL) to give a yellow solution. The reaction was stirred under argon and after 1 h gave a white suspension. The reaction was filtered and washed with anhydrous diethyl ether. Recrystallisation from anhydrous ethanol afforded the title product (10.5 g, 88%) as a white crystalline solid; m p. 305-306° C. [Lit. 287° C., Sato, R.; Goto, T.; Takikawa, Y.; Takizawa, S. *Synthesis* 1980, 615]; $\delta_H$ (200 MHz, DMSO-d$_6$) 7.28-7.76 (SH, m, Ar—H).

EXAMPLE 23

2,3,4,6-Tetra-O-acetyl-β-D-glucopyranosyl phenylthiosulfonate

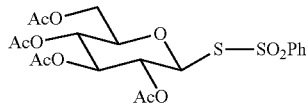

2,3,4,6-Tetra-O-acetyl-$_\alpha$-D-glucopyranosyl bromide (207 mg, 0.5 mmol) was dissolved in anhydrous acetonitrile (5 mL). To this sodium phenylthiosulfonate (201 mg, 1 mmol) and tetrabutylammonium bromide (16 mg, 0.05 mmol) were added. The resulting mixture was stirred under argon at 70° C. After a 4.5 h period, thin layer chromatography (t.l.c.) (petrol:ethyl acetate, 1:1) indicated the formation of a product (R$_f$ 0.5) with complete consumption of the starting material (R$_f$ 0.3). The solution was concentrated in vacuo. The crude solid was partitioned between dichloromethane (DCM, 20 mL) and water (20 mL), and the aqueous layer re-extracted with DCM (2×20 mL). The combined organics were washed with brine (20 mL), dried over MgSO$_4$, filtered and concentrated in vacuo. The residue was purified by flash column chromatography (petrol:ethyl acetate, 1:1) to afford the title product (225 mg, 88%) as a white crystalline solid; mp 129-130° C.; $[\alpha]_D^{25}$+51.2 (c, 1.0 in CHCl$_3$); $\nu_{max}$ (KBr) 1754 (s, C═O), 1376 (s, C═C) cm$^{-1}$; $\delta_H$; (400 MHz, C$_6$D$_6$) 1.68, 1.72, 1.73, 1.75 (4×3H, 4×s, 4×OAc), 3.09 (1H, ddd, J$_{4,5}$ 10.2 Hz, J$_{5,6}$ 2.4 Hz, J$_{5,6'}$ 4.2 Hz, H-5), 3.83 (1H, dd, J$_{5,6}$ 2.4 Hz, J$_{6,6'}$ 12.7 Hz, H-6),4.08 (1H, dd, J$_{5,6'}$ 4.2 Hz, J$_{6,6'}$ 12.6 Hz, H-6'), 5.17-5.23 (2H, m, H-2, H -4), 5.40 (1H, d, J$_{1,2}$ 10.2 Hz, H-1), 5.44 (1H, at, J9.4 Hz, H-3), 6.98-7.03 (3H, m, Ar—H), 7.90-7.92 (2H, m, Ar—H). The structure of the product was further confirmed by single crystal X-ray diffraction.

EXAMPLE 24

2,3,4,6-Tetra-O-acetyl-β-D-galactopyranosyl phenylthiosulfonate

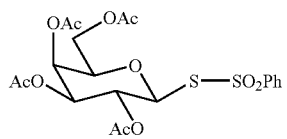

2,3,4,6-Tetra-O-acetyl-$_\alpha$-galactopyranosyl bromide (2.0 g, 5 mmol) was dissolved in anhydrous acetonitrile (80 mL). To this sodium phenylthiosulfonate (2.02 g, 10.3 mmol) and tetrabutylammonium bromide (160 mg, 0.5 mmol) were added. The resulting mixture was stirred under argon at 70° C. After a 5 h period, t.l.c. (petrol:ethyl acetate, 1:1) indicated the formation of a product (R$_f$ 0.4) with complete consumption of the starting material (R$_f$ 0.6). The solution was concentrated in vacuo. The crude oil was partitioned between DCM (50 mL) and water (50 mL), and the aqueous layer re-extracted with DCM (2×50 mL). The combined organics were washed with brine (100 mL), dried (MgSO$_4$), filtered and concentrated in vacuo. The residue was purified by flash column chromatography (petrol:ethyl acetate, 2:1) to afford the title product (1.7 g, 65%, 2 steps) as a white crystalline solid; mp 53-54° C.; $[\alpha]_D^{27}$+24.2 (c, 1.0 in CHCl$_3$); $\delta_H$ (400 MHz, CDCl$_3$) 1.98, 2.03, 2.06, 2.11 (4×3H, 4×s, 4×OAc), 3.85 (1H, dd, J$_{5,6}$ 8.8 Hz, J$_{6,6'}$ 14.0 Hz, H-6), 3.95-4.00 (2H, m, H-5, H-6), 5.11 (1H, dd, J$_{2,3}$ 9.7 Hz, J$_{3,4}$ 3.3 Hz, H-3), 5.23 (1H, at, J10.3 Hz, H-2), 5.25 (1H, d, J$_{1,2}$ 10.2 Hz, H-1), 5.43 (1H, dd, J$_{3,4}$ 3.6 Hz, J$_{4,5}$ 1.0 Hz, H-4), 7.54-7.68 (3H, m, Ar—H), 7.93-7.97 (2H, m, Ar—H).

EXAMPLE 25

Ethyl 2,3,4,6-tetra-O-acetyl-1-dithio-β-D-glucopyranosyl disulfide

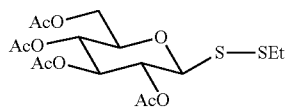

Method 1: 2,3,4,6-Tetra-O-acetyl-β-D-glucopyranosyl phenylthiosulfonate (100 mg, 0.2 mmol) and triethylamine (0.03 mL, 0.2 mmol) were dissolved in anhydrous DCM (10 mL) and stirred at room temperature RT) under an atmosphere of argon. A solution of ethane thiol (0.016 mL, 0.2 mmol) in anhydrous DCM (10 mL) was slowly added dropwise via a syringe pump over a 30 min period. After a 40 min period, t.l.c. (petrol:ethyl acetate, 1:1) indicated the formation of a major product ($R_f$ 0.5) along with complete consumption of the starting material ($R_f$ 0.3). The solution was concentrated in vacuo. The residue was purified by flash column chromatography (petrol:ethyl acetate, 1:1) to afford the title product (70 mg, 82%) as a white crystalline solid; mp 95-96° C. [Lit. 100-102° C., (Davis, B. G.; Ward, S. J.; Rendle, P. M. *Chem. Commun.* 2001, 189)]; $[\alpha]_D^{22}$-164.9 (c, 0.2 in CHCl$_3$) [Lit. $[\alpha]_D^{24}$-178.0 (c, 1.0 in MeOH) (Davis, B. G.; Ward, S. J.; Rendle, P. M. *Chem. Commun.* 2001, 189)]; $\delta_H$ (400 MHz, CDCl$_3$) 1.30 (1H, t, J7.4 Hz, CH$_3$), 2.00, 2.02, 2.03, 2.06 (4×3H, 4×s, 4×CH$_3$), 2.79 (2H, dq, $J_{CH3-H}$ 7.5 Hz, $J_{HH}$ 2.7 Hz), 3.73 (1H, ddd, $J_{4,5}$ 10.2 Hz, $J_{5,6}$ 2.5 Hz, $J_{5,6'}$ 4.8 Hz, H-5), 4.14 (1H, dd, $J_{5,6}$ 2.4 Hz, $J_{6,6'}$ 12.4 Hz, H-6), 4.22 (1H, dd, $J_{5,6'}$ 4.7 Hz, $J_{6,6'}$ 12.4 Hz, H-6'), 4.52 (1H, d, $J_{1,2}$ 9.8 Hz, H-1), 5.10 (1H, at, J9.8 Hz, H-4), 5.21-5.26 (2H, m, H-2, H-3).

Method 2: Phenyl 2,3,4,6-tetra-O-acetyl-1-selenenylsulfide-D-$_\beta$-glucopyranoside (75 mg, 0.15 mmol) and triethylamine (30 $\mu$L, 0.15 mmol) were dissolved in freshly distilled DCM (10 mL). The solution was stirred at RT under an atmosphere of argon. A solution of ethanethiol (11 $\mu$L, 0.15 mmol) in anhydrous DCM (10 mL) was added dropwise over 2.5 h. After 3 h, t.l.c. (petrol:EtOAc, 1:1) indicated the formation of a major product ($R_f$ 0.5) along with complete consumption of the starting material ($R_f$ 0.5). The solution was concentrated in vacuo. The residue was purified by flash column chromatography (petrol:EtOAc, 5:3) to afford the title product (50 mg, 82%) as a white crystalline solid.

EXAMPLE 26

Ethyl 2,3,4,6-tetra-O-acetyl-1-dithio-$_\beta$-D-galactopyranosyl disulfide

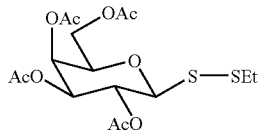

Method 1: 2,3,4,6-Tetra-O-acetyl-$_\beta$-D-galactopyranosylphenylthiosulfonate (100 mg, 0.2 mmol) and triethylamine (0.03 mL, 0.2 mmol) were dissolved in anhydrous DCM (10 mL) and stirred at RT under an atmosphere of argon. A solution of ethane thiol (0.016 mL, 0.2 mmol) in anhydrous DCM (10 mL) was slowly added dropwise via a syringe pump over a 30 min period. After a 40 min period, t.l.c. (petrol:ethyl acetate, 1:1) indicated the formation of a major product ($R_f$ 0.4) along with complete consumption of the starting material ($R_f$ 0.3). The solution was concentrated in vacuo. The residue was purified by flash column chromatography (petrol:ethyl acetate, 1:1) to afford the title product (78 mg, 91%) as a white crystalline solid; mp 65-66° C.; $[\alpha]_D^{25}$-52.1 (c, 1.4 in CHCl$_3$); $\nu_{max}$ (KBr) 1746 (s, C=O) cm$^{-1}$; $\delta_H$ (400 MHz, CDCl$_3$) 1.30 (1H, t, J7.4 Hz, CH$_3$), 1.95, 2.01, 2.02, 2.13 (4×3H, 4×s, 4×CH$_3$), 2.79 (2H, dq, $J_{CH3-H}$ 7.2 Hz, $J_{HH}$ 1.7 Hz), 3.94 (1H, td, $J_{4,5}$ 0.9 Hz, $J_{5,6}$ 6.3 Hz, $J_{5,6'}$ 7.0 Hz, H-5), 4.06 (1H, dd, $J_{5,6}$ 6.3 Hz, $J_{6,6'}$ 11.3 Hz, H-6), 4.12 (1H, dd, $J_{5,6'}$ 7.0 Hz, $J_{6,6'}$ 11.2 Hz, H-6'),4.51 (1H, d, $J_{1,2}$ 9.9 Hz,H-1), 5.05(1H, dd, $J_{2,3}$ 9.9 Hz, $J_{3,4}$ 3.6 Hz, H-3), 5.35-5.40 (2H, m, H-2, H-4).

Method 2: Phenyl 2,3,4,6-tetra-O-acetyl-1-selenenylsulfide-D-$_\beta$-galactopyranoside (75 mg, 0.15 mmol) and triethylamine (30 $\mu$L, 0.15 mmol) were dissolved in freshly distilled DCM (10 mL). The solution was stirred at RT under an atmosphere of argon. A solution of ethanethiol (11 $\mu$L, 0.15 mmol) in anhydrous DCM (10 mL) was added dropwise over a 2.5 h. After 3 h, t.l.c. (petrol:EtOAc, 1:1) indicated the formation of a major product ($R_f$ 0.5) along with complete consumption of the starting material ($R_f$ 0.5). The solution was concentrated in vacuo. The residue was purified by flash column chromatography (petrol:EtOAc, 5:3) to afford the title compound (50 mg, 82%) as a white crystalline solid.

EXAMPLE 27

Ethyl 3,4,6-tri-O-acetyl-2-acetamido-2-deoxy-$_\beta$-D-glucopyranosyl disulfide

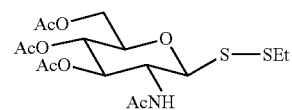

Phenyl 3,4,6-tri-O-acetyl-2-acetamido-2-deoxy-1-selenenylsulfide-D-$_\beta$-glucopyranoside (100 mg, 0.19 mmol) and triethylamine (0.03 mL, 0.19 mmol) were dissolved in freshly distilled DCM (20 mL). The solution was stirred at RT under argon. A solution of ethanethiol (0.014 mL, 0.19 mmol) in anhydrous DCM (10 mL) was added dropwise over 1 h. After 3 h, t.l.c. (EtOAc) indicated the formation of a major product ($R_f$ 0.4) along with complete consumption of the starting material ($R_f$ 0.5). The solution was concentrated in vacuo. The residue was purified by flash column chromatography (EtOAc) to afford the title product. (75 mg, 93%) as a white amorphous solid. $[\alpha]_D^{25}$-70.1 (c, 2.5 in CHCl$_3$); $\delta_H$ (400 MHz, CDCl$_3$), 1.32 (3H, d, $J_{CH,CH3}$ 6.6 Hz, CHCH$_3$), 1.96, 2.04, 2.05, 2.08 (12H, 4×s, 4×COCH$_3$), 2.82 (2H, q, J7.4 Hz, CH$_2$), 3.75 (1H, ddd, $J_{4,5}$ 10.1 Hz, $J_{5,6}$ 2.5 Hz, $J_{5,6'}$ 4.7 Hz, H-5), 4.12-4.25 (3H, m, H-2, H-6, H -6'), 4.73 (1H, at, $J_{1,2}$ 10.4 Hz, H-1), 5.10 (1H, at, J9.8 Hz, H-4), 5.30 (1H, at, J9.9 Hz, H-3), 5.70 (1H, d, $J_{NH,2}$ 9.1 Hz, NH).

EXAMPLE 28 bis-N-Acetyl-L-cysteinyl-L-serine methylester

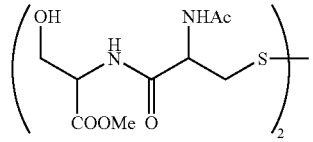

bis-L-Cysteinyl-L-serine methylester (100 mg, 0.23 mmol) was dissolved in methanol (5 mL). To this solution acetic anhydride (0.09 mL, 0.92 mmol) and pyridine (0.075 mL, 0.92 mmol) were added. After a 15 min period, t.l.c. (ethyl acetate:methanol 5:1) indicated the formation of a major product ($R_f$ 0.5) along with complete consumption of the starting material ($R_f$ 0.1). The reaction was concentrated in vacuo. The residue was purified by flash column chromatography (ethyl acetate:methanol 5:1) to afford the title product (60 mg, 50%) as a white crystalline solid; mp 145-147° C.; $[\alpha]_D^{25}$-33.4 (c, 1.0 in CHCl$_3$); $\delta_H$ (400 MHz, CDCl$_3$) 2.04 (3H, s, COCH$_3$), 2.96 (1H, dd, $J_{CH,H}$ 13.9 Hz, $J_{CH,\alpha H}$ 4.7 Hz, CysCHH), 3.23 (1H, dd, $J_{CH,H}$ 13.9 Hz, $J_{CH,\alpha H}$ 4.7 Hz, CysCHH), 3.76 (3H, s, OMe), 3.83 (1H, dd, $J_{CH,H}$ 11.4 Hz, $J_{CH,\alpha H}$ 4.1 Hz, SerCHH), 3.93 (1H, dd, $J_{CH,H}$ 11.3 Hz, $J_{CH,\alpha H}$ 4.9 Hz, SerCHH), 4.55 (1H, t, J4.3 Hz, $_\alpha$HSer), 4.87 (1H, t, J4.8, $_\alpha$HCys).

EXAMPLE 29

N-Acetyl-L-cysteinyl-L-serine methylester

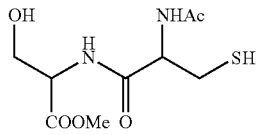 [SMILES: COC(=O)C(CO)NC(=O)C(CS)NC(C)=O]

bis-N-Acetyl-L-cysteinyl-L-serine methylester (1.92 g, 3.96 mmol) was dissolved in wet chloroform (100 mL) and methanol (10 mL) and stirred. To this stirred solution tributylphosphine (1.1 mL, 4.36 mmol) was added. After a 2 h period, t.l.c. (ethyl acetate:methanol 10:1) indicated the formation of a product (R$_f$ 0.6) along with complete consumption of the starting material (R$_f$ 0.3). The reaction was concentrated in vacuo. Recrystallisation from ethyl acetate/methanol afforded the title product (1.77 g, 93%) as a white crystalline solid; mp 127-128° C.; $[\alpha]_D^{25}$-32.0 (c, 1.0 in MeOH); $\delta_H$ (400 MHz, CDCl$_3$) 1.89 (1H, at, J8.9 Hz, SH), 2.06 (3H, s, COCH$_3$), 2.84-2.93 (1H, m, CysCHH), 2.97-3.04 (1H, m, CysCHH), 3.79 (3H, s, OMe), 3.91 (1H, dd, $J_{CH,H}$ 11.4 Hz, $J_{CH,\alpha H}$ 3.1 Hz, SerCHH), 4.03 (1H, dd, $J_{CH,H}$ 11.7 Hz, $J_{CH,\alpha H}$ 4.2 Hz, SerCHH), 4.61-4.65 (1H, m, $_\alpha$HSer), 4.71-4.76 (1H, m, $_\alpha$HCys), 6.93 (1H, d, $J_{\alpha H,NH}$ 7.8 Hz, NHCys), 7.73 (1H, d, $J_{\alpha H,NH}$ 7.4 Hz, NHSer).

EXAMPLE 30

N-Acetyl-L-cysteine (2,3,4,6-tetra-O-acetyl-1-dithio-β-D-glucopyranosyl disulfide)-L-serine methylester

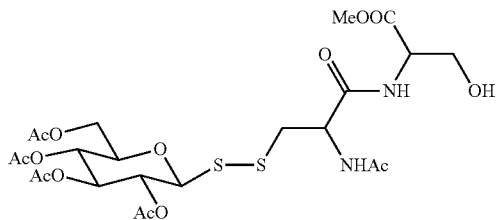 [SMILES: COC(=O)C(CO)NC(=O)C(CSSC1OC(COC(C)=O)C(OC(C)=O)C(OC(C)=O)C1OC(C)=O)NC(C)=O]

2,3,4,6-Tetra-O-acetyl-β-D-glucopyranosyl phenylthiosulfonate (61 mg, 0.12 mmol) was dissolved in anhydrous DCM (5 mL) and stirred at RT under an atmosphere of argon. To this N-acetyl-L-cysteine-L-serine methylester (32 mg, 0.12 mmol) and triethylamine (0.015 mL, 0.1 mmol) in anhydrous DCM (10 mL) and anhydrous methanol (0.5 mL) were slowly added dropwise via a syringe pump over a 4 h period. After a 5 h period, t.l.c. (ethyl acetate:methanol, 10:1) indicated the formation of a major product (R$_f$ 0.5) along with complete consumption of the starting material (R$_f$ 0.3, (t.l.c system petrol:ethyl acetate, 1:1)). The solution was concentrated in vacuo. The residue was purified by flash column chromatography (ethyl acetate:methanol, 10:1) to afford the title product (75 mg, 99%) as a white crystalline solid; mp 126-128° C. [Lit. 125-128° C. (Davis, B. G.; Ward, S. J.; Rendle, P. M. *Chem. Commun.* 2001, 189)]; $[\alpha]_D^{25}$-47.9 (c, 0.7 in CHCl$_3$) [Lit. $[\alpha]_D^{24}$-178.0 (c, 1.0 in MeOH) (Davis, B. G.; Ward, S. J.; Rendle, P. M. *Chem. Commun.* 2001, 189)]; $\delta_H$ (400 MHz, CDCl$_3$) 2.03, 2.06, 2.07, 2.11 (5×3H, 4×s, 5×CH$_3$), 3.05 (1H, dd, $J_{CH,H}$ 13.9 Hz, $J_{CH,\alpha H}$ 8.8 Hz, CysCHH), 3.28 (1H, dd, $J_{CH,H}$ 13.9 Hz, $J_{CH,\alpha H}$ 4.8 Hz, CysCHH), 3.80 (3H, s, OMe), 3.89 (1H, ddd, $J_{4,5}$ 10.0 Hz, $J_{5,6}$ 2.2 Hz, $J_{5,6'}$ 4.1 Hz, H-5), 3.94 (1H, dd, $J_{CH,H}$ 11.7 Hz, $J_{CH,\alpha H}$ 3.0 Hz, SerCHH), 4.00 (1H, dd, $J_{CH,H}$ 13.8 Hz, $J_{CH,\alpha H}$ 3.7 Hz, SerCHH), 4.23 (1H, dd, $J_{5,6}$ 4.2 Hz, $J_{6,6'}$ 12.4 Hz, H-6), 4.38 (1H, dd, $J_{5,6'}$ 2.0 Hz, $J_{6,6'}$ 12.5 Hz, H-6'), 4.62-4.65 (1H, m, $_\alpha$HSer), 4.64 (1H, d, $J_{1,2}$ 9.5 Hz, H-1), 4.90-4.94 (1H, m, $_\alpha$HCys), 5.18 (1H, at, J10.1 Hz, H-4), 5.24-5.29 (2H, m, H-2, H-3), 6.94 (1H, d, $J_{NH,H}$ 7.9 Hz, NHAc), 7.52 (1H, d, $J_{NH,H}$ 7.6 Hz, NHSer).

EXAMPLE 31

N-Acetyl-L-cysteine (2,3,4,6-tetra-O-acetyl-1-dithio-β-D-galactopyranosyl disulfide)-L-serine methylester

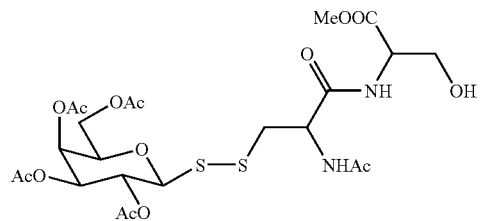 [SMILES: COC(=O)C(CO)NC(=O)C(CSSC1OC(COC(C)=O)C(OC(C)=O)C(OC(C)=O)C1OC(C)=O)NC(C)=O]

2,3,4,6-Tetra-O-acetyl-β-D-galactopyranosyl phenylthiosulfonate (50 mg, 0.1 mmol) was dissolved in anhydrous DCM (5 mL) and stirred at RT under an atmosphere of argon. A solution of N-acetyl-L-cysteine-L-serine methylester (31 mg, 0.12 mmol) and triethylamine (0.015 mL, 0.11 mmol) in anhydrous DCM (10 mL) and anhydrous methanol (0.5 mL) was slowly added dropwise via a syringe pump over a 2 h period. After a 2 h period, t.l.c. (ethyl acetate:methanol, 10:1) indicated the formation of a major product (R$_f$ 0.5) along with complete consumption of the starting material (R$_f$ 0.5, t.l.c system petrol:ethyl acetate, 1:1). The solution was concentrated in vacuo. The residue was purified by flash column chromatography (ethyl acetate:methanol, 10:1) to afford the title product (59 mg, 95%) as a white amorphous solid; $[\alpha]_D^{25}$-48.8 (c, 0.25 in CHCl$_3$); $\delta_H$ (400 MHz, CDCl$_3$) 1.99, 2.04, 2.05, 2.08, 2.18 (5×3H, 4×s, 5×CH$_3$), 2.80 (1H, bs, OH), 2.99 (1H, dd, $J_{CH,H}$ 14.1 Hz, $J_{CH,\alpha H}$ 9.2 Hz, CysCHH), 3.32, 3.77 (3H, s, OMe), 3.92 (1H, dd, $J_{CH,H}$ 11.7 Hz, $J_{CH,\alpha H}$ 3.0 Hz, SerCHH), 4.01 (1H, dd, $J_{CH,H}$ 11.7 Hz, $J_{CH,\alpha H}$ 3.7 Hz, SerCHH), 4.06-4.14 (2H, m, H-5, H-6), 4.20-4.26 (1H, m, H-6'), 4.61-4.63 (1H, m, $_\alpha$HSer), 4.65 (1H, d, $J_{1,2}$ 9.8 Hz, H-1), 4.88-4.93 (1H, m, $_\alpha$HCys), 5.11 (1H, dd, $J_{2,3}$ 9.8 Hz, $J_{3,4}$ 3.3 Hz, H-3), 5.42-5.47 (2H, m, H-2, H-4), 6.68 (1H, d, $J_{NH,H}$ 7.8 Hz, NHAc), 7.28 (1H, d, $J_{NH,H}$ 8.1 Hz, NHSer).

EXAMPLE 32

2,3,4,6-Tetra-O-benzyl-α-D-glucopyranosyl bromide

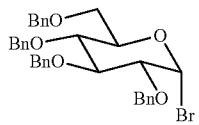

2,3,4,6-Tetra-O-benzyl-D-glucopyranose (1.0 g, 1.9 mmol) was dissolved in anhydrous DCM (6 mL) and anhydrous DMF (0.4 mL) under argon. The resulting solution was stirred at 0° C. Oxalyl bromide (4 mL, 2M in DCM, 24 mmol) was added dropwise over a 5 min period. The reaction was stirred at RT. After a 40 min period, t.l.c. (petrol:ethyl acetate, 2:1) indicated the formation of a major product ($R_f$ 0.7). The reaction was cooled to 0° C. and quenched with ice cold water (30 mL) added over a 5 min period. The reaction was partitioned between DCM (20 mL) and water. The aqueous layer was re-extracted with DCM (3×20 mL), the combined organic layers were washed with brine (40 mL), dried ($MgSO_4$), filtered and concentrated in vacuo to afford the title product (1.10 g, 95%) as a crude yellow oil; $\delta_H$ (400 MHz, $CDCl_3$), 3.57 (1H, dd, $J_{1,2}$ 3.5 Hz, $J_{2,3}$ 9.1 Hz, H-2), 3.68 (1H, dd, $J_{5,6}$ 2.1 Hz, $J_{6,6'}$ 11.0 Hz, H-6), 3.79-3.84 (2H, m, H-4, H-6'), 4.07 (1H, at, J9.1 Hz, H-3), 4.07-4.11 (1H, m, H-5), 4.47-4.62 (3H, m, $PhCH_2$), 4.74 (s, 2H, $PhCH_2$), 4.84-4.89 (2H, m, $PhCH_2$), 5.10 (1H, d, J11.1 Hz, $PhCH_2$), 6.46 (1H, d, H-1), 7.15-7.41 (20H, m, Ar—H).

EXAMPLE 33

2,3,4,6-Tetra-O-benzyl-β-D-glucopyranosyl phenylthiosulfonate

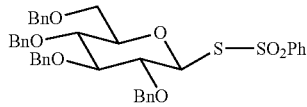

2,3,4,6-Tetra-O-benzyl-D-α-glucopyranosyl bromide (3.55 g, 5.88 mmol) and sodium phenylthiosulfonate (4.76 g, 24.3 mmol) were dissolved in anhydrous 1,4 dioxane (90 mL). The reaction was heated to 70° C. under argon. After 20 h, t.l.c. (petrol:ethyl acetate, 2:1) indicated the formation of a major product $R_f$ 0.6) with complete consumption of the starting material ($R_f$ 0.7). The reaction was cooled to RT and filtered, the precipitate was washed with petrol/ethyl acetate and the filtrate concentrated in vacuo. The residue was purified by flash column chromatography (petrol:ethyl acetate, 4:1) to afford 2,3,4,6-tetra-O-benzyl-D-glucopyranosyl phenylthiosulfonate (3.18 g, 78%) as a white viscous gum as a mixture of α,β compounds in β:α ratio of 3:1. Selective re-crystallisation from ethyl acetate/petrol afforded pure 2,3,4,6-tetra-O-benzyl-β-D-glucopyranosyl phenylthiosulfonate as a white crystalline solid; m.p. 106-108° C.; $[\alpha]_D^{22}$+21.4 (c, 0.35 in $CHCl_3$); $\delta_H$(500 MHz, $C_6D_6$) 3.21 (1H, ddd, $J_{4,5}$ 9.7 Hz, $J_{5,6}$ 1.4 Hz, $J_{5,6'}$ 3.8 Hz, H-5), 3.29 (1H, dd, $J_{5,6}$ 1.4 Hz, $J_{6,6'}$ 11.1 Hz, H-6), 3.34 (1H, dd, $J_{1,2}$ 9.9 Hz, $J_{2,3}$ 8.7 Hz, H-2), 3.49 (1H, dd, $J_{5,6}$ 3.8 Hz, $J_{6,6'}$ 11.1 Hz, H-6'), 3.51 (1H, at, J9.4 Hz, H-3), 3.60 (1H, at, J9.4 Hz, H-4), 4.15, 4.25 (2H, ABq, J12.1 Hz, $PhCH_2$), 4.52, 4.58 (21 ABq, J11.0 Hz, $PhCH_2$), 4.72, 4.76 (2H, ABq, J11.3 Hz, $PhCH_2$), 4.78, 4.52 (2H, ABq, J11.3 Hz, $PhCH_2$), 5.25 (1H, d, $J_{1,2}$ 10.2 Hz, H-1), 6.82-6.88 (3H, m, Ar—H), 7.05-7.26 (20H, m, Ar—H), 7.96-7.98 (2H, m, Ar—H).

EXAMPLE 34

Ethyl 2,3,4,6-tetra-O-benzyl-1-dithio-β-D-glucopyranosyl disulfide

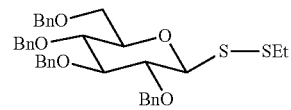

2,3,4,6-Tetra-O-acetyl-β-D-glucopyranosyl phenylthiosulfonate (100 mg, 0.14 mmol) and triethylamine (0.02 mL, 0.14 mmol) were dissolved in anhydrous DCM (10 mL) and stirred at RT under an atmosphere of argon. To this ethane thiol (11 μL, 0.14 mmol) in anhydrous DCM (10 mL) was slowly added dropwise via a syringe pump over a 90 min period. After a 90 min period, t.l.c. (petrol:ethyl acetate, 6:1) indicated the formation of a major product $R_f$ 0.4) along with complete consumption of the starting material ($R_f$ 0.2). The solution was concentrated in vacuo. The residue was purified by flash column chromatography (petrol:ethyl acetate, 7:1) to afford the title product (83 mg, 95%) as a clear oil; $[\alpha]_D^{22}$-164.9 (c, 0.2 in $CHCl_3$) [Lit. $[\alpha]_D^{25}$-80.0 (c, 3.0 in MeOH) (Davis, B. G.; Ward, S. J.; Rendle, P. M. Chem. Commun. 2001, 189)]; $\delta_H$ (400 MHz, $CDCl_3$) 1.22 (1H, t, J7.3 Hz, $CH_3$), 2.68-2.86 (2H, m, $CH_2$), 3.24 (1H, ddd, $J_{4,5}$ 9.7 Hz, $J_{5,6}$ 3.3 Hz, $J_{5,6'}$ 2.1 Hz, H-5), 3.56-3.60 (2H, m, H-6, H-6'), 3.61 (1H, at, J9.1 Hz, H-3), 3.72 (1H, at, J9.4 Hz H-4), 3.89 (1H, at, J9.1 Hz, H-2), 4.34 (1H, d, $J_{1,2}$ 9.7 Hz, H-1), 4.37, 4.31 (2H, Abq, J12.2 Hz, $PhCH_2$), 4.56, 4.83 (2H, Abq, J11.3 Hz, $PhCH_2$), 4.77-4.83 (2H, m, $PhCH_2$), 4.90 (1H, d, J11.1 Hz, PhCHH), 4.97 (1H, d, J10.7 Hz, PhCHH), 7.07-7.21 (14H, m, Ar—H), 7.25-7.27 (2H, m, Ar—H), 7.29-7.31 (2H, m, Ar—H), 7.36-7.38 (2H, m, Ar—H).

EXAMPLE 35

N-Acetyl-L-cysteine (2,3,4,6-tetra-O-benzyl-1-dithio-β-D-glucopyranosyl disulfide)-L-serine methylester

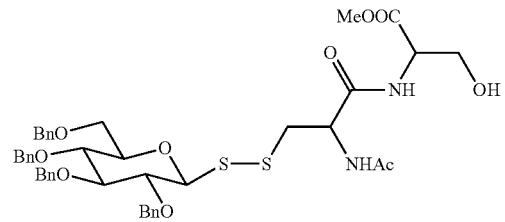 [SMILES: COC(=O)C(CO)NC(=O)C(CSSC1OC(COCc2ccccc2)C(OCc2ccccc2)C(OCc2ccccc2)C1OCc1ccccc1)NC(C)=O]

2,3,4,6-Tetra-O-benzyl-β-D-glucopyranosyl phenylthiosulfonate (50 mg, 0.07 mmol) was dissolved in anhydrous DCM (5 mL) and stirred at RT under an atmosphere of Ar. To this N-acetyl-L-cysteine-L-serine methylester (19 mg, 0.07 mmol) and triethylamine (11 μL, 0.08 mmol) in anhydrous DCM (5 mL) and anhydrous methanol (0.5 mL) was slowly added dropwise via a syringe pump over a 5 h period. After a 5 h period, t.l.c. (ethyl acetate) indicated the formation of a major product ($R_f$ 0.6) along with complete consumption of the starting material ($R_f$ 0.9). The solution was concentrated in vacuo. The residue was purified by flash column chromatography (ethyl acetate) to afford the title product (48 mg, 82%) as a white crystalline solid; mp 96-97° C.; $[\alpha]_D^{22}$+56.2 (c, 1 in CHCl$_3$); $\delta_H$ (400 MHz, CDCl$_3$) 2.03 (3H, s, COCH$_3$), 3.19 (1H, dd, $J_{CH,H}$ 14.0 Hz, $J_{CH,\alpha H}$ 8.3 Hz, CysCHH), 3.37 (1H, dd, $J_{CH,H}$ 14.3 Hz, $J_{CH,\alpha H}$ 6.0 Hz, CysCHH), 3.64 (1H, ddd, $J_{4,5}$ 9.6 Hz, $J_{5,6}$ 1.8 Hz, $J_{5,6'}$ 3.9 Hz, H-5), 3.72 (1H, at, J9.2 Hz, H-4), 3.77 (1H, at, J8.8 Hz, H-3), 3.82 (3H, s, OMe), 3.84-3.90 (4H, m, SerCHH, H-2, H-6, H -6'), 3.96 (1H, dd, $J_{CH,H}$ 11.7 Hz, $J_{CH,\alpha H}$ 3.3 Hz, SerCHH), 4.50 (1H, d, $J_{1,2}$ 9.6 Hz, H-1), 4.51, 4.70 (2H, ABq, J11.6 Hz, PhCH$_2$), 4.55, 4.85 (2H, ABq, J10.4 Hz, PhCH$_2$), 4.59-4.62 (1H, m, αHSer), 4.81, 4.87 (2H, ABq, J10.6 Hz, PhCH$_2$), 4.91, 4.97 (2H, ABq, J11.0 Hz, PhCH$_2$), 4.93-4.98 (1H, m, αHCys), 6.88 (1H, bd, $J_{NH,H}$ 7.9 Hz, NHAc), 7.13-7.39 (20H, m 20×Ar—C), 7.48 (1H, d, $J_{NH,H}$ 7.6 Hz, NHSer).

EXAMPLE 36

2,3,6-Tri-O-acetyl-4-O-(2,3,6-tri-O-acetyl-4-O-(2,3,4,6-tetra-O-acetyl-α-O-glucopyranosyl)-α-D-glucopyranosyl)-β-D-glucopyranosyl phenylthiosulfonate

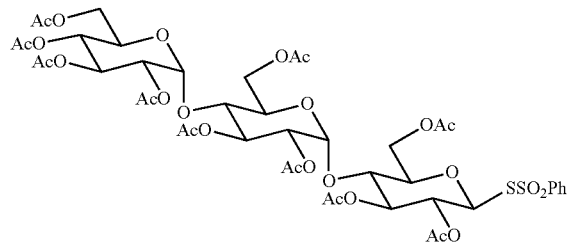

2,3,6-Tri-O-acetyl-4-O-(2,3,6-tri-O-acetyl-4-O-(2,3,4,6-tetra-O-acetyl-α-O-glucopyranosyl)-α-D-glucopyranosyl)-α-D-glucopyranosyl bromide (200 mg, 0.21 mmol) was dissolved in anhydrous acetonitrile (10 mL). To this sodium benzenethiosulfonate (80 mg, 0.41 mmol) and tetrabutylammonium iodide (10 mg, 0.02 mmol) were added. The resulting mixture was stirred under argon at 70° C. After a 2 h period, t.l.c. (petrol:ethyl acetate, 1:2) indicated the formation of a UV active product ($R_f$ 0.5) with complete consumption of the starting material ($R_f$ 0.5). At which point the solution was allowed to cool to RT and filtered, the filtrate was concentrated in vacuo. The residue was purified by flash column chromatography (petrol:ethyl acetate, 1:2) to afford the title product (140 mg, 62%) as a white amorphous solid; $[\alpha]_D^{22}$+69.9 (c, 0.75 in CHCl$_3$); $\delta_H$ (500 MHz, CDCl$_3$) 2.03, 2.04, 2.06, 2.08, 2.11, 2.15, 2.19, (30H, 10×COCH$_3$), 3.77-3.79 (1H, m, H-5a), 3.94-4.00 (4H, m, H-4a, H-4c, H-5b, H-5c), 4.10 (1H, dd, $J_{5,6}$ 2.1 Hz, $J_{6,6'}$ 12.4 Hz, H-6b), 4.17-4.22 (3H, m, H-6a, H-6c, H-6a'), 4.29 (1H, dd, $J_{5,6}$ 3.3 Hz, $J_{6,6'}$ 12.6 Hz, H-6b'), 4.46 (1H, dd, $J_{5,6}$ 1.9 Hz, $J_{6,6'}$ 12.4 Hz, H-6c'), 4.76 (1H, dd, $J_{1,2}$ 3.9 Hz, $J_{2,3}$ 10.4 Hz, H-2a), 4.89-4.94 (2H, m, H-2b, H-2c), 5.12 (1H, at, J9.9 Hz, H-4b), 5.28 (1H, d, $J_{1,2}$ 3.8 Hz, H-1a), 5.34 (1H, d, $J_{1,2}$ 9.7 Hz, H-1c), 5.37 (1H, at, J9.1 Hz, H-3c), 5.41 (1H, at, J10.1 Hz, H-3b), 5.41-5.45 (2H, m, H-1b, H-3a), 7.62-7.65 (2H, m, Ar—H), 7.71 (1H, m, Ar—H), 8.00-8.02 (2H, m, Ar—H).

EXAMPLE 37

Ethyl 2,3,6-tri-O-acetyl-4-O-(2,3,6-tri-O-acetyl-4-O-(2,3,4,6-tetra-O-acetyl-α-O-glucopyranosyl)-α-D-glucopyranosyl)-1-dithio-β-D-glucopyranosyl disulfide

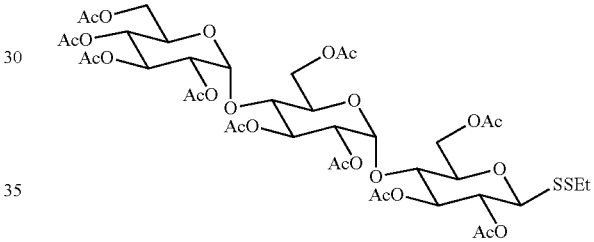

2,3,6-Tri-O-acetyl-4-O-(2,3,6-tri-O-acetyl-4-O-(2,3,4,6-tetra-O-acetyl-α-O-glucopyranosyl)-α-D-glucopyranosyl)-β-D-glucopyranosyl phenylthiosulfonate (50 mg, 0.05 mmol) was dissolved in anhydrous DCM (10 mL) and stirred at RT under an atmosphere of argon. A solution of triethylamine (7 μL, 0.05 mmol) and ethane thiol (3 μL, 0.05 mmol) and anhydrous DCM (10 mL) was slowly added dropwise via a syringe pump over a 1 h period. After a 1 h period, t.l.c. (petrol:ethyl acetate, 1:2) indicated the formation of a major product ($R_f$ 0.6) along with complete consumption of the starting material ($R_f$ 0.4). The solution was concentrated in vacuo. The residue was purified by flash column chromatography (petrol:ethyl acetate, 1:2) to afford ethyl the title product (43 mg, 93%) as a clear oil; $[\alpha]_D^{24}$+26.4 (c, 1.5 in CHCl$_3$); $\delta_H$ (500 MHz, CDCl$_3$) 1.30 (1H, t, J7.2 Hz, CH$_3$), 2.04, 2.05, 2.06, 2.07, 2.10, 2.14, 2.19, 2.20 (30H, 8×s, 10×COCH$_3$), 2.75-2.87 (2H, m, CH$_2$CH$_3$), 3.77-3.81 (1H, m, H-5a), 3.96-4.00 (3H, m, H-4b, H-5c, H-5b), 4.03 (1H, at, J9.3 Hz, H-4a), 4.10 (1H, dd, $J_{5,6}$ 2.3 Hz, $J_{6,6'}$ 12.6 Hz, H-6c), 4.22 (1H, dd, $J_{5,6}$ 2.9 Hz, $J_{6,6'}$ 12.4 Hz, H-6b), 4.29 (1H, dd, $J_{5,6}$ 3.7 Hz, $J_{6,6'}$ 12.4 Hz, H-6'c), 4.33 (1H, dd, $J_{5,6}$ 4.4 Hz, $J_{6,6'}$ 12.4 Hz, H-6a), 4.51 (1H, dd, $J_{5,6'}$ 1.8 Hz, $J_{6,6'}$ 12.4 Hz, H-6b', 4.57 (1H, dd, $J_{5,6}$ 2.3 Hz, $J_{6,6'}$ 12.4 Hz, H-6a'), 4.58 (1H, d, $J_{1,2}$ 9.9 Hz, H-1a), 4.79 (1H, dd, $J_{1,2}$ 4.1 Hz, $J_{2,3}$ 10.6 Hz, H-2b), 4.90 (1H, dd, $J_{1,2}$ 4.3 Hz, $J_{2,3}$ 10.4 Hz, H-2c), 5.11 (1H, at, J9.9 Hz, H-4c), 5.16 (1H, at, J9.5 Hz, H-2a), 5.33 (1H, d, $J_{1,2}$ 4.1 Hz, H-1b), 5.37 (1H, at, J8.9 Hz, H-3a), 5.38- 5.44 (2H, m, H-3b, H-3c), 5.45 (1H, d, $J_{1,2}$ 4.1 Hz, H-1c).

EXAMPLE 38

N-Butoxycarbonyl-L-cysteine (2,3,6-tri-O-acetyl-4-O-(2,3,6-tri-O-acetyl-4-O-(2,3,4,6-tetra-O-acetyl-α-O-glucopyranosyl)-α-D-glucopyranosyl)-1-dithio-β-D-glucopyranosyl disulfide)-L-serine methylester

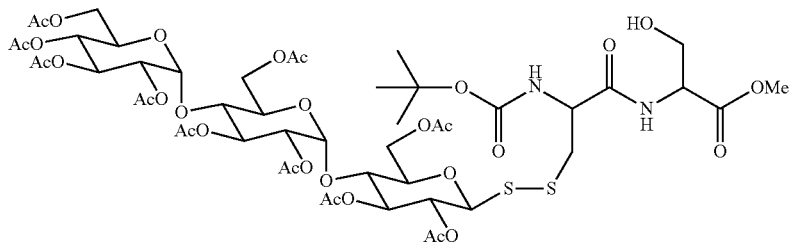 [SMILES: COC(=O)C(CO)NC(=O)C(CSSC1OC(COC(C)=O)C(OC2OC(COC(C)=O)C(OC3OC(COC(C)=O)C(OC(C)=O)C(OC(C)=O)C3OC(C)=O)C(OC(C)=O)C2OC(C)=O)C(OC(C)=O)C1OC(C)=O)NC(=O)OC(C)(C)C]

2,3,6-Tri-O-acetyl-4-O-(2,3,6-tri-O-acetyl-4-O-(2,3,4,6-tetra-O-acetyl-α-O-glucopyranosyl)-α-D-glucopyranosyl)-β-D-glucopyranosyl phenylthiosulfonate (89 mg, 0.08 mmol) was dissolved in anhydrous DCM (5 mL) and stirred at RT under an atmosphere of argon. A solution of triethylamine (0.014 mL, 0.2 mmol) and N-butoxycarbonyl-L-cysteinyl-L-serine methylester (30 mg, 0.09 mmol) in anhydrous DCM (10 mL) and anhydrous methanol (1 mL) was slowly added dropwise via a syringe pump over a 3 h period. After a 3 h period, t.l.c. (ethyl acetate) indicated the formation of a major product ($R_f$ 0.6) along with complete consumption of the starting material ($R_f$ 0.7). The solution was concentrated in vacuo. The residue was purified by flash column chromatography (ethyl acetate) to afford the title product (66 mg, 74%) as an amorphous white solid; $[\alpha]_D^{24}$ +25.1 (c, 1.25 in CHCl$_3$); $\delta_H$ (500 MHz, CDCl$_3$) 1.47 (9H, s, C(CH$_3$)$_3$), 2.00, 2.01, 2.02, 2.03, 2.06, 2.09, 2.15, 2.18 (30H, 8×s, 10×COCH$_3$), 2.75-2.87 (1H, m, CHHCys), 3.16-3.19 (1H, m, CHHCys), 3.27 (1H, t, J6.2 Hz, OH), 3.81 (3H, s, OMe), 3.83 -3.85 (1H, m, H-5a), 3.92-4.01 (6H, m, H-4b, H-5b, H-5c, H-6a, H-6a', CHHSer), 4.06 (1H, dd, $J_{5,6}$ 2.2 Hz, $J_{6,6'}$ 12.2 Hz, H-6c), 4.09-4.16 (2H, m, H-4a, H-6b), 4.25 (1H, dd, $J_{5,6}$ 3.2 Hz, $J_{6,6'}$ 12.3 Hz, H-6c'), 4.39-4.41 (1H, m, CHHSer), 4.52-4.67 (4H, m, αHSer, αHCys, H-1a, H-6'b), 4.74 (1H, dd, $J_{1,2}$ 4.1 Hz, $J_{2,3}$ 10.3 Hz, H-2b), 4.85 (1H, dd, $J_{1,2}$ 3.7 Hz, $J_{2,3}$ 10.5 Hz, H-2c), 5.07 (1H, at, J9.9 HZ, H-4c), 5.11-5.13 (1H, m, H-2a), 5.28 (1H, d, $J_{1,2}$ 4.1 Hz, H-1b), 5.32-5.41 (4H, m, H-3a, H-3b, H-3c, NHCys), 5.42 (1H, d, $J_{1,2}$ 3.9 Hz, H-1c), 7.25 (1H, bd, $J_{NH,\alpha H}$ 6.7 Hz, NHSer).

EXAMPLE 39

Phenyl 2,3,6-tri-O-acetyl-1-selenenylsulfide-4-O-(2,3,6-tri-O-acetyl-4-O-(2,3,4,6-tetra-O-acetyl-α-O-glucopyranosyl)-α-D-glucopyranosyl)-β-D-glucopyranoside

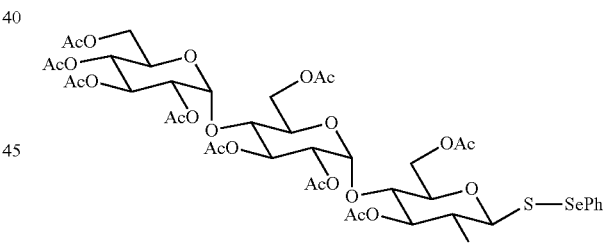

2,3,6-Tri-O-acetyl-4-O-(2,3,6-tri-O-acetyl-4-O-(2,3,4,6-tetra-O-acetyl-α-O-glucopyranosyl)-α-D-glucopyranosyl)-β-D-glucopyranosylthiol (500 mg, 0.53 mmol) and phenyl selenium bromide (200 mg, 0.9 mmol) were dissolved in anhydrous DCM (20 ml). After a 5 min period, t.l.c. (petrol: ethyl acetate 1:2) indicated the formation of a major product ($R_f$ 0.4) along with complete consumption of the staring material ($R_f$ 0.3). The reaction was quenched with the addition of triethylamine (5 ml) and then concentrated in vacuo. The residue was purified by flash column chromatography (petrol: ethyl acetate 1:2) to afford the title product (527 mg, 91%) as an amorphous off white solid; $[\alpha]_D^{25}$-2.6 (c, 1.0 in CHCl$_3$); $\delta_H$(400 MHz, CDCl$_3$), 1.99, 2.01, 2.02, 2.04, 2.06, 2.10, 2.14 (30H, 9×s, 10×OAc), 3.79 (1H, dat, J$_{4,5}$ 9.7 Hz, J3.4 Hz, H-5a), 3.92 (3H, m, H4b, H-5b, H-5c), 4.00 (1H, at, J9.3 Hz, H-4a), 4.05 (1H, dd, J$_{5,6}$ 2.8 Hz, J$_{6,6'}$ 12.8 Hz, H-6c), 4.15 (1H, dd, J$_{5,6}$ 2.8 Hz, J$_{6,6'}$ 12.6 Hz, H-6b), 4.22 (1H, dd, J$_{5,6}$ 3.7 Hz, J$_{6,6'}$ 12.0 Hz, H-6a), 4.25 (1H, dd, J$_{5,6}$ 3.3 Hz, J$_{6,6'}$ 12.0 Hz, H-6c'), 4.42-4.46 (2H, m, H-6a', H-6b'), 4.66 (1H, d, J$_{1,2}$ 9.9 Hz, H-1a), 4.74 (1H, dd, J$_{1,2}$ 4.1 Hz, J$_{2,3}$ 10.4 Hz, H-2b), 4.86 (1H, dd, J$_{1,2}$ 4.1 Hz, J$_{2,3}$ 10.5 Hz, H-2c), 5.06 (1H, at, J9.6 Hz, H-4c), 5.07 (1H, at, J9.8 Hz, H-2a), 5.27 (1H, d, J$_{1,2}$ 4.4 Hz, H-1b), 5.32-5.39 (3H, m, H-3a, H-3b, H-3c), 5.41 (1H, d, J$_{1,2}$ 4.2 Hz, H-1c), 7.27-7.29 (3H, m, Ar—H), 7.64-7.67 (2H, m, Ar—H).

EXAMPLE 40 bis-N-Butoxycarbonyl-L-cysteinyl-L-threonine methylester

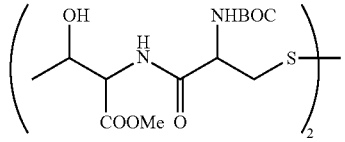

bis-N-Butoxycarbonyl-L-Cysteine (4.0 g, 9.1 mmol), L-threonine methylester (2.42 g, 18.2 mmol), DCC (3.75 g, 18.2 mmol), HOBt (2.46 g, 18.2 mmol) and DIPEA (2.5 ml, 18.2 mmol) was dissolved in freshly distilled DCM (150 mL). After a 18 h period, t.l.c. (ethyl acetate:methanol 9:1) indicated the formation of a major product (R$_f$ 0.5) along with complete consumption of the starting material (R$_f$ 0.0). The reaction was diluted with water (2×100 ml) and the phases were partitioned. The organics were washed with brine (100 ml), dried (MgSO$_4$), filtered and the solvent removed in vacuo. The residue was purified by flash column chromatography (ethyl acetate:methanol 9:1), and recrystallisation from methanoydiethyl ether afforded the title product (3.26 g, 60%) as a white crystalline solid; mp 145-147° C.; $[\alpha]_D^{25}$+ 20.8 (c, 1.0 in CHCl$_3$); $\delta_H$ (400 MHz, CDCl$_3$), 1.23 (3H, d, J$_{CH,CH3}$ 6.6 Hz, CHCH$_3$), 1.44 (9H, s, C(CH$_3$)$_3$), 3.11-3.12 (2H, m, CH$_2$Cys), 3.26 (1H, bs, OH), 3.75 (3H, s, OMe), 4.32-4.36 (1H, m, CHCH$_3$), 4.61 (dd, J$_{NH,\alpha Thr}$ 8.7 Hz, J$_{\alpha H,CHCH3}$ 2.15 Hz, CHCH$_3$), 4.63-4.68 (1H, m, αCys), 5.75 (1H, d, J$_{NH,\alpha HCys}$ 7.4 Hz, NHCys), 7.56 (1H, d, J$_{NH,\alpha Thr}$ 8.6 Hz, NHThr).

EXAMPLE 41

N-Butoxycarbonyl-L-cysteinyl-L-threonine methylester

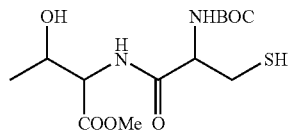

bis-N-Butoxycarbonyl-L-cysteinyl-L-threonine methylester (2.0 g, 3.3 mmol) was dissolved in wet chloroform (100 mL) and methanol (10 mL) and stirred. To this stirred solution tributylphosphine (1.0 mL, 4.0 mmol) was added. After a 2 h period, t.l.c. (ethyl acetate:methanol 9:1) indicated the formation of a product R$_f$ 0.8) along with complete consumption of the starting material (R$_f$ 0.7). The reaction was concentrated in vacuo. The residue was purified by flash column chromatography (ethyl acetate) to afford the title product (2.0 g, 99%) as a white foam; $[\alpha]_D^{25}$ 11.4 (c, 1.0 in CHCl$_3$); $\delta_H$ (400 MHz, CDCl$_3$) 1.09 (3H, d, J$_{CH,CH3}$ 6.4 Hz, CH$_3$), 1.34 (9H, s, C(CH$_3$)$_3$), 1.65 (1H, at, J8.7 Hz, SH), 2.72-2.89 (2H, m, CH$_2$), 3.66 (3H, s, OMe), 3.96 (1H, m, OH), 4.24-4.28 (1H, m, CHCH$_3$), 4.34-4.36 (1H, m, αHCys), 4.49 (1H, dd, J$_{\alpha HThr,NH}$ 8.5 Hz, J$_{\alpha Ethr,CHCH3}$ 2.7 Hz, αHThr), 5.82 (1H, d, J$_{\alpha HCys,NH}$ 8.2 Hz, NHCys), 7.38 (1H, d, J$_{\alpha HThr,NH}$ 8.5 Hz, NHThr).

EXAMPLE 42

N-Butoxycarbonyl-L-cysteine (2,3,4,6-tetra-O-acetyl-1-dithio-β-D-glucopyranosyl disulfide)-L-threonine methylester

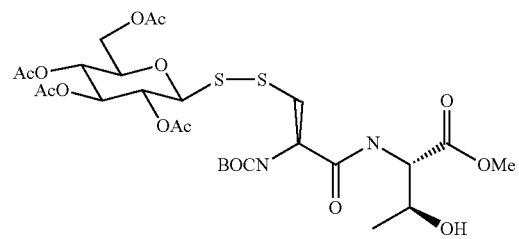

Phenyl 2,3,4,6-tetra-O-acetyl-1-selenenylsulfide-D-β-glucopyranoside (130 mg, 0.25 mmol) and triethylamine (0.02 mL, 0.18 mmol) were dissolved in freshly distilled DCM (10 mL). The resulting solution was stirred at RT. A solution of N-butoxycarbonyl-L-cysteine-L-threonine methylester (30 mg, 0.089 mmol) in anhydrous methanol (4 mL) was added slowly to the above solution. After a 10 min period, t.l.c. (petrol:ethyl acetate, 1:2) indicated the formation of a product (R$_f$ 0.2) along with complete consumption of the starting material (R$_f$ 0.5). The solution was concentrated in vacuo. The residue was purified by flash column chromatography (petrol:ethyl acetate, 1:2) to afford the title product (32 mg, 51%) as a white amorphous solid; $[\alpha]_D^{25}$-81.2 (c, 0.25 in CHCl$_3$); $\delta_H$ (400 MHz, CDCl$_3$) 1.28 (3H, d, J$_{CHC3}$ 6.7 Hz, CHCH$_3$), 1.51 (9H, s, C(CH$_3$)$_3$), 2.06, 2.08, 2.10 2.14 (12H, 4×s, 4×OAc), 2.86 (1H, bs, OH), 3.06 (1H, dd, J$_{CH\alpha H}$ 8.8 Hz, J$_{CHCH}$ 13.4 Hz, CHHCys), 3.31 (1H, dd, J$_{CH\alpha H}$ 4.2 Hz, J$_{CHCH}$ 13.1 Hz, CHHCys), 3.82 (3H, s, OCH), 3.87-3.89 (1H, m, H-5), 4.32-4.38 (2H, m, H-6, H-6'), 4.39 (1H, dd, J$_{CHCH3}$ 6.4 Hz, J$_{CH\alpha H}$ 2.5 Hz, CHOH), 4.60-4.65 (3H, m, H-1, αHThr, αHCys), 5.20-5.32 (3H, m, H-2, H-3, H-4), 5.42 (1H, d, J$_{NH\alpha H}$ 8.0 Hz, NHCys), 7.12 (1H, d, J$_{NH\alpha H}$ 8.9 Hz, NHThr).

EXAMPLE 43

N-butoxycarbonyl-L-cysteine (2,3,4,6-tetra-O-acetyl-1-dithio-β-D-galactopyranosyl disulfide)-L-threonine methylester

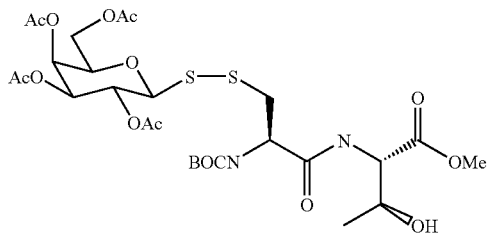

Phenyl 2,3,4,6-tetra-O-acetyl-1-selenenylsulfide-D-β-galactopyranoside (140 mg, 0.27 mmol) and triethylamine (0.01 mL, 0.089 mmol) were dissolved in freshly distilled DCM (5 mL). The resulting solution was stirred at RT. A solution of N-butoxycarbonyl-L-cysteine-L-threonine methylester (26 mg, 0.077 mmol) in anhydrous DCM (5 mL) and anhydrous methanol (4 mL) was added slowly to the above solution. After a 10 min period, t.l.c. (petrol:ethyl acetate, 1:2) indicated the formation of a product ($R_f$ 0.2) along with complete consumption of the starting material ($R_f$ 0.6). The solution was concentrated in vacuo. The residue was purified by flash column chromatography (petrol:ethyl acetate, 1:2) to afford the title product (49 mg, 93%) as a white amorphous solid; $[\alpha]_D^{25}$-81.2 (c, 0.25 in CHCl$_3$); $\delta_H$ (400 MHz, CDCl$_3$) 1.24 (3H, d, $J_{CH,CH3}$ 6.4 Hz, CH$_3$), 1.46 (9H, s, C(CH$_3$)$_3$), 2.01, 2.06, 2.08, 2.20 (12H, 4×s, 4×OAc), 2.79 (1H, bd, $J_{CH,OH}$ 4.1 Hz, OH), 2.99 (1H, dd, $J_{\alpha H,CH2}$ 8.8 Hz, $J_{CH,H}$ 13.9 Hz, C HHCys), 3.32-3.35 (1H, m, CHHCys), 3.76 (3H, s, OCH$_3$), 4.04 (1H, at, J6.2 Hz, H-5), 4.10-4.16 (1H, m, H-6), 4.19 (1H, dd, $J_{5,6'}$ 6.1 Hz, $J_{6,6'}$ 10.8 Hz, H-6'), 4.36-4.46 (1H, m, C HOH), 4.56 (1H, dd, $J_{\alpha HThr,CH}$ 2.4 Hz, $J_{\alpha H,NH}$ 8.9 Hz, αHThr), 4.57-4.64 (1H, m, αHCys), 4.65 (1H, d, $J_{1,2}$ 9.0 Hz, H-1), 5.13 (1H, dd, $J_{2,3}$ 9.8 Hz, $J_{2,3}$ 9.8 Hz, H-3), 5.31 (1H, d, $J_{\alpha HCys,NH}$ 8.3 Hz, NHCys), 5.47 (1H, d, $J_{3,4}$ 3.2 Hz, H-4), 5.52 (1H, at, J9.6 Hz, H-2), 6.91 (1H, d, $J_{\alpha HThr,NH}$ 9.0 Hz, NHThr).

EXAMPLE 44

Butoxycarbonyl-L-cysteinyl-(S-3,4,6-tri-O-acetyl-2-acetamido-2-deoxy-β-D-glucopyranosyl disulfide)-L-threonine methylester

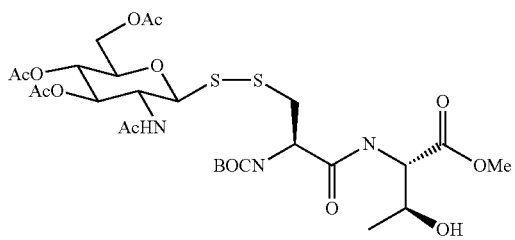

The title product was obtained (55 mg, 88%) as a white amorphous solid by a method analogous to that of Example 43 utilising phenyl 3,4,6-tri-O-acetyl-2-acetamido-2-deoxy-1-selenenylsulfide-D-β-as starting material. $[\alpha]_D^{25}$-47.1 (c, 0.1 in CHCl$_3$); $\delta_H$ (400 MHz, CDCl$_3$) 1.17 (3H, d, $J_{CH,CH3}$ 6.4 Hz, CH$_3$), 1.49 (9H, s, C(CH$_3$)$_3$), 1.91, 2.00, 2.02, 2.07 (12H, 4×s, 4×, COCH$_3$), 2.99 (1H, dd, $J_{CHH,CHH}$ 13.5 Hz, $J_{\alpha H,CH}$ 10.0 Hz, CHH), 3.38 (1H, dd, $J_{\alpha H,CH}$ 4.8 Hz, $J_{CHH,CHH}$ 13.5 Hz, CHH), 3.88-3.91 (1H, m, H-5), 4.16-4.32 (4H, m, H-2, H-6, H-6', CHCH$_3$), 4.45 (1H, d, $J_{\alpha H,CH}$ 2.7 Hz, αHThr), 4.54 (1H, dd, $J_{\alpha H,CHH}$ 9.7 Hz, $J_{\alpha H,CHH}$ 4.7 Hz, αHCys), 4.79 (1H, d, $J_{1,2}$ 10.1 Hz, H-1), 5.06 (1H, at, J9.7 Hz, H-4), 5.28 (1H, at, J 9.7 Hz, H-3).

EXAMPLE 45

N-Butoxycarbonyl-L-cysteinyl-(S-1-β-D-glucopyranosyl disulfide)-L-threonine methylester

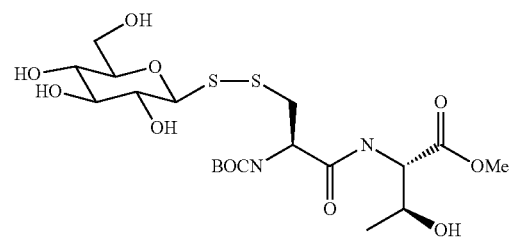

Phenyl 1-selenenylsulfide-β-O-glucopyranoside (70 mg, 0.2 mmol) and triethylamine (0.01 mL, 0.1 mmol) were dissolved in MeOH (8 mL). The resulting solution was stirred at RT. A solution of N-butoxycarbonyl-L-cysteine-L-threonine methylester (22 mg, 0.07 mmol) in MeOH (5 mL) was added slowly to the above solution. After 10 min, t.l.c. (EtOAc:MeOH, 9:1) indicated the formation of a major product ($R_f$ 0.4). The solution was concentrated in vacuo. The residue was purified by flash column chromatography (EtOAc:MeOH, 9:1) to afford the title compound (32 mg, 91%) as a white amorphous solid; $[\alpha]_D^{25}$-139.5 (c, 0.6 in MeOH); $\delta_H$ (500 MHz, CD$_3$OD) 1.19 (3H, d, $J_{CH,CH3}$ 6.2 Hz, CHCH$_3$), 1.49 (9H, s, C(CH$_3$)$_3$), 2.93 (1H, dd, $J_{CHH,CHH}$ 13.5 Hz, $J_{CH,\alpha H}$ 9.5 Hz, CH$_2$Cys), 3.32-3.46 (4H, m, H-3, H-4, H-5, CHH), 3.60-3.63 (1H, m, H-2), 3.73-3.77 (1H, m, H-6), 3.78 (3H, s, OMe), 3.92-3.94 (1H, m, H-6'), 4.31-4.36 (1H, m, CHCH$_3$), 4.39 (1H, d, $J_{1,2}$ 9.3 Hz, H-1), 4.48 (1H, d, $J_{\alpha H,CH}$ 2.9 Hz, αHThr), 4.69 (1H, dd, $J_{\alpha H,CHH}$ 9.0 Hz, $J_{\alpha H,CHH}$ 5.2 Hz, αHCys).

EXAMPLE 46

N-Butoxycarbonyl-L-cysteinyl-(S-2-acetamino-2-deoxy-1-β-D-glucopyranosyl disulfide)-L-threonine methylester

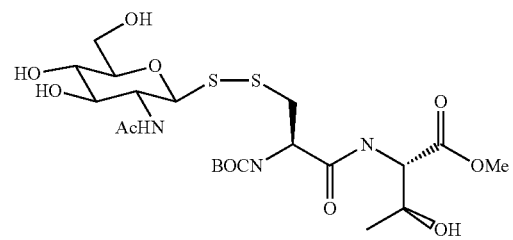

The title compound (32 mg, 91%) was obtained as a white amorphous solid by a method analogous to that of Example 45 utilising phenyl 2-acetamido-2-deoxy-1-selenenylsulfide-β-D-glucopyranoside as starting material. $[\alpha]_D^{25}$+6.21 (c, 0.45 in MeOH); $\delta_H$ (500 MHz, CD$_3$OD) 1.19 (3H, d, $J_{CHCH3}$ 6.7 Hz, CHCH$_3$), 1.49 (9H, s, C(CH$_3$)$_3$), 1.99 (3H, s, COCH$_3$), 2.97 (1H, dd, $J_{CH,H}$ 13.8 Hz, $J_{CH,\alpha H}$ 9.6 Hz, C HHCys), 3.31-3.33 (1H, m, CHH, 3.38-3.41 (1H, m, H-5), 3.45 (1H, at, J9.3 Hz, H-4), 3.54 (1H, dd, J$_{2,3}$ 8.6 Hz, J$_{3,4}$ 9.8 Hz, H-3), 3.76-3.77 (1H, m, H-6), 3.78 (3H, s, OMe), 3.79-4.01 (2H, m, H-2, H-6'), 4.33 (1H, dq, $J_{CHCH3}$ 6.3 Hz, $J_{CH,\alpha H}$ 3.0 Hz, CHCH$_3$), 4.48 (1H, d, $J_{\alpha H,CH}$ 3.0 Hz, αHThr), 4.59 (1H, d, J$_{1,2}$ 10.3 Hz, H-1), 4.63-4.67 (1H, m, αHcys).

EXAMPLE 47

Phenyl-1-selenenylsulfide-β-D-glucopyranoside

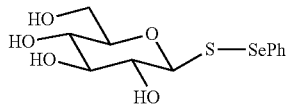

1-Thio-β-D-glucopyranoside (200 mg, 0.9 mmol) and phenylselenenyl bromide (230 mg, 1.0 mmol) were added to anhydrous 1,4-dioxane (5 mL) stirred under an atmosphere of argon. After a 1 min period, t.l.c. (ethyl acetate) indicated the formation of a major product (R$_f$ 0.2). The reaction was quenched with the addition of triethylamine (2 mL). The solution was concentrated in vacuo. The residue was purified by flash column chromatography (ethyl acetate:methanol, 9:1) to afford the title product (165 mg, 57%) as an off white amorphous solid; $[\alpha]_D^{22}$+56.2 (c, 1 in CHCl$_3$); $\delta_H$ (400 MHz, MeOD) 3.31-3.33 (2H, m, H-3, H-5), 3.39-3.45 (2H, m, H-2, H-4), 3.62 (1H, dd, J$_{5,6}$ 5.3 Hz, J$_{6,6'}$ 12.1 Hz, H-6), 3.83 (1H, dd, J$_{5,6'}$ 1.9 Hz, J$_{6,6'}$ 12.2 Hz, H-6), 4.47 (1H, d, J$_{1,2}$ 9.4 Hz, H-1), 7.27-7.34 (3H, m, Ar—H), 7.75-7.78 (2H, m, Ar—H).

EXAMPLE 48

Phenyl 1-selenenylsulfide-β-D-galactopyranoside

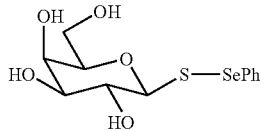

The title compound was obtained (193 mg, 20%) as an off white amorphous solid by a method analogous to that of Example 47 utilising 1-thio-β-D-galactopyranoside as starting material. $[\alpha]_D^{25}$-111.4 (c, 1 in MeOH); $\delta_H$ (400 MHz, CD$_3$OD) 3.52 (1H, dd, J$_{2,3}$ 9.4 Hz, J$_{3,4}$ 3.3 Hz, H-3), 3.56 (1H, at, J$_{4,5}$ 0.9 Hz, J6.5 Hz, H-5), 3.67-3.69 (2H, d, J6.0 Hz, H-6, H-6'), 3.74 (1H, at, J9.3 Hz, H-2), 3.91 (1H, dd, J$_{3,4}$ 3.2 Hz, J$_{4,5}$ 0.7 Hz, H-4), 4.45 (1H, d, J$_{1,2}$ 9.7 Hz, H-1), 7.27-7.30 (3H, m, Ar—H), 7.76-7.79 (2H, m, Ar—H).

EXAMPLE 49

Phenyl 2,3,4,6-tetra-O-acetyl-1-selenenylsulfide-β-D-glucopyranoside

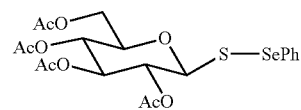

1-Thio-2,3,4,6-tetra-O-acetyl-β-D-glucopyranose (200 mg, 0.6 mmol) and PhSeBr (150 mg, 0.6 mmol) were added to freshly distilled DCM (5 mL) and stirred under argon at RT. After 5 min, t.l.c. (petrol:EtOAc, 1:1) indicated the formation of a major product (R$_f$ 0.5) along with complete consumption of the starting material (R$_f$ 0.4). The reaction was quenched with the addition of triethylamine (2 mL) and stirred for 5 min. The residue was partitioned between DCM (5 mL) and water (10 mL) and the aqueous phase was re-extracted with DCM (3×5 mL). The combined organics were washed with brine (10 mL), dried over MgSO$_4$, filtered and the solvent removed in vacuo. The resulting residue was purified by flash column chromatography (petrol:EtOAc, 2:1) to afford the title product (260 mg, 93%) as a yellow crystalline solid mp 111-112° C.; $[\alpha]_D^{25}$-250.1 (c, 1.0 in CHCl$_3$); $\delta_H$ (400 MHz, CDCl$_3$) 2.02, 2.01, 2.00 (12H, 4×s, 4×CH$_3$), 3.75 (1H, ddd, J$_{4,5}$ 9.9 Hz, J$_{5,6}$ 2.4 Hz, J$_{5,6'}$ 4.6 Hz, H-5), 4.08 (1H, dd, J$_{5,6}$ 2.6 Hz, J$_{6,6'}$ 12.4 Hz, H-6), 4.16 (1H, dd, J$_{5,6'}$ 4.5 Hz, J$_{6,6'}$ 12.4 Hz, H-6'), 4.62 (1H, d, J$_{1,2}$ 9.8 Hz, H-1), 5.12 (1H, at, J9.7 Hz, H-4), 5.20-5.30 (2H, m, H-2, H-3), 7.25-7.28 (3H, m, Ar—H), 7.67-7.70 (2H, m, Ar—H).

EXAMPLE 50

Phenyl 2,3,4,6-tetra-O-acetyl-1-selenenylsulfide-β-D-galactopyranoside

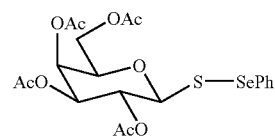

The title compound (402 mg, 95%) was obtained as a yellow crystalline solid using a method analogous to that of Example 49 utilising 1-thio-2,3,4,6-tetra-O-acetyl-β-D-galactopyranose as starting material. Mp 123-125° C.; $[\alpha]_D^{25}$-172.4 (c, 1.0 in CHCl$_3$); $\delta_H$ (400 MHz, CDCl$_3$) 1.99, 2.02, 2.16 (12H, 4×s, 4×CH$_3$), 3.94-4.03 (3H, m, H-5, H-6, H-6'), 4.64 (1H, d, J$_{1,2}$ 10.1 Hz, H-1), 5.04 (1H, dd, J$_{2,3}$ 10.2 Hz, J$_{3,4}$ 3.3 Hz, H-3), 5.40-5.45 (2H, m, H-2, H-4), 7.27-7.30 (3H, m, Ar—H), 7.69-7.71 (2H, m, Ar—H).

EXAMPLE 51

Phenyl 3,4,6-tri-O-acetyl-2-acetamido-2-deoxy-1-selenenylsulfide-β-D-glucopyranoside

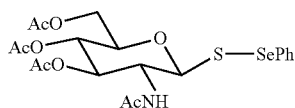

The title compound (300 mg, 66%) was obtained as a white crystalline solid using a method analogous to that of Example 49 utilising 1-thio-3,4,6-tri-O-acetyl-2-acetamido-2-deoxy-β-D-glucopyranose as starting material. Mp 177-179° C.; $[\alpha]_D^{25}$-134.0 (c, 1.0 in CHCl$_3$); $\delta_H$ (400 MHz, CDCl$_3$) 1.90 (3H, s, NHCOCH$_3$), 1.99, 2.00, 2.03 (9H, 3×s, 3×CH$_3$), 3.76 (1H, ddd, J$_{4,5}$ 10.1 Hz, J$_{5,6}$ 2.3 Hz, J$_{5,6'}$ 4.7 Hz, H-5), 4.07 (1 H, dd, J$_{5,6}$ 2.3 Hz, J$_{6,6'}$ 12.3 Hz, H-6), 4.15 (1H, dd, J$_{5,6'}$ 4.6 Hz, J$_{6,6'}$ 12.2 Hz, H-6'), 4.19-4.24 (1H, m, H-2), 4.78 (1H, d, J$_{1,2}$ 10.1 Hz, H-1), 5.09 (1H, at, J9.7 Hz, H-4), 5.28 (1H, at, J9.5 Hz, H-3), 5.79 (1H, d, J9.1 Hz, NHAc), 7.24-7.28 (3H, m, Ar—H), 7.68-7.70 (2H, m, Ar—H).

EXAMPLE 52

Phenyl-2-acetylamino-2-deoxy-1-selenenylsulfide-(3-D-glucopyranoside

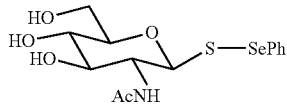

1-Thio-2-acetylamino-2-deoxy-β-D-glucopyranoside (230 mg, 0.98 mmol) and phenylselenenyl bromide (250 mg, 1.08 mmol) were added to anhydrous 1,4-dioxane (5 mL) and anhydrous methanol (3 ml) stirred under an atmosphere of argon. After a 1 min period, t.l.c. (ethyl acetate:methanol, 9:1) indicated the formation of a major product (R$_f$ 0.4). The reaction was quenched with the addition of triethylamine (5 mL). The solution was concentrated in vacuo. The residue was purified by flash column chromatography (ethyl acetate: methanol, 9:1) to afford the title product (270 mg, 70%) as a white amorphous solid; $[\alpha]_D^{22}$-174.0 (c, 1 in MeOH); $\delta_H$ (400 MHz, MeOD), 1.96 (3H, s, CH$_3$), 3.31-3.39 (2H, m, H-4, H-5), 3.51 (1H, at, J8.1 Hz, H-3), 3.65 (1H, dd, J$_{5,6}$ 5.0 Hz, J$_{6,6'}$ 11.7 Hz, H-6), 3.82-3.90 (2H, m, H-2, H-6'), 4.65 (1H, d, J$_{1,2}$ 10.2 Hz, H-1), 7.27-7.34 (3H, m, ArH), 7.72-7.74 (2H, m, ArH).

EXAMPLE 53

Ethyl 1-thio-β-D-glucopyranosyl disulfide

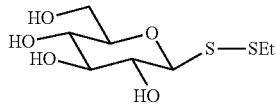

Phenyl 1-selenenylsulfide-β-D-glucopyranoside (140 mg, 0.4 mmol) was dissolved in MeOH (10 mL) and stirred at RT. To this solution ethanethiol (10 μL, 0.1 mmol) and triethylamine (60 μL, 0.4 mmol) in MeOH (5 mL) were added dropwise over 1 h. After 1 h, t.l.c. (EtOAc:MeOH, 9:1) indicated the formation of a major product (R$_f$ 0.4) along with complete consumption of the starting material (R$_f$ 0.5). The solution was concentrated in vacuo. The residue was purified by flash column chromatography EtOAc:MeOH, 5:1) to afford the title product (30 mg, 90%) as a white amorphous solid; $[\alpha]_D^{22}$-65.3 (c, 0.4 in CHCl$_3$); $\delta_H$ (500 MHz, CD$_3$OD) 1.33 (3H, t, J7.4 Hz, CH$_3$), 2.86 (2H, q, J7.4 Hz, CH$_2$), 3.30-3.34 (2H, m, H-4, H-5), 3.41 (1H, at, J9.0 Hz, H-3), 3.49 (1H, at, J Hz, H-2), 3.67 (1H, dd, J$_{5,6}$ 5.3 Hz, J$_{6,6'}$ 12.0 Hz, H-6), 3.88 (1H, dd, J$_{5,6'}$ 2.1 Hz, J$_{6,6'}$ 12.0 Hz, H-6'), 4.35 (1H, d, J$_{1,2}$ 9.1 Hz, H-1).

EXAMPLE 54

Ethyl 2-acetamido-2-deoxy-1-disulfide-β-D-glucopyranoside

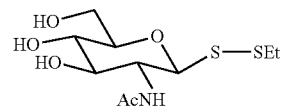

Phenyl 2-acetamido-2-deoxy-1-selenenylsulfide-β-D-glucopyranoside (140 mg, 0.4 mmol) was dissolved in MeOH (10 mL) and stirred at RT. To this solution ethanethiol (10 μL, 0.13 mmol) and triethylamine (55 μL, 0.4 mmol) in MeOH (5 mL) were added dropwise over 1 h. After 1 h, t.l.c. (BtOAc: MeOH, 9:1) indicated the formation of a major product (R$_f$ 0.2). The solution was concentrated in vacuo. The resulting residue was purified by flash column chromatography (EtOAc:MeOH, 9:1) to afford the title product (38 mg, 99%) as a white amorphous solid; $[\alpha]_D^{25}$-7.9 (c, 1.0 in CHCl$_3$); $\delta_H$ (400 M , CD$_3$OD) 1.30 (3H, t, J7.3 Hz, CH$_3$), 2.01 (3H, s, OAc), 2.83-2.86 (2H, m, CH$_2$), 3.31-3.39 (2H, m, H-4, H-5), 3.51-3.56 (1H, m, H-3), 3.68-3.72 (1H, m, H-6), 3.84-3.91 (2H, m, H -2, H-6'), 4.57 (1H, d, J$_{1,2}$ 10.3 Hz, H-1).

EXAMPLE 55

Protein glycosylation procedures using thiosulfonate reagents

A. SBLS156C mutant (24 mg, 0.89 μmol) was dissolved in aqueous buffer solution (2.4 mL, 70 mM HEPES, 2 mM CaCl$_2$, pH 6.9). 2,3,4,6-Tetra-O-acetyl-β-D-glucopyranosyl phenylthiosulfonate (50 mg, 0.1 mmol) was dissolved in water/acetonitrile (1.6 mL, 9/7 v/v). A portion of the sugar solution (50 μL) was added to the protein solution and placed on an end-over-end rotator. After 25 min, the absence of free thiol was shown by Ellman's analysis (Ellman, G. L. Arch. Biochem. Biophys. 1959, 82, 70), at which point another portion of sugar solution (50 μL) was added. The reaction was placed on an end-over-end rotator for a further 5 min, at which point the reaction mixture was loaded onto a PD10 Sephadex® G25 column and eluted with 70 mM HEPES, 2 mM CaCl$_2$, pH 7.0. The protein fraction was collected and dialysed (MWCO 12-14 KDa) against 10 MM MES, 1 mM CaCl$_2$, pH 5.8, (1×4L for 1 h, 2×2L for 30 min), to afford the glycosylated product m/z (ES) found 27072 calcd. 27078.

B. SBLS156C mutant (24 mg, 0.89 µmol) was dissolved in aqueous buffer solution (2.4 mL, 70 mM HEPES, 2 mM CaCl$_2$, pH 6.9). 2,3,4,6-tetra-O-acetyl-β-D-galactopyranosyl phenylthiosulfonate (50 mg, 0.1 mmol) was dissolved in water/acetonitrile (1.0 mL, 1/1 ratio). The sugar solution (50 µL) was added to the protein solution and placed on an end-over-end rotator. After 25 min, the absence of free thiol was shown by Ellman's analysis, at which point another portion of sugar solution (50 µl) was added. The reaction was placed on an end-over-end rotator for a further 5 min, at which point the reaction mixture was loaded onto a PD10 Sephadex® G25 column and eluted with 70 mM HEPES, 2 mM CaCl$_2$pH 7.0. The protein fraction was collected and dialysed (MWCO 12-14 KDa) against 10 mM MES, 1 mM CaCl$_2$, pH 5.8, (1×4 L for 1 h, 2×2 L for 30 min), to afford the glycosylated product m/z (ES) found 27072 calcd. 27078.

C. SBLS156C mutant (10 mg, 0.37 µmol) was dissolved in degassed aqueous buffer solution (1 mL, 70 mM CHES, 5 mM MES, 2 mM CaCl$_2$, pH 9.5). 2,3,6-Tri-O-acetyl-4-O-(2,3,6-tri-O-acetyl-4-O-(2,3,4,6-tetra-O-acetyl-α-O-glucopyranosyl)-α-D-glucopyranosyl)-β-D-glucopyranosyl phenylthiosulfonate (30 mg, 0.03 mmol) was dissolved in acetonitrile (150 µL). The sugar solution (75 µL) was added to the protein solution and placed on an end-over-end rotator. After 30 min, the absence of free thiol was shown by Ellman's analysis, at which point the reaction mixture was loaded onto a PD10 Sephadex® G25 column and eluted with 70 mM HEPES, 2 mM CaCl$_2$ pH 7.0. The protein fraction was collected and dialysed (MWCO 12-14 KDa) against 10 mM MES, 1 mM CaCl$_2$, pH 5.8, (1×4 L for 1 h, 2×2 L for 30 min), to afford the glycosylated product m/z (ES) found 27654 calcd. 27653.

D. BSA (10 mg, 0.14 µmol) was dissolved in aqueous buffer solution (1 mL, 50 mM Tris, pH 7.7). 2,3,4,6 -Tetra-O-acetyl-β-D-glucopyranosyl phenylthiosulfonate (10 mg, 0.02 mmol) was dissolved in water/acetonitrile (1.0 mL, 8/2 ratio). The sugar solution (150 µl) was added to the protein solution and placed on an end-over-end rotator. After 30 min, the absence of free thiol was shown by Ellman's analysis, at which point the reaction mixture was loaded onto a PD10 Sephadex® G25 column and eluted with 70 mM HEPES, 2 mM CaCl$_2$ pH 7.0. The protein fraction was collected and dialysed (MWCO 12-14 KDa) against pure water, (1×4 L for 1 h, 2×2 L for 30 min), to afford the glycosylated product; m/z (S) found 66798 calcd. 66794.

E. BSA (10 mg, 0.14 µmol) was dissolved in aqueous buffer solution (1 mL, 50 mM Tris, pH 7.7). 2,3,4,6-Tetra-O-acetyl-β-D-galactopyranosyl phenylthiosulfonate (25 mg, 0.05 mmol) was dissolved in acetonitrile (0.5 mL). The sugar solution (75 µL) was added to the protein solution and placed on an end-over-end rotator. After 30 min, the absence of free thiol was shown by Ellman's analysis, at which point the reaction mixture was loaded onto a PD10 Sephadex® G25 column and eluted with 70 mM HEPES, 2 mM CaCl$_2$pH 7.0. The protein fraction was collected and dialysed (MWCO 12-14 KDa) against pure water, (1×4 L for 1 h, 2×2 L for 30 min), to afford the glycosylated product m/z (ES) found 66792 calcd. 66794.

EXAMPLE 56

Protein glycosylation procedures using selenenylsulfide reagents

A. SBLS156C mutant (5 mg) was dissolved in degassed aqueous buffer solution (1 mL, 70 mM CHES, 5 mM MES, 2 mM CaCl$_2$, pH 9.5). Phenyl 2,3,4,6-tetra-O-acetyl-β-D-selenenylsulfide glucopyranoside (10 mg, 0.02 mmol) was dissolved in acetonitrile (500 µl). The sugar solution (500 µl) was added to the protein solution and placed on an end-over-end rotator. After 1 h, the absence of free thiol was shown by Ellman's analysis, at which point the reaction mixture was loaded onto a PD10 Sephadex® G25 column and eluted with 70 mM HEPES, 2 mM CaCl$_2$pH 7.0. The protein fraction was collected and dialysed (MWCO 12-14 KDa) against water, (1×4 L for 1 h, 2×2 L for 30 min), to afford the glycosylated product. m/z (ES) found 27074 calcd. 27077.

B. BSA (5 mg) was dissolved in degassed aqueous buffer solution (1 mL, 70 mM CHES, 5 mM MES, 2 mM CaCl$_2$, pH 9.5). Phenyl 2,3,4,6-tetra-O-acetyl-β-D-selenenylsulfide glucopyranoside (10 mg, 0.02 mmol) was dissolved in acetonitrile (800 µl). The sugar solution (800 µl) was added to the protein solution and placed on an end-over-end rotator. After 1 h, the absence of free thiol was shown by Ellman's analysis, at which point the reaction mixture was loaded onto a PD10 Sephadex® G25 column and eluted with 70 mM HEPES, 2 mM CaCl$_2$pH 7.0. The protein fraction was collected and dialysed (MWCO 12-14 KDa) against water, (1×4 L for 1 h, 2×2 L for 30 min), to afford the glycosylated product m/z (ES) found 66792 calcd. 66794.

C. SBLS156C mutant (5 mg) was dissolved in degassed aqueous buffer solution (1 mL, 70 mM CHES, 5 mM MES, 2 mM CaCl$_2$, pH 9.5). Phenyl 2,3,4,6-tetra-O-acetyl-β-D-selenenylsulfide galactopyranoside (10 mg, 0.02 mmol) was dissolved in acetonitrile (500 µl). The sugar solution (500 µl) was added to the protein solution and placed on an end-over-end rotator. After 1 h, the absence of free thiol was shown by Ellman's analysis, at which point the reaction mixture was loaded onto a PD10 Sephadex® G25 column and eluted with 70 mM HEPES, 2 mM CaCl$_2$pH 7.0. The protein fraction was collected and dialysed (MWCO 12-14 KDa) against water, (1×4 L for 1 h, 2×2 L for 30 min), to afford Glc(Ac)$_4$SBLS156C m/z (ES) found 27074 calcd. 27077.

D. SBLS156C mutant (10 mg) was dissolved in degassed aqueous buffer solution (1 mL, 70 mM CHES, 5 mM MES, 2 mM CaCl$_2$, pH 9.5). Phenyl-1-selenenylsulfide-β-D-glucopyranoside (15 mg, 0.02 mmol) was dissolved in water/acetonitrile (0.8 mL, 1/1 ratio). The sugar solution (500 µl) was added to the protein solution and placed on an end-over-end rotator. After 30 min, the absence of free thiol was shown by Ellman's analysis, the reaction was placed on an end-over-end rotator for a further 30 min, at which point the reaction mixture was loaded onto a PD10 Sephadex® G25 column and eluted with 70 mM HEPES, 2 mM CaCl$_2$ pH 7.0. The protein fraction was collected and dialysed (MWCO 12-14 KDa) against water, (1×4 L for 1 h, 2×2 L for 30 min), to afford AcGlcSBLS156C m/z (S) found 27072 calcd. 26911.

E. SBLS156C mutant (5 mg) was dissolved in degassed aqueous buffer solution (2.4 mL, 70 mM HEPES, 2 mM CaCl$_2$, pH 6.9). Phenyl 2-acetylamino-2-deoxy-1-selenenylsulfide-β-D-glucopyranoside (5 mg, 0.01 mmol) was dissolved in acetonitrile (200 µL, 1/1 ratio). The sugar solution (100 µl) was added to the protein solution and placed on an end-over-end rotator. After 30 min, the absence of free thiol was shown by Ellman's analysis, at which point another portion of sugar solution (100 µl) was added. The reaction was placed on an end-over-end rotator for a further 30 min, at which point the reaction mixture was loaded onto a PD10 Sephadex® G25 column and eluted with 70 mM HEPES, 2 mM CaCl$_2$ pH 7.0. The protein fraction was collected and dialysed (MWCO 12-14 KDa) against 10 mM MES, 1 mM CaCl$_2$, pH 5.8, (1×4 L for 1 h, 2×2 L for 30 min), to afford HOGlcNAcSBLS156C m/z (ES) found 26950 calcd. 26950.

F. SBLS156C mutant (5 mg) was dissolved in degassed aqueous buffer solution (1 mL, 70 mM CHES, 5 mM MES, 2 mM $CaCl_2$, pH 9.5). Phenyl 3,4,6-tri-O-acetyl-2-acetylamino-2-deoxy-1-selenenylsulfide-β-D-glucopyranoside (10 mg, 0.02 mmol) was dissolved in acetonitrile (500 μl). The sugar solution (500 μl) was added to the protein solution and placed on an end-over-end rotator. After 1 h, the absence of free thiol was shown by Ellman's analysis, at which point the reaction mixture was loaded onto a PD10 Sephadex® G25 column and eluted with 70 mM HEPES, 2 mM $CaCl_2$ pH 7.0. The protein fraction was collected and dialysed (MWCO 12-14 KDa) against water, (1×4 L for 1 h, 2×2 L for 30 min), to afford AcGlcNAcSBLS156C m/z (ES) found 27074 calcd. 27078.

G. SBLCys156 (5 mg) was dissolved in degassed aqueous buffer solution (500 μL, 70 mM CHES, 5 mM MES, 2 mM $CaCl_2$, pH 9.5). Phenyl 2,3,6-tri-O-acetyl-1-selenenylsulfide-4-O-(2,3,6-tri-O-acetyl-4-O-(2,3,4,6-tetra-O-acetyl-α-O-glucopyranosyl)-α-D-glucopyranosyl)-β-D-glucopyranoside (15 mg, 0.015 mmol) was dissolved in acetonitrile (300 μL, 75 eq) and this solution was added to the protein solution and placed on an end-over-end rotator. After 30 min, the absence of free thiol was shown by Ellman's analysis. The reaction was placed on an end-over-end rotator for a further 30 min, at which point the reaction mixture was loaded onto a PD10 Sephadex® G25 column and eluted with 70 mM HEPES, 2 mM $CaCl_2$, pH 7.0. The protein fraction was collected and dialysed (MWCO 12-14 KDa) against water (1×4 L for 1 h, 2×2 L for 30 min) to afford $Glc(Ac)_4Glc(Ac)_3Glc(Ac)_3$-SBLCys156 m/z ($ES^+$) found 27644 calcd. 27653.

H. SBLCys156 (5 mg) was dissolved in degassed aqueous buffer solution (500 μL, 70 mM CHES, 5 mM MES, 2 mM $CaCl_2$, pH 9.5). Phenyl 1-selenenylsulfide-β-D-galactopyranoside (15 mg, 0.04 mmol) was dissolved in water/acetonitrile (600 μL, 1/3 ratio). The sugar solution (600 μL, 230 eq) was added to the protein solution and placed on an end-over-end rotator. After 30 min, the absence of free thiol was shown by Ellman's analysis,[8] the reaction was placed on an end-over-end rotator for a further 30 min, at which point the reaction mixture was loaded onto a PD10 Sephadex® G25 column and eluted with 70 mM HEPES, 2 mM $CaCl_2$, pH 7.0. The protein fraction was collected and dialysed (MWCO 12-14 KDa) against water (1×4 L for 1 h, 2×2 L for 30 min) to afford Gal-SBLCys156 m/z ($ES^+$) found 26908 calcd. 26909.

I. 1-Thio-β-D-maltotriose (104 mg, 0.2 mmol) was dissolved in MeOH (5 mL) to which a solution of PhSeBr (70 mg, 0.3 mmol) in EtOAc (2 mL) was added. After 2 min triethylamine (2 mL) was added and the reaction was diluted with water (10 mL) and petrol (5 mL). The phases were separated and the aqueous phase was washed with petrol (3×10 mL) and lyophilised. The crude phenyl 1-selenenylsulfide-maltotriose (m/z 755, 757 ($M+Br^-$, 100%)) was taken up into water (10 mL) of which 50 μL (25 eq) was added to a solution of SBLCys156 (1 mg) in 500 μL of buffer (70 mM CHES, 5 mM MES, 2 mM $CaCl_2$, pH 9.5). The resulting solution was placed on an end-over-end rotator. After 2.5 h the reaction mixture was loaded onto a PD10 Sephadex® G25 column and eluted with 70 mM HEPES, 2 mM $CaCl_2$, pH 7.0. The protein fraction was collected to afford GlcGlcGlc-SBLCys156 m/z ($ES^+$) found 27226 calcd. 27233.

J. BSA (5 mg) was dissolved in degassed aqueous buffer solution (1 mL, 70 mM CHES, 5 mM MES, 2 mM $CaCl_2$, pH 9.5). Phenyl 1-selenenylsulfide-β-D-glucopyranoside (6 mg, 0.02 mmol) was dissolved in water/acetonitrile (0.7 mL, 2/5 ratio). The sugar solution (700 μL, 225 eq) was added to the protein solution and placed on an end-over-end rotator. After 1 h, the absence of free thiol was shown by Ellman's analysis,[8] at which point the reaction mixture was loaded onto a PD10 Sephadex® G25 column and eluted with 70 mM HEPES, 2 mM $CaCl_2$, pH 7.0. The protein fraction was collected and dialysed (MWCO 12-14 KDa) against water (1×4 L for 1 h, 2×2 L for 30 min) to afford Glc-BSA m/z ($ES^+$) found 66620 calcd. 66625.

Summary of glycosylation reactions utilising selenenyl sulphide reagents

| Reagent | EtSH | BocCysThrOMe | SBLS156C | BSA |
|---|---|---|---|---|
| $Glc(Ac)_4$SSePh | 82% | 75% | >95% | >95% |
| $Gal(Ac)_4$SSePh | 82% | 93% | >95% | |
| $Glc(Ac)_3$NAcSSePh | 93% | 88% | >95% | |
| GlcSSePh | 90% | 91% | >95% | >95% |
| GalSSePh | | | >95% | |
| GlcNAcSSePh | 77% | 77% | >95% | |
| $Glc(Ac)_4Glc(Ac)_3Glc(Ac)_3$SSePh | | | 90% | >95% |
| GlcGlcGlcSSePh | | | >95% | |

EXAMPLE 57

Comparison of Compounds of Formula I with glyco-MTS Reagents

In Tables 1 and 2, MTS denotes $CH_3$—$SO_2$—S—, and PTS denotes Ph—$SO_2$—S—.

TABLE 1

Preparation

| Glycosylating Reagent | Preparation[1] | |
|---|---|---|
| | Total Yield (%) | Steps |
| $Glc(Ac)_4$β-MTS | 46[2] | 3 |
| $Glc(Ac)_4$β-PTS | 64 | 3 |
| $Glc(Bn)_4$β-MTS | 43[3] | 5 |
| $Glc(Bn)_4$β-PTS | 67 | 5 |
| $Gal(Ac)_4$β-MTS | 47 | 3 |
| $Gal(Ac)_4$β-PTS | 65 | 3 |
| $Glc(Ac)_4α(1,4)Glc(Ac)_3α(1,4)Glc(Ac)_3$β-PTS | 60 | 3 |

[1]from the corresponding parent carbohydrate D-glucose (Glc), D-galactose (Gal) or Glcα(1,4)Glcα(1,4)Glc.
[2]Taken from B. G. Davis, R. C. Lloyd and J. B. Jones, *J. Org. Chem.*, 1998, 63, 9614, and B. G. Davis, M. A. T. Maughan, M. P. Green, A. Ullman and J. B. Jones, *Tetrahedron Asymmetry*, 2000, 11, 245.
[3]Taken from B. G. Davis, S. J. Ward adn P. M. Randle, Chem. Commun., 2001, 189.

As shown in Table 1, the glyco-PTS reagents according to the invention were synthesised in superior yields to the corresponding glyco-MTS reagents. Moreover, the costs of the starting materials for synthesis of the glyco-PTS reagents was approximately ten fold lower than for the corresponding glyco-MTS reagents (at 2003 costs).

In Table 2, SBL-Cys156 is subtilisin *Bacillus lentus* mutant S156C, and BSA-Cys58 is bovine serum albumin.

TABLE 2

Comparison of glycosylation reactions of glyco-MTS and glyco-PTS reagents.

| Glycosylating reagent | EtSH[1] Yield (%) | EtSH[1] Time (h) | Peptide[2] Yield (%) | Peptide[2] Time (h) | Protein[3] SBL-Cys 156 Yield (%) | Protein[3] SBL-Cys 156 Time (min) | Protein[3] BSA-Cys58 Yield (%) | Protein[3] BSA-Cys58 Time (min) |
|---|---|---|---|---|---|---|---|---|
| Glc(Ac)$_4$β-MTS | 96[5] | 3 | 62[5] | 5 | 100[4] | 50[4] | — | — |
| Glc(Ac)$_4$β-PTS | 82 | 1 | 99 | 5 | 100 | 30 | 100 | 30 |
| Glc(Bn)$_4$β-MTS | 78[5] | 15 | 65 | 4 | — | — | — | — |
| Glc(Bn)$_4$β-PTS | 95 | 1.5 | 82 | 5 | — | — | — | — |
| Gal(Ac)$_4$β-MTS | 83 | 1 | — | — | — | — | — | — |
| Gal(Ac)$_4$β-PTS | 91 | 1 | 95 | 2 | 100 | 30 | 100 | 30 |
| Glc(Ac)$_4$α(1,4) Glc(Ac)$_3$α(1,4) Glc(Ac)$_3$β-PTS | 93 | 1 | 74 | 3 | 100 | 30 | — | — |

[1] Et$_3$N, DCM, RT, 1 equivalent (eq.) of thiosulfonate.
[2] Et$_3$N, DCM/MeOH (20:1), RT, 1 eq. of thiosulfonate; Peptide [P]-Cys-Ser-OMe, [P] = Ac except for reaction with Glc(Ac)$_4$α(1,4)Glc(Ac)$_3$α(1,4)Glc(Ac)$_3$β-PTS where [P] = Boc.
[3] 70 mM CHES, 5 mM MES, 2 mM CaCl$_2$ pH 9.5 or 50 mM Tris•HCl, pH 7.7, RT, ~30 eq. for glyco-MTS, ~10 eq. for Glc(Ac)$_4$β-PTS and Gal(Ac)$_4$β-PTS with SBL-Cys156, ~20 eq. for Glc(Ac)$_4$β-PTS and Gal(Ac)$_4$β-PTS with BSA-Cys58, ~40 eq. for Glc(Ac)$_4$α(1,4)Glc (Ac)$_3$α(1,4)Glc(Ac)$_3$β-PTS with SBL-Cys156.
[4] Taken from B. G. Davis, R. C. Lloyd and J. B. Jones, *J. Org. Chem.*, 1998, 63, 9614, and B. G. Davis, M. A. T. Maughan, M. P. Green, A. Ullman and J. B. Jones, *Tetrahedron Asymmetry*, 2000, 11, 245.
[5] Taken from B. G. Davis, S. J. Ward and P. M. Randle, *Chem. Commun.*, 2001, 189.

As can be seen from Table 2, the glyco-PTS reagents of the invention generally provided a higher yield in the glycosylation reaction than did the corresponding glyco-MTS compound.

EXAMPLE 58

Glycosylation of SBLCys156 with GlcGlcGlc-S-SePh at varying pH

| pH | Unreacted protein SBLCys156 | Time (h) | SBLCys-S—S—SePh | GlcGlcGlc-SBLCys156 |
|---|---|---|---|---|
| 7.5 [a] | 10% | 1 | 80% | 10% |
| 8.5 [b] | 10% | 1 | 80% | 10% |
| 9.5 [c] | <5% | 1 | 25% | 75% |
| 9.5 [c] | <5% | 3 | <5% | >95% |

Reaction conditions: SBLCys156 was incubated for 1 h with GlcGlcGlc-S—SePh (20 eq.) in [a] 10 mM Tris pH 7.5; [b] 70 mM CHES, 5 mM MES, 2 mM CaCl$_2$, pH 8.5; [c] 70 mM CHES, 5 mM MES, 2 mM CaCl$_2$, pH 9.5.

EXAMPLE 59

Representative Protein Farnesylation

SBLCys156 (10 mg) was dissolved in aqueous buffer solution (1 mL, 70 mM CHES, 5 mM MES, 2 mM CaCl$_2$, pH 9.5). PMSF (140 µL of a 100 mg/mL solution in acetonitrile) was added. After 10 minutes the reaction mixture was concentrated on a Vivaspin centrifugal filter (10 kDa MWCO, Sartorius); this step was repeated 3 times with addition of 300 µL of Milli Q water. A portion of the resulting deactivated SBLCys156 (1 mg) was then dissolved in 200 µL of buffer (1 mL, 70 mM CHES, 5 mM MES, 2 mM CaCl$_2$, pH 9.5). Farnesyl phenylthiosulfonates (56 µL of a 5 mg/mL solution in THF, 20 equivalents) were added. The mixture was placed in an end-over-end rotator. After 1 h the reaction was desalted using Vivaspin centrifugal filters (4 filtrations with addition of Milli Q water) and analysed by mass spectrometry.

This Example shows that the methods of the invention can also be used to attach farnesyl groups to proteins. Farnesylation is a natural post translational modification associated with many proteins.

EXAMPLE 60

D-Mannose pentaacetate

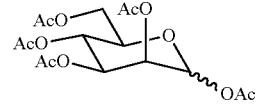 [SMILES: CC(=O)OCC1OC(OC(C)=O)C(OC(C)=O)C(OC(C)=O)C1OC(C)=O]

Mannose (50 g, 280 mmol) was suspended in a stirred solution of acetic anhydride (200 mL) and pyridine (200 mL). After 24 h t.l.c. (petrol:ethyl acetate, 1:1) indicated the formation of a product (R$_f$ 0.3) with complete consumption of the starting material (R$_f$ 0.0). The reaction was diluted with water (400 mL) and partitioned with ethyl acetate (300 mL). The phases were separated, and the aqueous layer was re-extracted with ethyl acetate (2×200 mL). The combined organic layers were washed with dilute hydrochloric acid (2 L, 1M), sodium hydrogen carbonate (500 mL of a saturated aqueous solution), brine (300 mL), dried over (MgSO$_4$), filtered and concentrated in vacuo to afford the title compound (107.3 g, 98%) as an oil being a mixture of anomers (α/β2:1); $δ_H$ (400 MHz, CDCl$_3$) 1.95, 1.99, 2.05, 2.16 (15 H, 4×s, COCH$_3$β) 1.96, 2.00, 2.04, 2.12, 2.13 (15H, 5×s, COCH$_3$α), 3.78 (1H, ddd, $J_{4,5}$ 9.9 Hz, $J_{5,6}$ 2.3 Hz, $J_{5,6'}$ 5.4 Hz, H-5β), 3.99-4.03 (m, H-5α), 4.05-4.10 (2H, m, H-6α, H-6'b), 4.23 (1H, dd, $J_{5,6'}$ 5.0 Hz, $J_{6,6'}$ 12.1 Hz, H-6α), 4.26 (1H, dd, $J_{5,6'}$ 5.3 Hz, $J_{6,6'}$ 12.4 Hz, H-6'b), 5.10 (1H, dd, $J_{2,3}$ 3.3 Hz, $J_{3,4}$ 10.3 Hz, H-3β), 5.20-5.21 (1H, dd, $J_{1,2}$ 2.1 Hz, $J_{2,3}$ 2.5 Hz, H-2α), 5.24-5.30 (3H, m, H-3α, H-4α, H-4β), 5.43 (1H, dd, $J_{1,2}$ 1.2 Hz, $J_{2,3}$ 3.2 Hz, H-2β), 5.83 (1H, d, $J_{1,2}$ 0.9 Hz, H-1β), 6.03 (1H, d, $J_{1,2}$ 2.1 Hz, H-1α).

EXAMPLE 61

2,3,4,6-Tetra-O-acetyl-α-D-mannopyranosoyl bromide

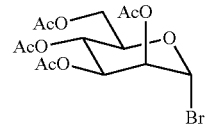 [SMILES: CC(=O)OCC1OC(Br)C(OC(C)=O)C(OC(C)=O)C1OC(C)=O]

D-Mannose pentaacetate (103 g, 264 mmol) was dissolved in anhydrous DCM (200 mL). To this hydrogen bromide (33% in acetic acid, 200 mL) was added. The mixture was left under argon at RT. After a 2 h period, t.l.c. (petrol:ethyl acetate, 2:1) indicated the formation of a product (R$_f$ 0.3) with complete consumption of the starting material (R$_f$ 0.2). The reaction mixture was partitioned between DCM (100 mL) and ice water (200 mL), and the aqueous layer re-extracted with DCM (3×200 mL). The combined organic layers were washed with sodium hydrogen carbonate until pH 8 was obtained, then with brine (300 mL), dried over (MgSO$_4$), filtered and concentrated in vacuo. The resulting title compound, a clear oil, (106.6 g) was used without purification; $\delta_H$ (400 MHz, CDCl$_3$) 1.96, 2.03, 2.06, 2.13 (12H, 4×s, 4×OAc), 4.09 (1H, dd, J$_{5,6}$ 2.2 Hz, J$_{6,6'}$ 12.5 Hz, H-6), 4.18 (1H dd, J$_{4,5}$ 10.1 Hz, J$_{5,6}$ 2.2 Hz, J$_{5,6'}$ 4.8 Hz, H-5), 4.28 (1H, dd, J$_{5,6}$ 4.9 Hz, J$_{6,6'}$ 12.5 Hz, H-6'), 5.32 (1H at, J10.1 Hz, H-4), 5.39 (1H, dd, J$_{1,2}$ 1.6 Hz, J$_{2,3}$ 3.5 Hz, H-2), 5.66 (1H, dd, J$_{2,3}$ 3.5 Hz, J$_{3,4}$ 10.1 Hz, H-3), 6.26 (1H, bs, H-1).

EXAMPLE 62

(2,3,4,6-Tetra-O-acetyl-β-D-mannopyranosyl)-1-isothiouronium bromide

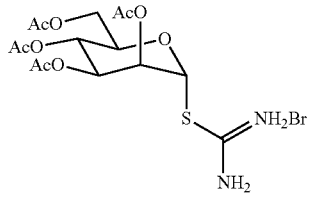

The title compound (80.6 g, 60%, 2 steps) was obtained as a white crystalline solid using a method analogous to that of Example 3 utilising 2,3,4,6-tetra-O-benzyl-D-α-mannopyranosoyl bromide as starting material. Mp 123-126° C. [Lit. 125-128° C. (H$_2$O)]; $[\alpha]_D^{26}$+119.0 (c, 1.0 in MeOH) [Lit. $[\alpha]_D^{27}$+103 (c, 1.0 in Acetone)]; $\delta_H$ (400 MHz, DMSO-d$_6$) 1.95, 2.02, 2.03, 2.14 (12H, 4×s, 4×OAc), 4.08 (1H, dd, J$_{5,6}$ 2.4 Hz, J$_{6,6'}$ 12.3 Hz, H-6), 4.22 (1H, dd, J$_{5,6'}$ 2.4 Hz, J$_{6,6'}$ 12.5 Hz, H-6'), 4.32 (1H, ddd, J$_{4,5}$ 10.0 Hz, J$_{5,6}$ 2.2 Hz, J$_{5,6'}$ 5.2 Hz, H-5), 5.05 (1H, dd, J$_{2,3}$ 3.4 Hz, J$_{3,4}$ 10.0 Hz, H-3), 5.17 (1H, at, J10.0 Hz, H-4), 5.36 (1H, dd, J$_{1,2}$ 1.5 Hz, J$_{2,3}$ 3.4 Hz, H-2), 6.36 (1H, d, J$_{1,2}$ 1.2 Hz, H-1), 9.40 (4H, bs, 2×NH$_2$).

EXAMPLE 63

2,3,4,6-Tetra-O-acetyl-α-D-mannopyranosylthiol

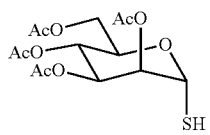

The title compound (14.5 g, 98%) was obtained as a colourless oil by a method analogous to that of Example 2 utilising (2,3,4,6-tetra-O-acetyl-α-D-mannopyranosyl)-1-isothiouronium bromide as starting material. $[\alpha]_D^{24}$+68.7 (c, 1.5 in CHCl$_3$) [Lit. $[\alpha]_D^{20}$+78.6 (c, 0.8 in CHCl$_3$)]; $\delta_H$ (400 MHz, CDCl$_3$) 1.98, 2.04, 2.08, 2.14 (12H, 4×s, 4×OAc), 2.28 (1H, d, J$_{1,SH}$ 6.7 Hz, SH), 4.10 (1H, dd, J$_{5,6}$ 2.4 Hz, J$_{6,6'}$ 12.5 Hz, H-6), 4.28 (1H, dd, J$_{5,6'}$ 5.1 Hz, J$_{6,6'}$ 12.0 Hz, H-6'), 4.32-4.36 (1H, m, H-5), 5.26-5.34 (3H, m, H-2, H-3, H-4), 5.54 (1H, d, J$_{1,SH}$ 6.9 Hz, H-1).

EXAMPLE 65

Phenyl 2,3,4,6-tetra-O-acetyl-1-selenenylsulfide-α-D-mannopyranoside

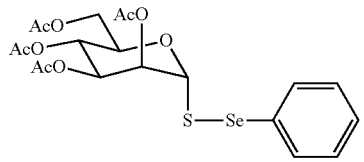 [SMILES: CC(=O)OCC1OC(S[Se]c2ccccc2)C(OC(C)=O)C(OC(C)=O)C1OC(C)=O]

The title compound (590 mg, 83%) was obtained as a yellow oil using a method analogous to that of Example 49 utilising 2,3,4,6-tetra-O-acetyl-α-D-mannopyranosyl thiol as the starting material. $[\alpha]_D^{25}$+13.4 (c, 1.0 in CHCl$_3$; $\delta_H$ (400 MHz, CDCl$_3$) 1.94, 1.94, 2.02, 2.10 (12H, 4×s, 4×OAc), 3.52 (1H, dd, J$_{5,6}$ 2.4 Hz, J$_{6,6'}$ 12.4 Hz, H-6), 3.94 (1H, ddd, J$_{4,5}$ 9.6 Hz, J$_{5,6}$ 2.5 Hz, J$_{5,6'}$ 3.9 Hz, H-5), 4.07 (1H, dd, J$_{5,6'}$ 3.9 Hz, J$_{6,6'\,12.4}$ Hz, H-6'), 5.23 (1H, dd, J$_{2,3}$ 3.2 Hz, J$_{3,4}$ 9.9 Hz, H-3), 5.28(1H, at, J9.7 Hz, H-4), 5.38(1H, d, J$_{1,2}$ 1.6 Hz, H-1), 5.40(1H, dd, J$_{1,2}$ 1.5 Hz, J$_{2,3}$ 3.1 Hz, H-2), 7.26-7.28 (3H, m ArH), 7.62-7.65 (2H, m, ArH).

EXAMPLE 66

2,3,4,6-Tetra-O-acetyl-α-D-mannopyranoside

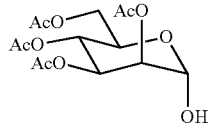 [SMILES: CC(=O)OCC1OC(O)C(OC(C)=O)C(OC(C)=O)C1OC(C)=O]

D-Mannose pentaacetate (26.4 g, 67.7 mmol) was dissolved in freshly distilled THF (150 mL) and benzylamine (11.1 mL, 101.5 mmol) was added to the stirred solution. After a 24 h period, t.l.c. (petrol:ethyl acetate, 1:1) indicated the formation of a product (R$_f$ 0.3) with complete consumption of the starting material (R$_f$ 0.5). The reaction was quenched with the addition of diluted hydrochloric acid (100 mL, 1M) and stirred for 10 min. The reaction was partitioned with DCM (100 mL) and the phases were separated. The aqueous phase was re-extracted with DCM (3×100 mL). The combined organics were washed with dilute hydrochloric acid (100 mL, 1M), brine (100 mL) and dried (MgSO$_4$) and concentrated in vacuo. The resulting orange oil was purified by flash column chromatography (petrol:ethyl acetate, 1:1). The off white crystals were combined and recrystallised from petrol/ethyl acetate to afford the title compound (12.4 g, 53%) as a white crystalline solid mp 92-94° C. [Lit. 92° C.]; $[\alpha]_D^{25}$+17.8 (c, 1.0 in CHCl$_3$); [Lit. $[\alpha]_D^{25}$+21.0 (c, 1.0 in CHCl$_3$)]; $\delta_H$ (400 MHz, CDCl$_3$) 1.98, 2.04, 2.08, 2.14 (12H, 4×s, 4×OAc), 4.09-4.14 (1H, m, H-6), 4.20-4.26 (2H, m, H-5, H-6'), 4.59-5.00 (1H, m, OH), 5.20-5.23 (2H, m, H-1, H-2), 5.27 (1H, at, J9.9 Hz, H-4), 5.39 (1H, dd, J$_{2,3}$ 2.7 Hz, J$_{3,4}$ 9.6 Hz, H-3).

EXAMPLE 67

1',1',1'-Trichloro acetimidate 2,3,4,6-tetra-O-acetyl-α-D-mannopyranoside

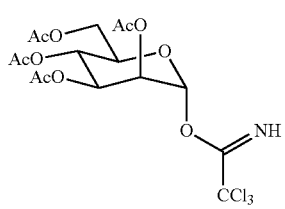

2,3,4,6-Tetra-O-acetyl-α-D-mannopyranoside (1.01 g, 2.87 mmol), 1,1,1-trichloroacetonitrile (2.9 mL, 28.7 mmol) and activated 4 Å molecular sieves (ca. 500 mg) were suspended in anhydrous DCM (20 mL) and left stirring at 0° C. for a period of 1 h. At which point DBU (0.085 mL, 0.57 mmol) was added. After a 1.5 h period, t.l.c. (petrol:ethyl acetate, 1:1) indicated the formation of a product ($R_f$ 0.5) with complete consumption of the starting material ($R_f$ 0.2). The reaction was filtered through Celite® and concentrated in vacuo. The resulting residue was purified by flash column chromatography (petrol:ethyl acetate, 1:1) to afford the title compound (1.42 g, 99%) as a clear oil; $[\alpha]_D^{25}$+42.7 (c, 1.0 in $CHCl_3$) [Lit. $[\alpha]_D^{21}$+50.0 (c, 1.0 in $CHCl_3$)]; $\delta_H$ (400 MHz, $CDCl_3$) 2.20, 2.07, 2.09, 2.29 (12H, 4×s, 4×OAc), 4.15-4.22 (2H, m, H-5, H-6), 4.28 (1H, dd, $J_{5,6'}$ 4.3 Hz, $J_{6,6'}$ 11.8 Hz, H-6'), 5.40-5.42 (2H, m, H-3, H-4), 5.48 (1H, at, J2.1 Hz, H-2), 6.29 (1H, d, $J_{1,2}$ 1.9 Hz, H-1), 8.80 (1H, s, NH)

EXAMPLE 68

Benzyl-α-D-mannopyranoside

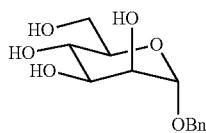 [SMILES: OCC1OC(OCc2ccccc2)C(O)C(O)C1O]

D-Mannose (30 g, 167 mmol) and acetyl chloride (13 mL, 167 mmol) was dissolved in benzyl alcohol (250 mL) and heated to 50° C. for 1 h. The resulting solution was concentrated by low pressure distillation. The resulting residue was purified by flash column chromatography (ethyl acetate/methanol, 9:1) and recrystallised from isopropanol/petrol to afford the title compound (29.34 g, 70%) as a white crystalline solid m.p. 126-127° C. [Lit 128-129° C.]; $[\alpha]_D^{26}$+102.0 (c, 1.1 in MeOH); [Lit. $[\alpha]_D^{18}$+73.1 (c, 1.4 in $H_2O$)]; $\delta_H$ (400 MHz, $CD_3OD$) 3.62 (1H, ddd, $J_{4,5}$ 9.5 Hz, $J_{5,6}$ 2.3 Hz, $J_{5,6'}$ 5.5 Hz, H-5), 3.68 (1H, at, J9.3 Hz, H-4), 3.73-3.78 (2H, m, H-3, H-6), 3.85-3.88 (2H, m, H-2, H-6'), 4.75, 4.52 (2H, ABq, J11.6 Hz, $CH_2$), 4.86 (1H, d, $J_{1,2}$ 1.8 Hz, H-1), 7.28-7.38 (5H, m, ArH).

EXAMPLE 69

Benzyl 4,6-di-O-pivolyl-α-mannopyranoside

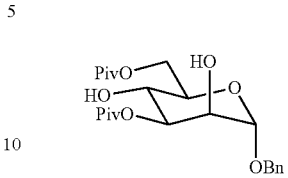

Benyzl-α-D-mannopryanoside (30.0 g, 111.0 mmol) was suspended in anhydrous pyridine (200 mL) under an atmopshere of inert argon. The resulting suspension was cooled to 0° C. and chlorotriphenyl methane (35 mL, 280 mmol) was added to dropwise. After the addition of the chlorotriphenyl methane, t.l.c. (ethyl acetate) indicated the formation of a major product ($R_f$ 0.7) with complete consumption of the starting material ($R_f$ 0.0). The reaction was partitioned between water (50 mL) and ethyl acetate (100 mL). The phases were separated and the aqueous phase was re-extracted with ethyl acetate (3×50 mL). The combined organics were washed with dilute hydrochloric acid (1 L, 1M), sodium hydrogen carbonate (800 mL of a saturated aqueous solution) until pH 7 was obtained, brine (200 mL), dried ($MgSO_4$) and concentrated in vacuo. The resulting residue was recrystallised from ethyl acetate/petrol to afford the title compound (27.07 g, 56%) as a white crystalline solid mp 133-135° C.; $[\alpha]_D^{25}$+64.7 (c, 1.0 in $CHCl_3$); $\delta_H$ (400, $CDCl_3$) 1.251, 1.254 (18H, 2×s, 2×C($CH_3$)$_3$), 3.85 (1H, at, J9.8 Hz, H-4), 3.92 (1H, ddd, $J_{4,5}$ 9.7 Hz, $J_{5,6}$ 5.6 Hz, $J_{5,6'}$ 2.5 Hz, H-5), 4.05 (1H, dd, $J_{1,2}$ 1.9 Hz, $J_{2,3}$ 2.1 Hz, H-2), 4.37 (1H, dd, $J_{5,6}$ 5.6 Hz, $J_{6,6'}$ 11.8 Hz, H-6), 4.42 (1H, dd, $J_{5,6'}$ 2.7 Hz, $J_{6,6'}$ 12.0 Hz, H-6'), 4.53, 4.76 (2H, Abq, J11.9 Hz, $CH_2$), 4.90 (1H, d, $J_{1,2}$ 1.8 Hz, H-1), 5.14 (H, dd, $J_{2,3}$ 3.2 Hz, $J_{3,4}$ 9.7 Hz, H-3), 7.33-7.36 (5H, m, ArH).

EXAMPLE 70

Benzyl 2,4-di-O-benzyl-3,6-di-O-pivolyl-α-D-mannopyranoside

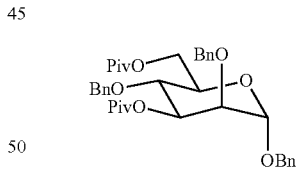

Benzyl 4,6-di-O-pivolyl-α-D-mannopyranoside (15.0 g, 34.2 mmol) and benzene trichloroacetimidate (17 mL, 91.4 mmol) were dissolved in anhydrous DCM (100 mL) and anhydrous cyclohexane (100 mL) and left stirring for 1 h over 4 Å molecular sieves (ca 5 g) under an inert atmosphere of argon. After 1 h trimethyl silyltriflate (0.31 mL, 1.71 mmol) was added. After a 18 h period, t.l.c. (petrol:ethyl acetate, 5:1) indicated the formation of a major product ($R_f$ 0.4) with complete consumption of the starting material ($R_f$ 0.0). The reaction was quenched with triethylamine (ca 30 mL) and the solution was filtered through Celite and concentrated in vacuo. The resulting residue was purified by flash column chromatography (petrol:ethyl acetate, 5:1) to afford the title compound (14.4 g, 70%) as a colourless oil; $[\alpha]_D^{25}$+29.0 (c, 2.0 in $CHCl_3$); $\delta_H$ (400 MHz, $CDCl_3$) 1.24, 1.25 (18H, 2×s, 2×C(CH$_3$)$_3$), 3.97-4.04 (3H, m, H-2, H-4, H-5), 4.25 (1H, dd, J$_{5,6}$ 4.8 Hz, J$_{5,6'}$ 11.6 Hz, H-6), 4.44 (1H, dd, J$_{5,6'}$ 1.6 Hz, J$_{6,6'}$ 11.7 Hz, H-6'), 4.51, 4.74 (2H, ABq, J12.0 Hz, BnCH$_2$), 4.55, 4.61 (2H, ABq, J11.7 Hz, BnCH$_2$), 4.57, 4.80 (2H, ABq, J10.7 Hz, BnCH$_2$), 4.92 (1H, d, J$_{1,2}$ 1.8 Hz, H-1), 5.37 (1H, dd, J$_{2,3}$ 3.1 Hz, J$_{3,4}$ 8.8 Hz, H-3), 7.28-7.35 (15H, m, ArH).

EXAMPLE 71

Benzyl 2,4-di-O-benzyl-α-D-mannopyranoside

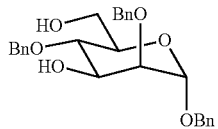 [SMILES: OCC1OC(OCc2ccccc2)C(OCc2ccccc2)C(O)C1OCc1ccccc1]

Benzyl 2,4-di-O-benzyl-3,6-di-O-pivolyl-α-D-mannopyranoside (8.0 g, 12.9 mmol) and sodium methoxide (1.75 g, 32.4 mmol) were dissolved in methanol (100 mL) and heated to reflux. After a 20 h period, t.l.c. (petrol/ethyl acetate, 2:1) indicated the formation of a major product (R$_f$ 0.2) with complete consumption of the starting material (R$_f$ 0.8). The reaction was neutralised with the addition of Dowex®-50 ion exchange resin after which point the reaction was filtered and concentrated in vacuo. The resulting residue was purified by flash column chromatography (petrol/ethyl acetate, 2:1) to afford the title compound (4.50 g, 78%) as a clear oil; $[\alpha]_D^{25}$+ 45.2 (c, 1.0 in CHCl$_3$); $\delta_H$ (500 MHz, CDCl$_3$) 2.83 (2H, bs, 2×OH), 3.83-3.86 (1H, m, H-5), 3.90-4.00 (4H, m, H-2), H-1-4), H-6, H-6'), 4.21-4.28 (1H, m, H-3), 4.58 (1H, d, J12.1 Hz, CHH), 4.72-4.83 (4H, m, 4×CH$_2$Ar), 5.04 (1H, d, J11.1 Hz, CHH), 5.09 (1H, bs, H-1), 7.43-7.51 (15H, m, 15×ArH).

EXAMPLE 71

Benzyl 2,4-di-O-benzyl-3,6-bis-O-(2,3,4,6-tetra-O-acetyl-α-D-mannopyranoside)-α-D-mannopyranoside

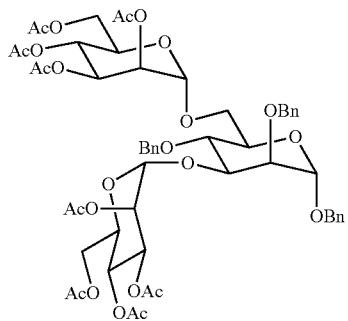 [SMILES: CC(=O)OCC1OC(OCC2OC(OCc3ccccc3)C(OCc3ccccc3)C(OC3OC(COC(C)=O)C(OC(C)=O)C(OC(C)=O)C3OC(C)=O)C2OCc2ccccc2)C(OC(C)=O)C(OC(C)=O)C1OC(C)=O]

Benzyl 2,4-di-O-benzyl-α-D-mannopyranoside (255 mg, 0.57 mmol) in DCM (10 mL) and 1',1',1'-trichloroacetimidate-2,3,4,6-tetra-O-acetyl-α-D-mannopyranoside (1.12 g, 2.27 mmol) in DCM (10 mL) were added to a dried flask containing activated 4 Å molecular sieves (ca 500 mg) via cannular. The resulting solution was stirred for 1 h, after which boron trifluoroetherate (90 μL, 0.85 mmol) was added. After a 16 h period, t.l.c. (petrol:ethyl acetate, 2:1) indicated the formation of a major product (R$_f$ 0.3) with complete consumption of the starting material (R$_f$ 0.1). The reaction was quenched with triethylamine (ca 5 mL) and the solution was filtered through Celite and concentrated in vacuo. The resulting residue was purified by flash column chromatography (petrol:ethyl acetate, 4:3) to afford the title compound (472 mg, 75%) as a white amorphous solid; $[\alpha]_D^{25}$+81.5 (c, 1.0 in CHCl$_3$); $\delta_H$ (500 MHz, CDCl$_3$) 1.98, 2.02, 2.05, 2.07, 2.09, 2.10, 2.11, 2.19 (24H, 8×s, 8×OAc), 3.74-3.76 (1H, m, H-6a), 3.81-3.87 (3H, m, H-2a, H-5a, H-6'a), 3.92-3.97 (3H m, H-4a, H-5b, H-6b), 4.03-4.22 (4H, m, H-3a, H-5c, H-6'b, H-6c), 4.27 (1H, dd, J$_{5,6'}$ 5.5 Hz, J$_{6,6'}$ 12.3 Hz, H-6'c), 4.54, 4.75 (2H Abq, J11.9 Hz, CH$_2$), 4.64, 4.81 (2H, Abq, J12.2 Hz, CH$_2$), 4.65, 4.91 (2H, Abq, J11.4 Hz, CH$_2$), 4.97 (1H, d, J$_{1,2}$ 1.7 Hz, H-1c), 5.00 (1H, d, J$_{1,2}$ 1.6 Hz, H-1a), 5.19 (1H, d, J$_{1,2}$ 1.7 Hz, H-1b), 5.25 (1H, at, J10.0 Hz, H-4b), 5.33 (1H, at, J10.1 Hz, H-4c), 5.36 (1H, dd, J$_{1,2}$ 1.8 Hz, J$_{2,3}$ 3.3 Hz, H-2c), 5.42 (1H, dd, J$_{1,2}$ 1.5 Hz, J$_{2,3}$ 3.5 Hz, H-2b), 5.44-5.47 (2H, m, H-3b, H-3c), 7.32-7.42 (15H m, ArH).

EXAMPLE 72

Acetyl 2,4-di-O-acetyl-3,6-bis-O-(2,3,4,6-tetra-O-acetyl-α-D-mannopyranoside)-α/β-D-mannopyranoside

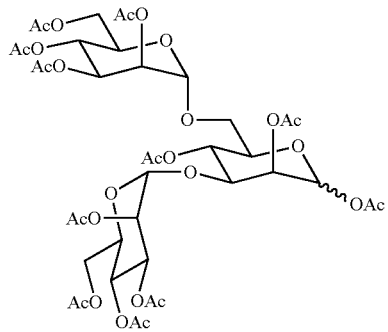 [SMILES: CC(=O)OCC1OC(OCC2OC(OC(C)=O)C(OC(C)=O)C(OC3OC(COC(C)=O)C(OC(C)=O)C(OC(C)=O)C3OC(C)=O)C2OC(C)=O)C(OC(C)=O)C(OC(C)=O)C1OC(C)=O]

Benzyl 2,4-di-O-benzyl-3,6-bis-O-(2,3,4,6-tetra-O-acetyl-α-D-mannopyranoside)-α-D-mannopyranoside (100 mg, 0.09 mmol) and Pearlman's catalyst Pd(OH)$_2$, moist, 35 mg) were dissolved in absolute ethanol (5 mL). The resulting solution was degassed and purged with hydrogen gas, then left to stir under an atmosphere of hydrogen. After a 4 day period, t.l.c. (ethyl acetate) indicated the formation of a major product (R$_f$ 0.4) with complete consumption of the starting material R$_f$ 0.9). The solution was filtered through Celite and concentrated in vacuo. The resulting residue was purified by flash column chromatography (ethyl acetate) to afford the intermediate 3,6-bis-(2,3,4,6-tetra-O-acetyl-α-D-mannopyranoside)-α/β-D-mannopyranoside (74 mg, 98%) as a white amorphous solid; m/z HRMS (ES$^+$) Calcd. for C$_{34}$H$_{48}$O$_{34}$Na (MNa$^+$) 863.2433. Found 863.2440. This intermediate (74 mg, 0.088 mmol) was resuspended in acetic anhydride (5 mL) and pyridine (5 mL). After 24 h t.l.c. (petrol:ethyl acetate, 2:3) indicated the formation of a product (R$_f$ 0.4) with complete consumption of the starting material (R$_f$ 0.0). The reaction was diluted with water (20 mL) and partitioned with ethyl acetate (20 mL) and the phases were separated. The aqueous layer was re-extracted with ethyl acetate (2×20 mL). The combined organic layers were washed with dilute hydrochloric acid (500 mL, 1M), sodium hydrogen carbonate (50 mL of a saturated aqueous solution), brine (30 mL), dried over MgSO$_4$, filtered and concentrated in vacuo to give the title compound (83 mg, 98%) as an amorphous foam being a mixture of anomers (α/β 5:1); $\delta_H$ (500 MHz, CDCl$_3$) α compound, 2.00, 2.02, 2.08, 2.12, 2.17, 2.18, 2.19, 2.26 (33H, 8×s, 11×OAc), 3.59 (1H, dd, J$_{5,6}$ 3.0 Hz, J$_{6,6'}$ 11.1 Hz, H-6a), 3.76 (1H, dd, J$_{5,6'}$ 5.2 Hz, J$_{6,6'}$ 11.2 Hz, H-6'a), 3.92 (1H, ddd, J$_{4,5}$ 10.2 Hz, J$_{5,6}$ 3.0 Hz, J$_{5,6'}$ 5.2 Hz, H-5a), 4.04-4.16 (4H, m, H-5b, H-5c, H-6b, H-6c), 4.21 (1H, dd, J$_{2,3}$ 3.4 Hz, J$_{3,4}$ 9.9 Hz, H-3a), 4.28 (1H, dd, J$_{5,6'}$ 5.5 Hz, J$_{6,6'}$ 12.2 Hz, H-6'b/c), 4.31 (1H, dd, J$_{5,6'}$ 4.7 Hz, J$_{6,6'}$ 12.3 Hz, H-6'b/c), 4.81 (1H, d, J$_{1,2}$ 1.5 Hz, H-1c), 5.06-5.07 (2H, m, H-1b, H-?), 5.20-5.35 (8H, m, H-2a, H-2b, H -2c, H-3b, H-3c, H-4a, H-4b, H-4c), 6.07 (1H, d, J$_{1,2}$ 1.8 Hz, H-1a). β compound selected data only 3.64 (1H, dd, J$_{5,6}$ 3.7 Hz, J$_{6,6'}$ 10.8 Hz, H-6a), 3.69-3.73 (1H, m, H-5a), 3.76 (1H, dd, J$_{5,6'}$ 5.2 Hz, J$_{6,6'\ 11.2}$ Hz, H-6'a), 4.01 (1H, dd, J$_{2,3}$ 3.2 Hz, J$_{3,4}$ 9.7 Hz, H-3a), 5.50 (1H, dd, J$_{1,2}$ 0.9 Hz, J$_{2,3}$ 3.2 Hz, H-2a), 5.83 (1H, d, J$_{1,2}$ 0.9 Hz, H-1a).

EXAMPLE 73

2,4-Di-O-acetyl-bis-O-(2,3,6-tri-O-acetyl-α-O-mannopyranosyl)-α-D-mannopyranosyl bromide

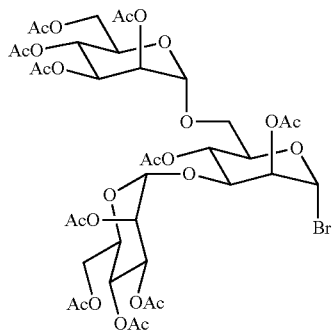 [SMILES: CC(=O)OCC1OC(OCC2OC(Br)C(OC(C)=O)C(OC3OC(COC(C)=O)C(OC(C)=O)C(OC(C)=O)C3OC(C)=O)C2OC(C)=O)C(OC(C)=O)C(OC(C)=O)C1OC(C)=O]

Acetyl 2,4-di-O-acetyl-3,6-bis-O-(2,3,4,6-tetra-O-acetyl-α-D-mannopyranoside)-α/β-D-mannopyranoside (87 mg, 0.09 mmol) was dissolved in anhydrous DCM (5 mL). To this hydrogen bromide (33% in acetic acid, 1 mL) was added. The mixture was stirred under argon at RT. After a 2 h period, t.l.c. (petrol:ethyl acetate, 1:4) indicated the formation of a product (R$_f$ 0.6) with complete consumption of the starting material (R$_f$ 0.4). The reaction mixture was partitioned between DCM (10 mL) and water (10 mL), and the aqueous layer was re-extracted with DCM (3×10 mL). The combined organic layers were washed with sodium hydrogen carbonate (20 mL of a saturated aqueous solution) until pH 8 was obtained, brine (20 mL), dried over MgSO$_4$, filtered and concentrated in vacuo to afford the title compound (80 mg, 90%) as a white foam which was taken on without further purification; $\delta_H$ (400 MHz, CDCl$_3$) 1.97, 1.99, 2.05, 2.06, 2.10, 2.12, 2.17, 2.24 (30H, 9×s, 10×OAc), 3.60 (1H, dd, J$_{5,6}$ 3.0 Hz, J$_{6,6'}$ 11.4 Hz, H-6a), 3.77 (1H, dd, J$_{5,6'}$ 4.5 Hz, J$_{6,6'}$ 11.4 Hz, H-6'a), 4.02-4.09 (5H, m, H-5a, H-5b, H-5c, H-6b, H-6c), 4.24 (1H, dd, J$_{5,6'}$ 6.8 Hz, J$_{6,6'}$ 12.2 Hz, H-6'), 4.29 (1H, dd, J$_{5,6'}$ 5.0 Hz, J$_{6,6'}$ 12.6 Hz, H-6'), 4.62 (1H, dd, J$_{2,3}$ 3.4 Hz, J$_{3,4}$ 10.0 Hz, H-3a), 4.79 (1H, bs, H-1c), 5.02-5.04 (2H, m, H-1b, H-3b), 5.17-5.30 (5H, m, H-2b, H-2c, H-3c, H-4b, H-4c), 5.39 (1H, at, J10.1 Hz, H-4a), 5.43 (1H, dd, J$_{1,2}$ 1.5 Hz, J$_{2,3}$ 3.2 Hz, H-2a), 6.34 (1H, bs, H-1a).

EXAMPLE 74

1-Thio-2,4-tetra-O-acetyl-3,6-O-bis-(2,3,4,6-tetra-O-acetyl-α-O-mannopyranosyl)-α-D-mannopyranose

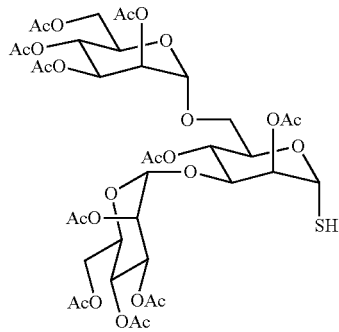 [SMILES: CC(=O)OCC1OC(OCC2OC(S)C(OC(C)=O)C(OC3OC(COC(C)=O)C(OC(C)=O)C(OC(C)=O)C3OC(C)=O)C2OC(C)=O)C(OC(C)=O)C(OC(C)=O)C1OC(C)=O]

2,4-Tetra-O-acetyl-3,6-O-bis-(2,3,4,6-tetra-O-acetyl-α-mannopyranosyl)-α-D-mannopyranosyl bromide (850 mg, 0.85 mmol) was dissolved in anhydrous acetone (20 mL). Anhydrous thiourea (115 mg, 1.56 mmol) was added and the mixture was heated to reflux under an atmosphere of argon. After 18 h, t.l.c. (petrol:ethyl acetate, 1:3) indicated the formation of a product (R$_f$ 0.0) with complete consumption of the starting material (R$_f$ 0.4). The reaction was concentrated in vacuo and the resutling residue was purified by column flash chromatography (ethyl acetate/methanol, 9:1) to afford the intermediate 2,4-tetra-O-acetyl-3,6-O-bis-(2,3,4,6-tetra-O-acetyl-α-O-mannopyranosyl)-α-D-mannopyranosyl-1-isothiouronium bromide (550 mg, 60%) which was carried on. This intermediate (550 mg, 0.51 mmol) and Na$_2$S$_2$O$_5$ (122 mg, 0.62 mmol) were added to a stirred mixture of DCM (20 mL) and water (10 mL). The mixture was heated to reflux under argon. After 2.5 h, t.l.c. (petrol:ethyl acetate, 1:3) indicated the formation of a product (R$_f$ 0.3) with complete consumption of the starting material (R$_f$ 0.0), at which point the reaction was cooled to RT and the phases separated. The aqueous layer was re-extracted with DCM (2×20 mL). The combined organic layers were washed with sodium hydrogen carbonate (20 mL of a saturated aqueous solution), brine (20 mL), dried (MgSO$_4$), filtered and the solvent removed in vacuo. The resulting residue was purified by flash column chromatography (petrol:ethyl acetate, 1:3) to afford the title compound (350 mg, 73%) as a white amorphous solid; [α]$_D^{23}$+58.1 (c, 1.2 in CHCl$_3$; $\delta_H$ (500 MHz, C$_6$D$_6$) 1.74, 1.75, 1.78, 1.82, 1.91, 2.03, 2.06, 2.26 (24H, 8×s, 10×Oac), 2.07 (1H, bs, SH), 3.65 (1H, dd, J$_{5,6}$ 3.2 Hz, J$_{6,6'}$ 11.0 Hz, H-6a), 3.93 (1H, dd, J$_{5,6'}$ 5.3 Hz, J$_{6,6'}$ 11.1 Hz, H-6'a), 4.31-4.38 (4H, m, H-3a, H-5a, H-5b/c, H-6), 4.43-4.45 (1H, m, H-6), 4.51 (1H, dd, J$_{5,6'}$ 5.6 Hz, J$_{6,6'}$ 12.6 Hz, H-6'), 4.56-4.60 (2H, m, H-5b/c, H-6'), 4.91 (1H, d, J$_{1,2}$ 1.5 Hz, H-1c), 5.20 (1H, d, J$_{1,2}$ 1.8 Hz, H-1b), 5.43 (1H, dd, J$_{1,2}$ 1.8 Hz, J$_{2,3}$ 3.1 Hz, H-2b), 5.45 (1H, bs, H-1), 5.65 (1H, dd, J$_{1,2}$ 1.5 Hz, J$_{2,3}$ 3.1 Hz, H-2a), 5.70-5.82 (5H, m, H-2c, H-3b, H-4a, H-4b, H-4c), 5.85 (1H, dd, J$_{2,3}$ 3.2 Hz, J$_{3,4}$ 10.2 Hz, H-3c).

EXAMPLE 75

Representative Protein Glycosylation Procedures of SBLCys156 Using Man(1-6)Man(1-3)ManSH 1-Thio-2,4-tetra-O-acetyl-3,6-O-bis-(2,3,4,6-tetra-O-acetyl-α-O-mannopyranosyl)-α-D-mannopyranose (20 mg, 0.02 mmol) and sodium methoxide (2 mg, 0.02 mmol) were added to a stirred solution of methanol (5 mL). After 12 h, (petrol:ethyl acetate, 1:2) indicated the formation of a product ($R_f$ 0.0) with the complete consumption of the starting material ($R_f$ 0.2). The reaction was neutralised with the addition of Dowex®-50 ion exchange resin after which point the reaction was filtered and concentrated in vacuo. The crude sugar thiol was taken up into water (5 mL) of which 38 μL was added to aqueous buffer solution (500 μL, 70 mM CHES, 5 mM MES, 2 mM $CaCl_2$, pH 9.5) containing SBL156CysSePh (1 mg). The resulting solution placed on an end-over-end rotator. After 1 h the reaction mixture was loaded onto a PD10 Sephadex® G25 column and eluted with 70 mM HEPES, 2 mM CaCl2, pH 7.0. The protein fraction was collected to afford Man(Man)Man-S-SBLCys156; m/z ($ES^+$) found 27878, calcd. 27881.

The invention claimed is:

1. A method of chemically modifying a protein, peptide or amino acid comprising at least one selenenylsulfide group, the method comprising reacting the protein, peptide or amino acid with a carbohydrate compound comprising a thiol group.

2. The method according to claim 1, wherein the protein, peptide or amino acid comprising at least one selenenylsulfide group is a group of formula: protein-S—Se-Ph.

3. The method according to claim 1, wherein the protein is SBLCys156 and the thiol group is GlcSH.

* * * * *